(12) United States Patent
Takaki et al.

(10) Patent No.: US 8,685,620 B2
(45) Date of Patent: *Apr. 1, 2014

(54) RESIST COMPOSITION, METHOD OF FORMING RESIST PATTERN AND POLYMERIC COMPOUND

(71) Applicant: Tokyo Ohka Kogyo Co., Ltd., Kawasaki (JP)

(72) Inventors: Daichi Takaki, Kawasaki (JP); Daiju Shiono, Kawasaki (JP); Yoshiyuki Utsumi, Kawasaki (JP); Takaaki Kaiho, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/670,106

(22) Filed: Nov. 6, 2012

(65) Prior Publication Data

US 2013/0115554 A1    May 9, 2013

(30) Foreign Application Priority Data

Nov. 9, 2011   (JP) ................................. 2011-245904

(51) Int. Cl.
*G03F 7/039* (2006.01)
*G03F 7/20* (2006.01)
*G03F 7/30* (2006.01)

(52) U.S. Cl.
USPC ........ 430/270.1; 430/311; 430/326; 430/905; 430/906; 430/907; 430/910; 526/288; 526/303.1; 526/304; 526/305; 526/307.7; 526/312

(58) Field of Classification Search
None
See application file for complete search history.

(56) References Cited

U.S. PATENT DOCUMENTS

| | | | |
|---|---|---|---|
| 5,945,517 A | 8/1999 | Nitta et al. | |
| 6,153,733 A | 11/2000 | Yukawa et al. | |
| 6,949,325 B2 | 9/2005 | Li et al. | |
| 2001/0049073 A1 | 12/2001 | Hada et al. | |
| 2002/0068235 A1* | 6/2002 | Fujita et al. | 430/192 |
| 2004/0110085 A1 | 6/2004 | Iwai et al. | |
| 2007/0231708 A1 | 10/2007 | Matsumaru et al. | |
| 2009/0047602 A1 | 2/2009 | Furuya et al. | |
| 2011/0177453 A1 | 7/2011 | Masubuchi et al. | |
| 2011/0244392 A1 | 10/2011 | Hirano et al. | |
| 2013/0095427 A1* | 4/2013 | Yahagi et al. | 430/285.1 |

FOREIGN PATENT DOCUMENTS

| | | |
|---|---|---|
| JP | A-09-208554 | 8/1997 |
| JP | A-10-221852 | 8/1998 |
| JP | A-11-035551 | 9/1999 |
| JP | A-11-035552 | 9/1999 |
| JP | A-11-035573 | 9/1999 |
| JP | A-11-322707 | 11/1999 |
| JP | A-2000-206694 | 7/2000 |
| JP | 2000-310857 | * 11/2000 |
| JP | A-2003-241385 | 8/2003 |
| JP | A-2005-336452 | 12/2005 |
| JP | A-2006-045311 | 2/2006 |
| JP | A-2006-063318 | 3/2006 |
| JP | A-2006-259582 | 9/2006 |
| JP | A-2006-317803 | 11/2006 |
| JP | A-2008-309938 | 12/2008 |
| JP | A-2009-025723 | 2/2009 |
| JP | A-2009-139909 | 6/2009 |
| JP | A-2010-095643 | 4/2010 |
| JP | A-2011-158879 | 8/2011 |
| WO | WO 2004/074242 A2 | 9/2004 |

OTHER PUBLICATIONS

Machine-assited English translation of JP2000-310857, provided by JPO (2000).*

* cited by examiner

*Primary Examiner* — Sin J. Lee
(74) *Attorney, Agent, or Firm* — Knobbe Martens Olson & Bear LLP

(57) ABSTRACT

A resist composition including a base component (A) which exhibits changed solubility in a developing solution under action of acid and an acid-generator component (B) which generates acid upon exposure, the base component (A) containing a polymeric compound (A1) having a structural unit (a5) represented by general formula (a5-0) shown below ($R^1$ represents a sulfur atom or an oxygen atom; $R^2$ represents a single bond or a divalent linking group; and Y represents an aromatic hydrocarbon group or an aliphatic hydrocarbon group having a polycyclic group, provided that the aromatic hydrocarbon group or the aliphatic hydrocarbon may have a carbon atom or a hydrogen atom thereof substituted with a substituent.

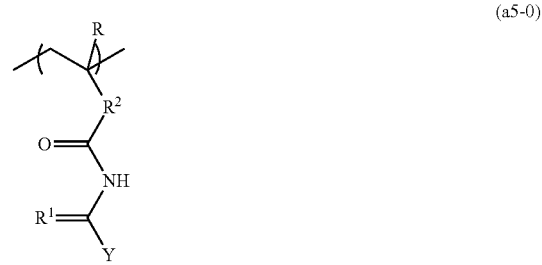

(a5-0)

5 Claims, No Drawings

RESIST COMPOSITION, METHOD OF FORMING RESIST PATTERN AND POLYMERIC COMPOUND

TECHNICAL FIELD

The present invention relates to a novel compound, a polymeric compound including a structural unit derived from the compound, a resist composition including the polymeric compound, and a method of forming a resist pattern using the resist composition.

Priority is claimed on Japanese Patent Application No. 2011-245904, filed Nov. 9, 2011, the content of which is incorporated herein by reference.

BACKGROUND ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film.

A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have lead to rapid progress in the field of pattern miniaturization.

Typically, these miniaturization techniques involve shortening the wavelength (increasing the energy) of the exposure light source. Conventionally, ultraviolet radiation typified by g-line and i-line radiation has been used, but nowadays KrF excimer lasers and ArF excimer lasers are starting to be introduced in mass production. Furthermore, research is also being conducted into lithography techniques that use an exposure light source having a wavelength shorter (energy higher) than these excimer lasers, such as electron beam, extreme ultraviolet radiation (EUV), and X ray.

Resist materials for use with these types of exposure light sources require lithography properties such as a high resolution capable of reproducing patterns of minute dimensions, and a high level of sensitivity to these types of exposure light sources.

As a resist material that satisfies these conditions, a chemically amplified composition is used, which includes a base material component that exhibits a changed solubility in a developing solution under the action of acid and an acid-generator component that generates acid upon exposure.

For example, in the case where the developing solution is an alkali developing solution (alkali developing process), a chemically amplified positive resist which contains, as a base component (base resin), a resin which exhibits increased solubility in an alkali developing solution under action of acid, and an acid generator is typically used. If the resist film formed using the resist composition is selectively exposed during formation of a resist pattern, then within the exposed portions, acid is generated from the acid-generator component, and the action of this acid causes an increase in the solubility of the resin component in an alkali developing solution, making the exposed portions soluble in the alkali developing solution. In this manner, the unexposed portions remain to form a positive resist pattern. The base resin used exhibits increased polarity by the action of acid, thereby exhibiting increased solubility in an alkali developing solution, whereas the solubility in an organic solvent is decreased. When such a base resin is applied to a process using a developing solution containing an organic solvent (organic developing solution) (hereafter, this process is referred to as "solvent developing process" or "negative tone-developing process") instead of an alkali developing process, the solubility of the exposed portions in an organic developing solution is decreased. Therefore, in a solvent developing process, the unexposed portions of the resist film are dissolved and removed by an organic solvent-type developing solution to thereby form a negative-tone resist pattern in which the exposed portions remain. For example, Patent Document 1 proposes a negative tone-developing process and a resist composition used for the process.

Currently, resins that contain structural units derived from (meth)acrylate esters within the main chain (acrylic resins) are now widely used as base resins for resist compositions that use ArF excimer laser lithography, as they exhibit excellent transparency in the vicinity of 193 nm (for example, see Patent Document 2).

In general, the base resin contains a plurality of structural units for improving lithography properties and the like. For example, in the case of a resin component which exhibits increased polarity by the action of acid, a base resin containing a plurality of structural units such as a structural unit having an acid decomposable group that is decomposed by the action of acid generated from the acid generator component, a structural unit having a polar group such as a hydroxyl group, a structural unit having a lactone structure, and the like is typically used. In particular, structural units having a polar group are widely used as they enhance the affinity for an alkali developing solution, and contributes to improvement in resolution.

Recently, a base resin having a structural unit containing an imide group has been proposed (see Patent Document 3). It is presumed that such as base resin contributes to improvement in resolution and mask reproducibility.

DOCUMENTS OF RELATED ART

Patent Document

[Patent Document 1] Japanese Unexamined Patent Application, First Publication No. 2009-025723
[Patent Document 2] Japanese Unexamined Patent Application, First Publication No. 2003-241385
[Patent Document 3] Japanese Unexamined Patent Application, First Publication No. 2006-063318

SUMMARY OF THE INVENTION

As further progress is made in lithography techniques and the application field for lithography techniques is expected to expand, development of a novel material for use in lithography will be desired.

For example, as miniaturization of resist patterns progress, further improvement will be demanded for resist materials with respect to various lithography properties such as resolution, roughness (LWR (line width roughness: non-uniformity of the line width) and the like in the case of a line pattern, and circularity in the case of a hole pattern), and exposure latitude, as well as high sensitivity.

In addition, as progress is made in lithography techniques (miniaturization), downsizing of the thickness of the resist film is proceeding. Thus, improvement in etching resistance is also demanded when etching is conducted using the pattern portion as a mask.

The present invention takes the above circumstances into consideration, with an object of providing a resist composition which exhibits excellent sensitivity, resolution, lithography properties and etching resistance, a compound useful for the resist composition, and a method of forming a resist pattern using the resist composition.

For solving the above-mentioned problems, the present invention employs the following aspects.

Specifically, a first aspect of the present invention is a resist composition including a base component (A) which exhibits changed solubility in a developing solution under action of acid and an acid-generator component (B) which generates acid upon exposure, the base component (A) containing a polymeric compound (A1) having a structural unit (a5) represented by general formula (a5-0) shown below.

[Chemical Formula 1]

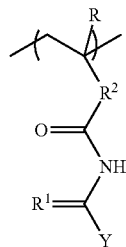

(a5-0)

In the formula, R represents a hydrogen atom, an alkyl group of 1 to 5 carbon atoms or a halogenated alkyl group of 1 to 5 carbon atoms; $R^1$ represents a sulfur atom or an oxygen atom; $R^2$ represents a single bond or a divalent linking group; and Y represents an aromatic hydrocarbon group or an aliphatic hydrocarbon group having a polycyclic group, provided that the aromatic hydrocarbon group or the aliphatic hydrocarbon may have a carbon atom or a hydrogen atom thereof substituted with a substituent.

A second aspect of the present invention is a method of forming a resist pattern, including: using a resist composition according to the first aspect to form a resist film on a substrate, subjecting the resist film to exposure, and subjecting the resist film to developing to form a resist pattern.

A third aspect of the present invention is a compound represented by general formula (1) shown below.

[Chemical Formula 2]

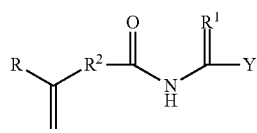

(1)

In the formula, R represents a hydrogen atom, an alkyl group of 1 to 5 carbon atoms or a halogenated alkyl group of 1 to 5 carbon atoms; $R^1$ represents a sulfur atom or an oxygen atom; $R^2$ represents a single bond or a divalent linking group; and Y represents an aromatic hydrocarbon group or an aliphatic hydrocarbon group having a polycyclic group, provided that the aromatic hydrocarbon group or the aliphatic hydrocarbon may have a carbon atom or a hydrogen atom thereof substituted with a substituent.

A fourth aspect of the present invention is a polymeric compound having a structural unit (a5) represented by general formula (a5-0) shown below.

[Chemical Formula 3]

(a5-0)

In the formula, R represents a hydrogen atom, an alkyl group of 1 to 5 carbon atoms or a halogenated alkyl group of 1 to 5 carbon atoms; $R^1$ represents a sulfur atom or an oxygen atom; $R^2$ represents a single bond or a divalent linking group; and Y represents an aromatic hydrocarbon group or an aliphatic hydrocarbon group having a polycyclic group, provided that the aromatic hydrocarbon group or the aliphatic hydrocarbon may have a carbon atom or a hydrogen atom thereof substituted with a substituent.

In the present description and claims, the term "aliphatic" is a relative concept used in relation to the term "aromatic", and defines a group or compound that has no aromaticity.

The term "alkyl group" includes linear, branched or cyclic, monovalent saturated hydrocarbon, unless otherwise specified. The same applies for the alkyl group within an alkoxy group.

The term "alkylene group" includes linear, branched or cyclic, divalent saturated hydrocarbon, unless otherwise specified.

A "halogenated alkyl group" is a group in which part or all of the hydrogen atoms of an alkyl group is substituted with a halogen atom, and a "halogenated alkylene group" is a group in which part or all of the hydrogen atoms of an alkylene group is substituted with a halogen atom. Examples of the halogen atom include a fluorine atom, a chlorine atom, a bromine atom and an iodine atom.

A "fluorinated alkyl group" is a group in which part or all of the hydrogen atoms within an alkyl group have been substituted with a fluorine atom. A "fluorinated alkylene group" is a group in which part or all of the hydrogen atoms within an alkylene group have been substituted with a fluorine atom.

A "hydroxyalkyl group" is a group in which part or all of the hydrogen atoms within an alkyl group have been substituted with a hydroxyl group.

The term "structural unit" refers to a monomer unit that contributes to the formation of a polymeric compound (resin, polymer, copolymer).

The term "exposure" is used as a general concept that includes irradiation with any form of radiation.

According to the present invention, there are provided a resist composition which exhibits excellent sensitivity, resolution, lithography properties and etching resistance, a compound useful for the resist composition, a polymeric compound having a structural unit derived from the compound, and a method of forming a resist pattern using the resist composition.

MODE FOR CARRYING OUT THE INVENTION

<<Resist Composition>>

The resist composition of the present invention includes a base component (A) (hereafter, referred to as "component (A)") which exhibits changed solubility in a developing solution under action of acid, and an acid-generator component (B) (hereafter, referred to as "component (B)") which generates acid upon exposure.

When a resist film is formed using the resist composition and the formed resist film is subjected to a selective exposure, acid is generated from the component (B) at exposed portions, and the generated acid acts on the component (A) to change the solubility of the component (A) in a developing solution, whereas the solubility of the component (A) in a developing solution is not changed at unexposed portions, thereby generating difference in solubility in a developing solution between exposed portions and unexposed portions. Therefore, by subjecting the resist film to development, the exposed portions are dissolved and removed to form a positive-tone resist pattern in the case of a positive resist, whereas the unexposed portions are dissolved and removed to form a negative-tone resist pattern in the case of a negative resist.

In the present specification, a resist composition which forms a positive resist pattern by dissolving and removing the exposed portions is called a positive resist composition, and a resist composition which forms a negative resist pattern by dissolving and removing the unexposed portions is called a negative resist composition.

The resist composition of the present invention may be either a positive resist composition or a negative resist composition.

Further, in the formation of a resist pattern, the resist composition of the present invention can be applied to an alkali developing process using an alkali developing solution in the developing treatment, or a solvent developing process using a developing solution containing an organic solvent (organic developing solution) in the developing treatment.

<Component (A)>

The component (A) used in the resist composition of the present invention includes a polymeric compound (A1) (hereafter, referred to as "component (A1)") including a structural unit (a5) represented by general formula (a5-0).

Here, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The organic compound used as the base component is broadly classified into non-polymers and polymers.

In general, as a non-polymer, any of those which have a molecular weight in the range of 500 to less than 4,000 is used. Hereafter, a "low molecular weight compound" refers to a non-polymer having a molecular weight in the range of 500 to less than 4,000.

As a polymer, any of those which have a molecular weight of 1,000 or more is generally used. Hereafter, a "polymeric compound" or a "resin" refers to a polymer having a molecular weight of 1,000 or more.

As the molecular weight of the polymer, the weight average molecular weight in terms of the polystyrene equivalent value determined by gel permeation chromatography (GPC) is used.

[Component (A1)]

The component (A1) may be a resin that exhibits increased solubility in a developing solution under action of acid or a resin that exhibits decreased solubility in a developing solution under action of acid.

When the resist composition of the present invention is a resist composition that forms a negative-tone resist pattern in an alkali developing process (or a positive-tone resist pattern in a solvent developing process), as the component (A1), a polymeric compound that is soluble in an alkali developing solution (hereafter, this polymeric compound is sometimes referred to as "component (A1-2)") is preferably used, and a cross-linking component is further added.

The component (A1-2) generally has an alkali-soluble group such as a hydroxy group, a carboxy group or an amino group. The cross-linking component used has a reactive group such as a methylol group or an alkoxymethyl group that reacts with the alkali-soluble group by the action of acid. When a resist film is formed using the resist composition and the formed resist film is subjected to a selective exposure, acid is generated from the component (B) at exposed portions, and the action of acid causes cross-linking between the component (A1-2) and the cross-linking component, thereby decreasing the number of alkali-soluble groups of the component (A1-2) and the polarity, and increasing the molecular weight. As a result, solubility in an alkali developing solution is decreased (solubility in an organic developing solution is increased). Therefore, in the formation of a resist pattern, by conducting selective exposure of a resist film formed by applying the resist composition to a substrate, the exposed portions become insoluble in an alkali developing solution (soluble in an organic developing solution), whereas the unexposed portions remain soluble in an alkali developing solution (insoluble in an organic developing solution), and hence, a negative resist pattern can be formed by conducting development using an alkali developing solution. On the other hand, when an organic developing solution is used as the developing solution, a positive resist pattern can be formed.

As the cross-linking agent, typically, an amino-based cross-linking agent such as a glycoluril having a methylol group or alkoxymethyl group, or a melamine-based cross-linking agent is preferable, as it enables formation of a resist pattern with minimal swelling. The amount of the cross-linker added is preferably within a range from 1 to 50 parts by weight, relative to 100 parts by weight of the alkali-soluble resin.

When component (A1-2) is self-crosslinkable (e.g., when the component (A1-2) has a group that reacts with an alkali-soluble group by the action of acid), the cross-linking component does not necessarily be added.

When the resist composition of the present invention is a resist composition that forms a positive-tone resist pattern in an alkali developing process (or a negative-tone resist pattern in a solvent developing process), as the component (A1), a polymeric compound that exhibits increased polarity by the action of acid (hereafter, this polymeric compound is sometimes referred to as "(A1-1)") is preferably used. Since the polarity of the component (A1-1) is changed prior to and after exposure, by using the component (A1-1), an excellent development contrast can be achieved not only in an alkali developing process, but also in a solvent developing process.

More specifically, in the case of applying an alkali developing process, the component (A1-1) is substantially insoluble in an alkali developing solution prior to exposure, but when acid is generated from the component (B) upon exposure, the action of this acid causes an increase in the polarity of the base component, thereby increasing the solubility of the component (A1-1) in an alkali developing solution. Therefore, in the formation of a resist pattern, by conducting selective exposure of a resist film formed by applying the resist composition to a substrate, the exposed portions change from an insoluble state to a soluble state in an alkali developing solution, whereas the unexposed portions remain insoluble in an alkali developing solution, and hence, contrast can be obtained between the exposed portions and the unexposed portions, and a positive resist pattern can be formed by alkali developing. On the other hand, in the case of a solvent developing process, the component (A1-1) exhibits high solubility in an organic developing solution prior to exposure, and when acid is generated from the component (B) upon exposure, the polarity of the component (A-1) is increased by the action of the generated acid, thereby decreasing the solubility of the component (A1-1) in an organic developing solution. Therefore, in the formation of a resist pattern, by conducting selective exposure of a resist film formed by applying the resist composition to a substrate, the exposed portions changes from an soluble state to an insoluble state in an organic developing solution, whereas the unexposed portions remain soluble in an organic developing solution. As a result, by conducting development using an organic developing solution, a contrast can be made between the exposed portions and unexposed portions, thereby enabling the formation of a negative resist pattern.

Among these, as the component (A1), the component (A1-1) is preferable. That is, the resist composition of the present invention is preferably a chemically amplified resist composition which becomes a positive type in the case of an alkali developing process, and a negative type in the case of a solvent developing process.

As the component (A1-1), it is particularly desirable to include, in addition to the structural unit (a5), a structural unit (a1) containing an acid decomposable group that exhibits increased polarity by the action of acid. As the structural unit (a1), a structural unit derived from an acrylate ester which may have the hydrogen atom bonded to the carbon atom on the α-position substituted with a substituent is preferable.

The component (A1-1) preferably includes, in addition to the structural unit (a5) and the structural unit (a1), a structural unit (a2) containing a —$SO_2$— containing cyclic group or a lactone-containing cyclic group.

Further, the component (A1-1) preferably includes, in addition to the structural unit (a5) and the structural unit (a1), or in addition to the structural unit (a5), the structural unit (a1) and the structural unit (a2), a structural unit (a3) containing a polar group.

Structural Unit (a5)

The structural unit (a5) is a structural unit represented by general formula (a5-0) shown below.

[Chemical Formula 4]

(a5-0)

In the formula, R represents a hydrogen atom, an alkyl group of 1 to 5 carbon atoms or a halogenated alkyl group of 1 to 5 carbon atoms; $R^1$ represents a sulfur atom or an oxygen atom; $R^2$ represents a single bond or a divalent linking group; and Y represents an aromatic hydrocarbon group or an aliphatic hydrocarbon group having a polycyclic group, provided that the aromatic hydrocarbon group or the aliphatic hydrocarbon group may have a carbon atom or a hydrogen atom thereof substituted with a substituent.

In formula (a5-0), R represents a hydrogen atom, an alkyl group of 1 to 5 carbon atoms or a halogenated alkyl group of 1 to 5 carbon atoms.

Examples of the alkyl group of 1 to 5 carbon atoms for R include linear or branched alkyl groups such as a methyl group, an ethyl group, a propyl group, an isopropyl group, an n-butyl group, an isobutyl group, a tert-butyl group, a pentyl group, an isopentyl group and a neopentyl group.

Examples of the halogenated alkyl group of 1 to 5 carbon atoms for R include groups in which part or all of the hydrogen atoms of the aforementioned alkyl groups of 1 to 5 carbon atoms have been substituted with halogen atoms. Examples of the halogen atom include a fluorine atom, a chlorine atom, a bromine atom and an iodine atom, and a fluorine atom is particularly desirable.

As R, a hydrogen atom, an alkyl group of 1 to 5 carbon atoms or a fluorinated alkyl group of 1 to 5 carbon atoms is preferable, a hydrogen atom or an alkyl group of 1 to 5 carbon atoms is more preferable, and a hydrogen atom or a methyl group is particularly desirable.

In formula (a5-0), $R^1$ represents a sulfur atom or an oxygen atom, and an oxygen atom is preferable.

In the formula (a5-0), $R^2$ represents a single bond or a divalent linking group.

The divalent linking group for $R^2$ is not particularly limited, and preferable examples thereof include a divalent hydrocarbon group which may have a substituent and a divalent linking group containing a hetero atom.

(Divalent Hydrocarbon Group which May have a Substituent)

A hydrocarbon "has a substituent" means that part or all of the hydrogen atoms within the hydrocarbon group is substituted with a substituent (a group or an atom other than hydrogen).

The hydrocarbon group may be either an aliphatic hydrocarbon group or an aromatic hydrocarbon group. An "aliphatic hydrocarbon group" refers to a hydrocarbon group that has no aromaticity.

The divalent aliphatic hydrocarbon group as the divalent hydrocarbon group for $R^2$ may be either saturated or unsaturated. In general, the divalent aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

The linear or branched aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, branched alkylene groups are preferred, and specific examples include various alkylalkylene groups, including alkylmethylene groups such as —CH(CH₃)—, —CH(CH₂CH₃)—, —C(CH₃)₂—, —C(CH₃)(CH₂CH₃)—, —C(CH₃)(CH₂CH₂CH₃)—, and —C(CH₂CH₃)₂—; alkylethylene groups such as —CH(CH₃)CH₂—, —CH(CH₃)CH(CH₃)—, —C(CH₃)₂CH₂—, —CH(CH₂CH₃)CH₂—, and —C(CH₂CH₃)₂—CH₂—; alkyltrimethylene groups such as —CH(CH₃)CH₂CH₂—, and —CH₂CH(CH₃)CH₂—; and alkyltetramethylene groups such as —CH(CH₃)CH₂CH₂CH₂—, and —CH₂CH(CH₃)CH₂CH₂—. As the alkyl group within the alkylalkylene group, a linear alkyl group of 1 to 5 carbon atoms is preferable.

The linear or branched aliphatic hydrocarbon group may or may not have a substituent. Examples of the substituent include a fluorine atom, a fluorinated alkyl group of 1 to 5 carbon atoms, and an oxygen atom (=O).

As examples of the hydrocarbon group containing a ring in the structure thereof, an alicyclic hydrocarbon group (a group in which two hydrogen atoms have been removed from an aliphatic hydrocarbon ring), a group in which the alicyclic hydrocarbon group is bonded to the terminal of the aforementioned chain-like aliphatic hydrocarbon group, and a group in which the alicyclic group is interposed within the aforementioned linear or branched aliphatic hydrocarbon group, can be given. As the linear or branched aliphatic hydrocarbon group, the same groups as those described above can be used.

The alicyclic hydrocarbon group preferably has 3 to 20 carbon atoms, and more preferably 3 to 12 carbon atoms.

The alicyclic hydrocarbon group may be either a monocyclic group or a polycyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which two hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The alicyclic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (=O).

The aromatic hydrocarbon group as the divalent hydrocarbon group for $R^2$ is a hydrocarbon group having an aromatic ring.

The aromatic hydrocarbon ring preferably has 3 to 30 carbon atoms, more preferably 5 to 30, still more preferably 5 to 20, still more preferably 6 to 15, and most preferably 6 to 10. Here, the number of carbon atoms within a substituent(s) is not included in the number of carbon atoms of the aromatic hydrocarbon group.

Examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom.

Examples of the hetero atom within the aromatic hetero rings include an oxygen atom, a sulfur atom and a nitrogen atom.

Specific examples of the aromatic hydrocarbon group include a group in which two hydrogen atoms have been removed from the aforementioned aromatic hydrocarbon ring (arylene group); and a group in which one hydrogen atom has been removed from the aforementioned aromatic hydrocarbon ring (aryl group) and one hydrogen atom has been substituted with an alkylene group (such as a benzyl group, a phenethyl group, a 1-naphthylmethyl group, a 2-naphthylmethyl group, a 1-naphthylethyl group, or a 2-naphthylethyl group). The alkylene group (alkyl chain within the arylalkyl group) preferably has 1 to 4 carbon atom, more preferably 1 or 2, and most preferably 1.

The aromatic hydrocarbon group may or may not have a substituent. For example, the hydrogen atom bonded to the aromatic hydrocarbon ring within the aromatic hydrocarbon group may be substituted with a substituent. Examples of substituents include an alkyl group, an alkoxy group, a halogen atom, a halogenated alkyl group, a hydroxyl group and an oxygen atom (=O).

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom as the substituent for the aromatic hydrocarbon group include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

(Divalent Linking Group Containing a Hetero Atom)

With respect to a "divalent linking group containing a hetero atom" for $R^2$, a hetero atom is an atom other than carbon and hydrogen, and examples thereof include an oxygen atom, a nitrogen atom, a sulfur atom and a halogen atom.

Examples of the divalent linking group containing a hetero atom include —O—, —C(=O)—O—, —C(=O)—, —O—C(=O)—O—, —C(=O)—NH—, —NH— (H may be substituted with a substituent such as an alkyl group or an acyl group), —S—, —S(=O)₂—, —S(=O)₂—O—, —NH—C(=O)—, =N—, and a group represented by general formula —$Y^{21}$—O—$Y^{22}$—, —[$Y^{21}$—C(=O)—O]$_{m'}$—$Y^{22}$—, —C(=O)—O—$Y^{22}$— or —$Y^{21}$—O—C(=O)—$Y^{22}$— [in the formulae, each of $Y^{21}$ and $Y^{22}$ independently represents a divalent hydrocarbon group which may have a substituent; O represents an oxygen atom; and m' represents an integer of 0 to 3].

When $R^2$ represents —NH—, H may be replaced with a substituent such as an alkyl group, an acyl group or the like. The substituent (an alkyl group, an acyl group or the like) preferably has 1 to 10 carbon atoms, more preferably 1 to 8, and most preferably 1 to 5.

Each of $Y^{21}$ and $Y^{22}$ independently represents a divalent hydrocarbon group which may have a substituent. As the divalent hydrocarbon group, the same groups as those described above for the "divalent hydrocarbon group which may have a substituent" for $R^2$ can be mentioned.

As $Y^{21}$, a linear aliphatic hydrocarbon group is preferable, more preferably a linear alkylene group, still more preferably a linear alkylene group of 1 to 5 carbon atoms, and a methylene group or an ethylene group is particularly desirable.

As $Y^{22}$, a linear or branched aliphatic hydrocarbon group is preferable, and a methylene group, an ethylene group or an alkylmethylene group is more preferable. The alkyl group within the alkylmethylene group is preferably a linear alkyl group of 1 to 5 carbon atoms, more preferably a linear alkyl group of 1 to 3 carbon atoms, and most preferably a methyl group.

In the group represented by the formula $-[Y^{21}-C(=O)-O]_{m'}-Y^{22}-$, m' represents an integer of 0 to 3, preferably an integer of 0 to 2, more preferably 0 or 1, and most preferably 1. Namely, it is particularly desirable that the group represented by the formula $-[Y^{21}-C(=O)-O]_{m'}-Y^{22}$ is a group represented by the formula $-Y^{21}-C(=O)-O-Y^{22}-$. Among these, a group represented by the formula $-(CH_2)_{a'}-C(=O)-O-(CH_2)_{b'}-$ is preferable. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

As the divalent linking group containing a hetero atom, a linear group containing an oxygen atom as the hetero atom e.g., a group containing an ether bond or an ester bond is preferable, and a group represented by the aforementioned formula $-Y^{21}-O-Y^{22}-$, $-[Y^{21}-C(=O)-O]_{m'}-Y^{22}-$, $-C(=O)-O-Y^{22}-$ or $-Y^{21}-O-C(=O)-Y^{22}-$ is more preferable.

Among these, as $R^2$, a single bond or a divalent linking group containing a hetero atom is preferable, a single bond, a group represented by the aforementioned formula $-Y^{21}-O-Y^{22}-$, a group represented by the aforementioned formula $-[Y^{21}-C(=O)-O]_{m'}-Y^{22}-$ or a group represented by the aforementioned formula $-C(=O)-O-Y^{22}-$ or a group represented by the aforementioned formula $-Y^{21}-O-C(=O)-Y^{22}-$ is more preferable, a single bond or $-C(=O)-O-Y^{22}-$ is most preferable.

In the formula (a5-0), Y represents an aromatic hydrocarbon group or an aliphatic hydrocarbon group having a polycyclic group, provided that the aromatic hydrocarbon group or the aliphatic hydrocarbon may have a carbon atom or a hydrogen atom thereof substituted with a substituent.

Examples of the aromatic hydrocarbon group for Y include groups in which one hydrogen atom has been removed from the aromatic ring (aromatic hydrocarbon ring) explained above for $R^2$; and groups in which one hydrogen atom of the hydrocarbon ring has been substituted with an alkylene group (e.g., arylalkyl groups, such as a benzyl group, a phenethyl group, a 1-naphthylmethyl group, a 2-naphthylmethyl group, a 1-naphthylethyl group, and a 2-naphthylethyl group).

The alkylene group (alkyl chain within the arylalkyl group) preferably has 1 to 4 carbon atom, more preferably 1 or 2, and most preferably 1.

Among these, as the aromatic hydrocarbon group for Y, a group in which one hydrogen atom has been removed from an aromatic ring (aromatic hydrocarbon ring) is preferable, and a phenyl group or a naphthyl group is particularly desirable.

The aromatic hydrocarbon group for Y may have a carbon atom or a hydrogen atom thereof substituted with a substituent. The substituent includes atoms and atomic groups.

As an example of the aromatic hydrocarbon group in which a carbon atom has been substituted with a substituent, an aromatic heterocyclic group in which part of carbon atoms constituting an aromatic hydrocarbon ring has been substituted with a hetero atom can be mentioned. Examples of the hetero atom within the aromatic heterocyclic group include an oxygen atom, a sulfur atom and a nitrogen atom.

In the case where a hydrogen atom of the aromatic hydrocarbon group is substituted with a substituent, examples of the substituent include an alkyl group, an alkoxy group, a halogen atom, a halogenated alkyl group, a hydroxy group, an oxygen atom (=O), and an amino group-containing group such as $-NH_2$ or $-SO_2-NH_2$.

As the alkyl group for the substituent, an alkyl group of 1 to 5 carbon atoms is preferable, a methyl group, an ethyl group, a propyl group, an n-butyl group or a tert-butyl group is more preferable, and a methyl group is particularly desirable.

The alkoxy group as a substituent is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom for the substituent include a fluorine atom, a chlorine atom, a bromine atom and an iodine atom, and a fluorine atom or a bromine atom is preferable.

Examples of the halogenated alkyl group for the substituent include groups in which part or all of the hydrogen atoms within the aforementioned "alkyl groups for the substituent" has been substituted with the aforementioned halogen atoms.

As the aliphatic hydrocarbon group having a polycyclic group for Y, a monovalent group having a polycyclic group among the "aliphatic hydrocarbon group containing a ring in the structure thereof" for $R^2$ can be given. Specifically, among the groups mentioned above in the explanation of $R^2$, monovalent groups such as a group in which one hydrogen atom has been removed from an alicyclic hydrocarbon group (aliphatic hydrocarbon ring), a group in which an alicyclic hydrocarbon group is bonded to a terminal of a linear or branched aliphatic hydrocarbon group, and a group in which an alicyclic hydrocarbon group is interposed within a linear or branched aliphatic hydrocarbon group can be given.

Among these, as the aliphatic hydrocarbon group having a polycyclic group for Y, a group in which one hydrogen atom has been removed from an alicyclic hydrocarbon group (aliphatic hydrocarbon ring) or a group in which an alicyclic hydrocarbon group is bonded to a terminal of a linear or branched aliphatic hydrocarbon group is preferable. In such a case, as the alicyclic hydrocarbon group, a group in which one hydrogen atom has been removed from a polycycloalkane is preferable, and the polycyclic group preferably has 3 to 20 carbon atoms, more preferably 7 to 12 carbon atoms. Specific examples include adamantane, norbornane, isobornane, tricyclodecane and tetracyclododecane.

The aliphatic hydrocarbon group having a polycyclic group for Y may have a carbon atom or a hydrogen atom thereof substituted with a substituent. The substituent includes atoms and atomic groups.

As an example of the aromatic hydrocarbon group in which a carbon atom has been substituted with a substituent, an aromatic heterocyclic group in which part of carbon atoms constituting an aromatic hydrocarbon ring has been substituted with a hetero atom can be mentioned. Examples of the hetero atom within the hetero rings include an oxygen atom, a sulfur atom and a nitrogen atom.

In the case where a hydrogen atom of the aliphatic hydrocarbon group is substituted with a substituent, examples of the substituent include an alkyl group of 1 to 5 carbon atoms, a fluorine atom, a fluorinated alkyl group of 1 to 5 carbon atoms, and an oxygen atom (=O).

In terms of obtaining excellent lithography properties, as the structural unit (a5), a structural unit represented by general formula (a5-1) or (a5-2) shown below is preferable.

[Chemical Formula 5]

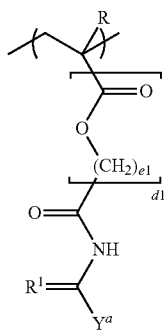

(a5-1)

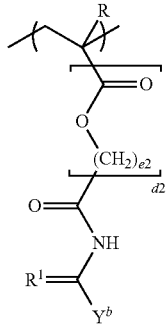

(a5-2)

In the formula, R represents a hydrogen atom, an alkyl group of 1 to 5 carbon atoms or a halogenated alkyl group of 1 to 5 carbon atoms; $R^1$ represents a sulfur atom or an oxygen atom; $Y^a$ represents an aromatic hydrocarbon group (the aromatic hydrocarbon group may have a carbon atom or a hydrogen atom thereof substituted with a substituent); $Y^b$ represents an aliphatic hydrocarbon group having a polycyclic group (the aliphatic hydrocarbon group may have a carbon atom or a hydrogen atom thereof substituted with a substituent); each of d1 and d2 independently represents 0 or 1; and each of e1 and e2 independently represent an integer of 1 to 5.

In the formulae (a5-1) and (a5-2), R is the same as defined for R in the aforementioned formula (a5-0). $R^1$ represents a sulfur atom or an oxygen atom, and an oxygen atom is preferable.

In the formula (a5-1), $Y^a$ is the same as defined for the aromatic hydrocarbon group for Y in the aforementioned formula (a5-0). As $Y^a$, a group in which one hydrogen atom has been removed from an aromatic ring (aromatic hydrocarbon ring) is preferable, and a phenyl group or a naphthyl group is particularly desirable.

The aromatic hydrocarbon group for $Y^a$ preferably has a hydrogen atom thereof substituted with a substituent, and more preferably a hydrogen atom is substituted with a halogen atom. The halogen atom is preferably a fluorine atom or a bromine atom.

In the formula (a5-2), $Y^b$ is the same as defined for the aliphatic hydrocarbon group having a polycyclic group for Y in the aforementioned formula (a5-0). As $Y^b$, a group in which one hydrogen atom has been removed from an alicyclic hydrocarbon group (aliphatic hydrocarbon ring) or a group in which an alicyclic hydrocarbon group is bonded to a terminal of a linear or branched aliphatic hydrocarbon group is preferable.

Specific examples of the structural units represented by general formulae a5-1) and (a5-2) are shown below.

In the formulae shown below, $R^\alpha$ represents a hydrogen atom, a methyl group or a trifluoromethyl group.

[Chemical Formula 6]

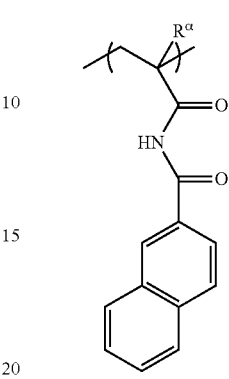

(a5-1-1)

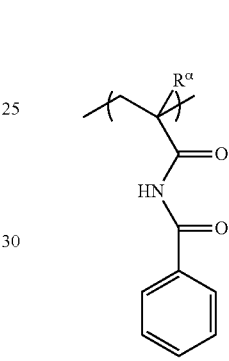

(a5-1-2)

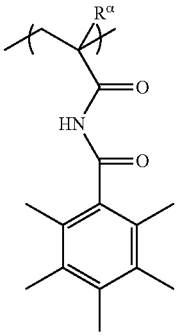

(a5-1-3)

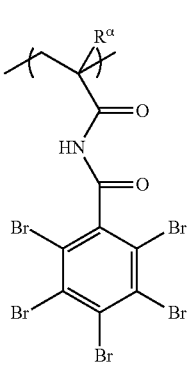

(a5-1-4)

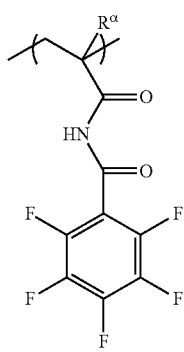 (a5-1-5)
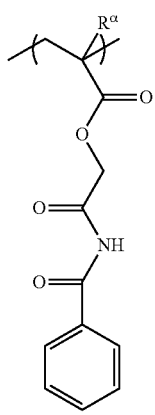 (a5-1-6)
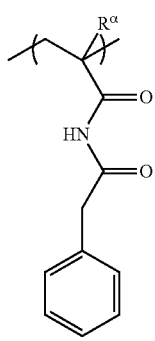 (a5-1-7)
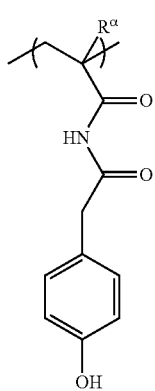 (a5-1-8)
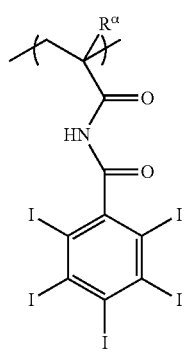 (a5-1-9)
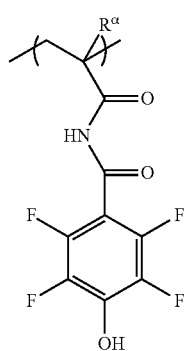 (a5-1-10)
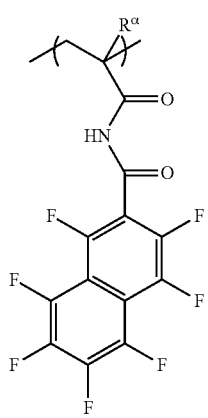 (a5-1-11)
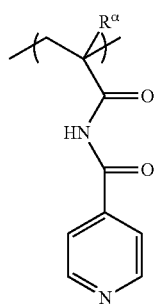 (a5-1-12)

(a5-1-13)
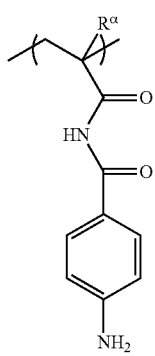
(a5-1-14)
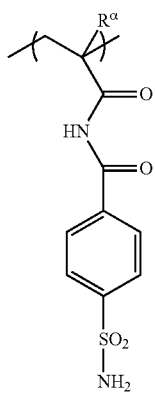
[Chemical Formula 7]
(a5-2-1)
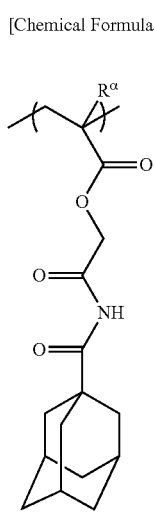
(a5-2-2)
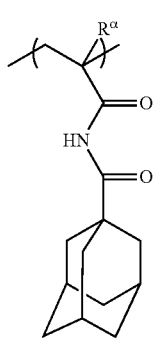
(a5-2-3)
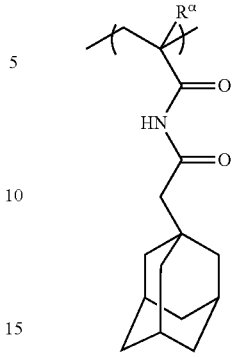
(a5-2-4)
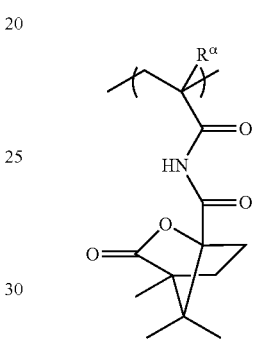
(a5-2-5)
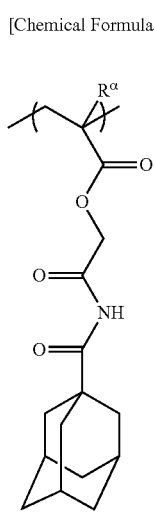
(a5-2-6)
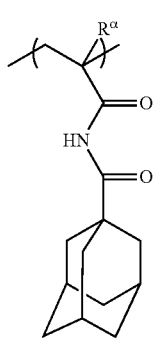

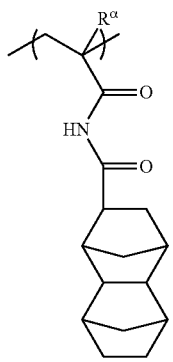

(a5-2-7)

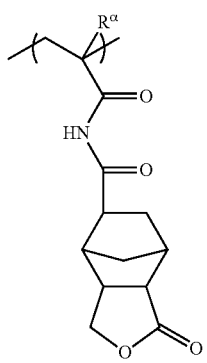

(a5-2-8)

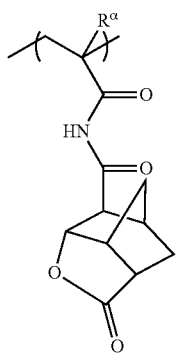

(a5-2-9)

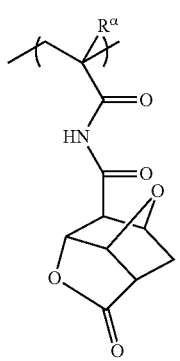

(a5-2-10)

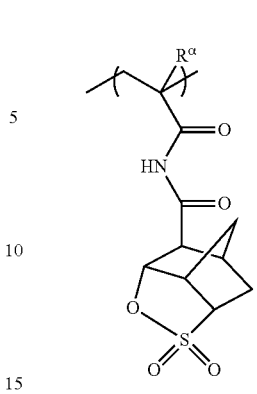

(a5-2-11)

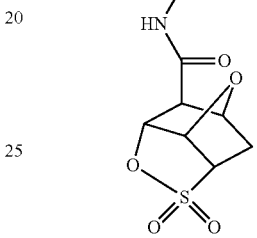

(a5-2-12)

As the structural unit (a5), at least one member selected from the group consisting of a structural unit represented by general formula (a5-1) and a structural unit represented by general formula (a5-2) is preferable.

Among these, at least one member selected from the group consisting of a structural unit represented by any one of formulae (a5-1-1) to (a5-1-5) and a structural unit represented by any one of formulae (a5-2-1) to (a5-2-4) is more preferable.

In the component (A1-1), as the structural unit (a5), one type of structural unit may be used alone, or two or more types of structural units may be used in combination.

In the component (A1-1), the amount of the structural unit (a5) based on the combined total of all structural units constituting the component (A1-1) is preferably 5 to 95 mol %, more preferably 5 to 80 mol %, still more preferably 10 to 70 mol %, and most preferably 10 to 65 mol %.

When the amount of the structural unit (a5) is at least as large as the lower limit of the above-mentioned range, sensitivity, resolution and lithography properties can be more reliably improved. On the other hand, when the amount of the structural unit (a5) is no more than the upper limit of the above-mentioned range, a good balance can be reliably achieved with the other structural units.

Structural Unit (a1)

In the present invention, the structural unit (a1) is a structural unit containing an acid decomposable group that exhibits increased polarity by the action of acid.

In the structural unit (a1), the term "acid decomposable group" refers to a group in which at least a part of the bond within the structure thereof is cleaved by the action of an acid.

Examples of acid decomposable groups which exhibit increased polarity by the action of an acid include groups which are decomposed by the action of an acid to form a polar group.

Examples of the polar group include a carboxy group, a hydroxy group, an amino group and a sulfo group ($-SO_3H$).

Among these, a polar group containing —OH in the structure thereof (hereafter, referred to as "OH-containing polar group") is preferable, a carboxy group or a hydroxy group is more preferable, and a carboxy group is particularly desirable.

More specifically, as an example of an acid decomposable group, a group in which the aforementioned polar group has been protected with an acid dissociable group (such as a group in which the hydrogen atom of the OH-containing polar group has been protected with an acid dissociable group) can be given.

An "acid dissociable group" is a group in which at least the bond between the acid dissociable group and the adjacent carbon atom is cleaved by the action of acid. It is necessary that the acid dissociable group that constitutes the acid decomposable group is a group which exhibits a lower polarity than the polar group generated by the dissociation of the acid dissociable group. Thus, when the acid dissociable group is dissociated by the action of acid, a polar group exhibiting a higher polarity than that of the acid dissociable group is generated, thereby increasing the polarity. As a result, the polarity of the entire component (A1-1) is increased. By the increase in the polarity, the solubility in an alkali developing solution changes and, the solubility in an alkali developing solution is relatively increased, whereas the solubility in a developing solution containing an organic solvent (organic solvent) is relatively decreased.

The acid dissociable group is not particularly limited, and any of the groups that have been conventionally proposed as acid dissociable groups for the base resins of chemically amplified resists can be used. Generally, groups that form either a cyclic or chain-like tertiary alkyl ester with the carboxyl group of the (meth)acrylic acid, and acetal-type acid dissociable groups such as alkoxyalkyl groups are widely known.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(=O)—O—). In this tertiary alkyl ester, the action of acid causes cleavage of the bond between the oxygen atom and the tertiary carbon atom, thereby forming a carboxy group.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable groups".

Examples of tertiary alkyl ester-type acid dissociable groups include aliphatic branched, acid dissociable groups and aliphatic cyclic group-containing acid dissociable groups.

The term "aliphatic branched" refers to a branched structure having no aromaticity. The "aliphatic branched, acid dissociable group" is not limited to be constituted of only carbon atoms and hydrogen atoms (not limited to hydrocarbon groups), but is preferably a hydrocarbon group. Further, the "hydrocarbon group" may be either saturated or unsaturated, but is preferably saturated.

As an example of the aliphatic branched, acid dissociable group, for example, a group represented by the formula —C($R^{71}$)($R^{72}$)($R^{73}$) can be given (in the formula, each of $R^{71}$ to $R^{73}$ independently represents a linear alkyl group of 1 to 5 carbon atoms). The group represented by the formula —C($R^{71}$)($R^{72}$)($R^{73}$) preferably has 4 to 8 carbon atoms, and specific examples include a tert-butyl group, a 2-methyl-2-butyl group, a 2-methyl-2-pentyl group and a 3-methyl-3-pentyl group.

Among these, a tert-butyl group is particularly desirable.

The term "aliphatic cyclic group" refers to a monocyclic group or polycyclic group that has no aromaticity.

In the "aliphatic cyclic group-containing acid dissociable group", the "aliphatic cyclic group" may or may not have a substituent. Examples of the substituent include an alkyl group of 1 to 5 carbon atoms, an alkoxy group of 1 to 5 carbon atoms, a fluorine atom, a fluorinated alkyl group of 1 to 5 carbon atoms, and an oxygen atom (=O).

The basic ring of the "aliphatic cyclic group" exclusive of substituents is not limited to be constituted from only carbon and hydrogen (not limited to hydrocarbon groups), but is preferably a hydrocarbon group. Further, the "hydrocarbon group" may be either saturated or unsaturated, but is preferably saturated.

The aliphatic cyclic group may be either a monocyclic group or a polycyclic group.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with a lower alkyl group, a fluorine atom or a fluorinated alkyl group, may be used. Specific examples of aliphatic cyclic hydrocarbon groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane. In these aliphatic cyclic hydrocarbon groups, part of the carbon atoms constituting the ring may be replaced with an ethereal oxygen atom (—O—).

Examples of aliphatic cyclic group-containing acid dissociable groups include (i) a monovalent aliphatic cyclic group in which a substituent (a group or an atom other than hydrogen) is bonded to the carbon atom on the ring skeleton to which an atom adjacent to the acid dissociable group (e.g., "—O—" within "—C(=O)—O— group") is bonded to form a tertiary carbon atom; and (ii) a group which has a branched alkylene group containing a tertiary carbon atom, and a monovalent aliphatic cyclic group to which the tertiary carbon atom is bonded.

In the group (i), as the substituent bonded to the carbon atom to which an atom adjacent to the acid dissociable group on the ring skeleton of the aliphatic cyclic group, an alkyl group can be mentioned. Examples of the alkyl group include the same groups as those represented by $R^{14}$ in formulas (1-1) to (1-9) described later.

Specific examples of the group (i) include groups represented by general formulas (1-1) to (1-9) shown below.

Specific examples of the group (ii) include groups represented by general formulas (2-1) to (2-6) shown below.

[Chemical Formula 8]

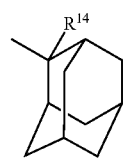

(1-1)

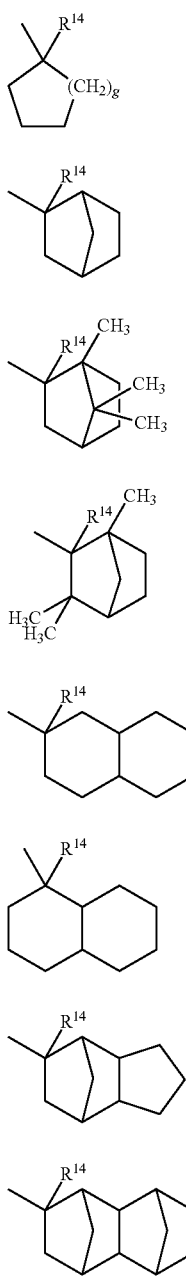

In the formulas above, R[14] represents an alkyl group; and g represents an integer of 0 to 8.

[Chemical Formula 9]

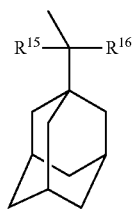

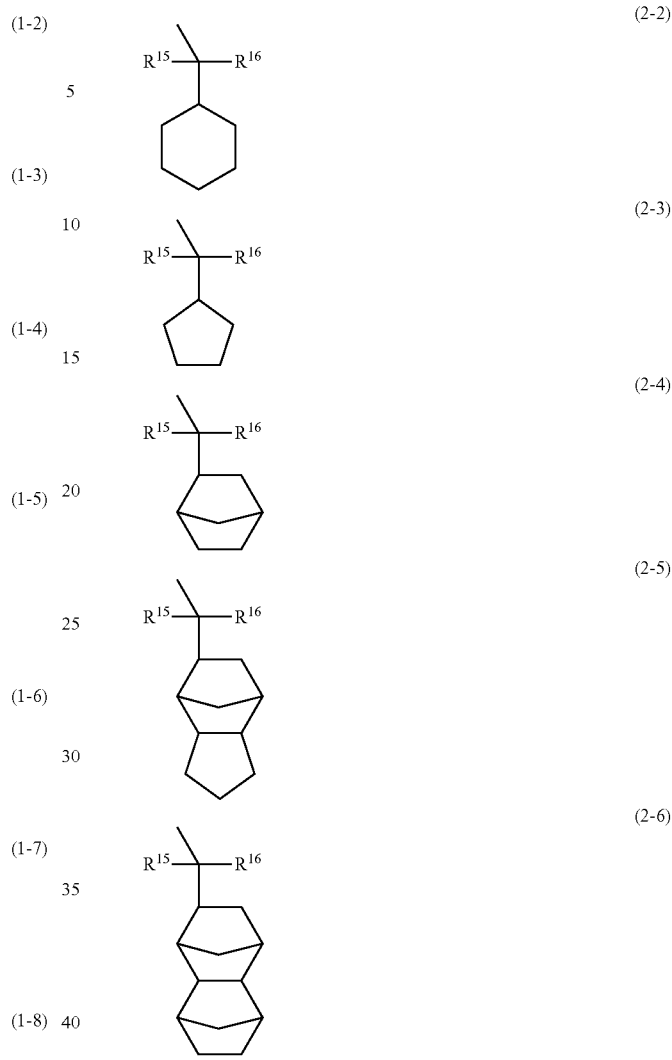

In the formulas above, each of R[15] and R[16] independently represents an alkyl group.

In formulas (1-1) to (1-9), the alkyl group for R[14] may be linear, branched or cyclic, and is preferably linear or branched.

The linear alkyl group preferably has 1 to 5 carbon atoms, more preferably 1 to 4, and still more preferably 1 or 2. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group preferably has 3 to 10 carbon atoms, and more preferably 3 to 5. Specific examples of such branched alkyl groups include an isopropyl group, an isobutyl group, a tert-butyl group, an isopentyl group and a neopentyl group, and an isopropyl group is particularly desirable.

g is preferably an integer of 0 to 3, more preferably 1 to 3, and still more preferably 1 or 2.

In formulas (2-1) to (2-6), as the alkyl group for R[15] and R[16], the same alkyl groups as those for R[14] can be used.

In formulas (1-1) to (1-9) and (2-1) to (2-6), part of the carbon atoms constituting the ring may be replaced with an ethereal oxygen atom (—O—).

Further, in formulas (1-1) to (1-9) and (2-1) to (2-6), one or more of the hydrogen atoms bonded to the carbon atoms constituting the ring may be substituted with a substituent. Examples of the substituent include an alkyl group of 1 to 5 carbon atoms, a fluorine atom and a fluorinated alkyl group.

An "acetal-type acid dissociable group" generally substitutes a hydrogen atom at the terminal of an OH-containing polar group such as a carboxy group or hydroxyl group, so as to be bonded with an oxygen atom. When acid acts to break the bond between the acetal-type acid dissociable group and the oxygen atom to which the acetal-type, acid dissociable group is bonded, an OH-containing polar group such as a carboxy group or a hydroxy group is formed.

Examples of acetal-type acid dissociable groups include groups represented by general formula (p1) shown below.

[Chemical Formula 10]

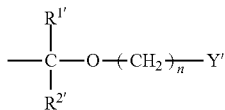

(p 1)

In the formula, $R^{1\prime}$ and $R^{2\prime}$ each independently represent a hydrogen atom or an alkyl group of 1 to 5 carbon atoms; n represents an integer of 0 to 3; and Y' represents an alkyl group of 1 to 5 carbon atoms or an aliphatic cyclic group.

In general formula (p1), n is preferably an integer of 0 to 2, more preferably 0 or 1, and most preferably 0.

Examples of the alkyl group for $R^{1\prime}$ and $R^{2\prime}$ include linear or branched alkyl groups such as a methyl group, an ethyl group, a propyl group, an isopropyl group, an n-butyl group, an isobutyl group, a tert-butyl group, a pentyl group, an isopentyl group and a neopentyl group. Of these, a methyl group or an ethyl group is preferable, and a methyl group is most preferable.

In the present invention, it is preferable that at least one of $R^{1\prime}$ and $R^{2\prime}$ be a hydrogen atom. That is, it is preferable that the acid dissociable group (p1) is a group represented by general formula (p1-1) shown below.

[Chemical Formula 11]

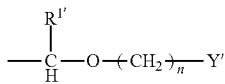

(p 1-1)

In the formula, $R^{1\prime}$, n and Y' are the same as defined above.

Examples of the alkyl group for Y' include linear or branched alkyl groups such as a methyl group, an ethyl group, a propyl group, an isopropyl group, an n-butyl group, an isobutyl group, a tert-butyl group, a pentyl group, an isopentyl group and a neopentyl group.

As the aliphatic cyclic group for Y', any of the aliphatic monocyclic/polycyclic groups which have been proposed for conventional ArF resists and the like can be appropriately selected for use. For example, the same aliphatic cyclic groups described above in connection with the "acid dissociable group containing an aliphatic cyclic group" can be used.

Further, as the acetal-type, acid dissociable group, groups represented by general formula (p2) shown below can also be used.

[Chemical Formula 12]

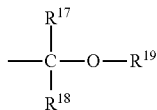

(p 2)

In the formula, $R^{17}$ and $R^{18}$ each independently represent a linear or branched alkyl group or a hydrogen atom; and $R^{19}$ represents a linear, branched or cyclic alkyl group; or $R^{17}$ and $R^{19}$ each independently represents a linear or branched alkylene group, and the terminal of $R^{17}$ is bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable.

It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably a methyl group or an ethyl group, and most preferably an ethyl group.

When $R^{19}$ represents a cycloalkyl group, it preferably has 4 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane. Among these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto, and the carbon atom having the oxygen atom and $R^{17}$ bonded thereto. Such a cyclic group is preferably a 4- to 7-membered ring, and more preferably a 4- to 6-membered ring. Specific examples of the cyclic group include tetrahydropyranyl group and tetrahydrofuranyl group.

With respect to the structural unit (a1), there is not particular limitation to the structure of the other portion, as long as the structural unit has an acid decomposable group. Preferable examples of the structural unit (a1) include a structural unit (a11) derived from an acrylate ester having an acid decomposable group and which may have the hydrogen atom bonded to the carbon atom on the α-position substituted with a substituent; a structural unit (a12) derived from hydroxystyrene in which the hydrogen atom of the hydroxy group has been substituted with an acid dissociable group or a substituent containing an acid dissociable group, wherein the hydrogen atom bonded to the carbon atom on the α-position may be substituted with a substituent, and a hydrogen atom bonded to the benzene ring may be substituted with a substituent other than a hydroxy group; and a structural unit (a13) derived from vinyl(hydroxynaphthalene) in which the hydrogen atom of the hydroxy group has been substituted with an acid dissociable group or a substituent containing an acid dissociable group, wherein the hydrogen atom bonded to the carbon atom on the α-position may be substituted with a substituent, and a hydrogen atom bonded to the naphthalene ring may be substituted with a substituent other than a hydroxy group.

Among these, in terms of improving roughness (reducing line width roughness and line edge roughness), a structural unit (a11) is preferable, and in terms of suppressing absorption of the exposure light, a structural unit (a12) or a structural unit (a13) is preferable.

In the present description, the expression "structural unit derived from an acrylate ester" refers to a structural unit that is formed by the cleavage of the ethylenic double bond of an acrylate ester.

An "acrylate ester" refers to a compound in which the terminal hydrogen atom of the carboxy group of acrylic acid ($CH_2$=CH—COOH) has been substituted with an organic group.

The acrylate ester may have the hydrogen atom bonded to the carbon atom on the α-position substituted with a substituent. The substituent that substitutes the hydrogen atom bonded to the carbon atom on the α-position is atom other than hydrogen or a group, and examples thereof include an alkyl group of 1 to 5 carbon atoms, a halogenated alkyl group of 1 to 5 carbon atoms and a hydroxyalkyl group. A carbon atom on the α-position of an acrylate ester refers to the carbon atom bonded to the carbonyl group, unless specified otherwise.

Hereafter, acrylic acid or an acrylate ester having the hydrogen atom bonded to the carbon atom on the α-position substituted with a substituent is sometimes referred to as "α-substituted acrylic acid" or "α-substituted acrylate ester". Further, acrylic acid and α-substituted acrylic acid are collectively referred to as "(α-substituted) acrylic acid", and acrylate esters and α-substituted acrylate esters are collectively referred to as "(α-substituted) acrylate ester".

In the α-substituted acrylate ester, the "alkyl group as the substituent on the α-position" is preferably a linear or branched alkyl group, and specific examples thereof include a methyl group, an ethyl group, a propyl group, an isopropyl group, an n-butyl group, an isobutyl group, a tert-butyl group, a pentyl group, an isopentyl group and a neopentyl group.

Specific examples of the halogenated alkyl group of 1 to 5 carbon atoms as the substituent on the α-position include groups in which part or all of the hydrogen atoms of the aforementioned "alkyl group of 1 to 5 carbon atoms as the substituent on the α-position" are substituted with halogen atoms. Examples of the halogen atom include a fluorine atom, a chlorine atom, a bromine atom and an iodine atom, and a fluorine atom is particularly desirable.

It is preferable that a hydrogen atom, an alkyl group of 1 to 5 carbon atoms or a halogenated alkyl group of 1 to 5 carbon atoms is bonded to the α-position of the α-substituted acrylate ester, a hydrogen atom, an alkyl group of 1 to 5 carbon atoms or a fluorinated alkyl group of 1 to 5 carbon atoms is more preferable, and in terms of industrial availability, a hydrogen atom or a methyl group is the most desirable.

A "structural unit derived from a hydroxystyrene" refers to a structural unit that is formed by the cleavage of the ethylenic double bond of a hydroxystyrene.

A hydroxystyrene is a compound which has 1 vinyl group and at least 1 hydroxy group bonded to a benzene ring. The number of hydroxy groups bonded to the benzene ring is preferably 1 to 3, and most preferably 1. The bonding position of the hydroxy group on the benzene ring is not particularly limited. When there is 1 hydroxy group, a para-4th position from the bonding position of the vinyl group is preferable. When there are 2 or more hydroxy groups, a desired combination of the bonding positions can be used.

A "structural unit derived from a vinyl(hydroxynaphthalene)" refers to a structural unit that is formed by the cleavage of the ethylenic double bond of a vinyl(hydroxynaphthalene).

A vinyl(hydroxynaphthalene) is a compound which has 1 vinyl group and at least 1 hydroxy group bonded to a naphthalene ring. The vinyl group may be bonded to the 1st or 2nd position of the naphthalene ring. The number of hydroxy groups bonded to the naphthalene ring is preferably 1 to 3, and most preferably 1. The bonding position of the hydroxy group on the naphthalene ring is not particularly limited. When the vinyl group is bonded to the 1st or 2nd position of the naphthalene ring, the hydroxy group is preferably bonded to either one of the 5th to 8th position of the naphthalene ring. In particular, when the number of hydroxy group is 1, the hydroxy group is preferably bonded to either one of the 5th to 7th position of the naphthalene ring, and more preferably the 5th or 6th position. When there are 2 or more hydroxy groups, a desired combination of the bonding positions can be used.

(Structural Unit (a11)):

The structural unit (a11) is a structural unit derived from an acrylate ester having an acid decomposable group and which may have the hydrogen atom bonded to the carbon atom on the α-position substituted with a substituent.

Examples of the structural unit (a11) include a structural unit represented by general formula (a1-0-1) shown below and a structural unit represented by general formula (a1-0-2) shown below.

[Chemical Formula 13]

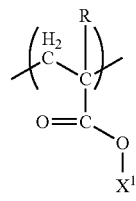

(a1-0-1)

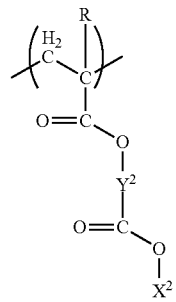

(a1-0-2)

In the formulas, R represents a hydrogen atom, an alkyl group of 1 to 5 carbon atoms or a halogenated alkyl group of 1 to 5 carbon atoms; $X^1$ represents an acid dissociable group; $Y^2$ represents a divalent linking group; and $X^2$ represents an acid dissociable group.

In general formula (a1-0-1), examples of the alkyl group of 1 to 5 carbon atoms for R include linear or branched alkyl groups such as a methyl group, an ethyl group, a propyl group, an isopropyl group, an n-butyl group, an isobutyl group, a tert-butyl group, a pentyl group, an isopentyl group and a neopentyl group.

Examples of the halogenated alkyl group of 1 to 5 carbon atoms for R include groups in which part or all of the hydrogen atoms of the aforementioned alkyl groups of 1 to 5 carbon atoms have been substituted with halogen atoms. Examples of the halogen atom include a fluorine atom, a chlorine atom, a bromine atom and an iodine atom, and a fluorine atom is particularly desirable.

R is preferably a hydrogen atom, an alkyl group of 1 to 5 carbon atoms or a fluorinated alkyl group of 1 to 5 carbon atoms, and most preferably a hydrogen atom or a methyl group.

$X^1$ is not particularly limited as long as it is an acid dissociable group. Examples thereof include the aforementioned tertiary alkyl ester-type acid dissociable groups and acetal-type acid dissociable groups, and tertiary alkyl ester-type acid dissociable groups are preferable.

In general formula (a1-0-2), R is the same as defined above.

$X^2$ is the same as defined for $X^1$ in general formula (a1-0-1).

The divalent linking group for $Y^2$ is not particularly limited, and preferable examples thereof include a divalent hydrocarbon group which may have a substituent and a divalent linking group containing a hetero atom.

Examples of the divalent linking group for $Y^2$ include the same divalent linking groups as those described above for $R^2$ in the aforementioned formula (a5-0).

Among these, as $Y^2$, a linear or branched alkylene group or a divalent linking group containing a hetero atom is preferable, and a linear or branched alkylene group, a group represented by the aforementioned formula —$Y^{21}$—O—$Y^{22}$—, a group represented by the aforementioned formula —[$Y^{21}$—C(=O)—O]$_m$—$Y^{22}$—, or a group represented by the aforementioned formula —$Y^{21}$—O—C(=O)—$Y^{22}$— is more preferable.

Specific examples of the structural unit (a11) include structural units represented by general formulas (a1-1) to (a1-4) shown below.

[Chemical Formula 14]

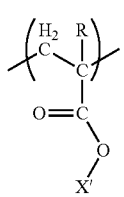
(a1-1)

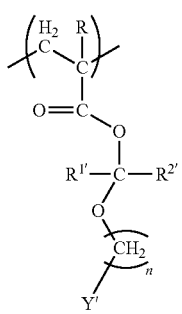
(a1-2)

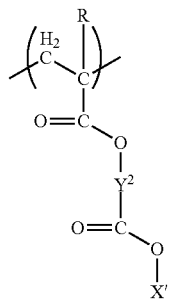
(a1-3)

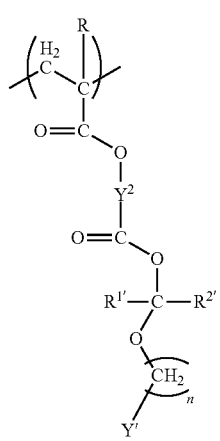
(a1-4)

In the formulas, R, $R^{1'}$, $R^{2'}$, n, Y' and $Y^2$ are the same as defined above; and X' represents a tertiary alkyl ester-type acid dissociable group.

In the formulas, the tertiary alkyl ester-type acid dissociable group for X' include the same tertiary alkyl ester-type acid dissociable groups as those described above.

As $R^{1'}$, n and Y' are respectively the same as defined for $R^{1'}$, n and Y' in general formula (p1) described above in connection with the "acetal-type acid dissociable group".

As examples of $Y^2$, the same groups as those described above for $Y^2$ in general formula (a1-0-2) can be given.

Specific examples of structural units represented by general formula (a1-1) to (a1-4) are shown below.

In the formulas shown below, $R^\alpha$ represents a hydrogen atom, a methyl group or a trifluoromethyl group.

[Chemical Formula 15]

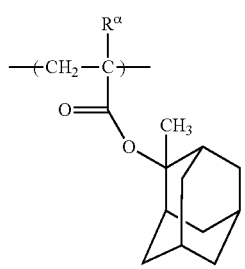
(a1-1-1)

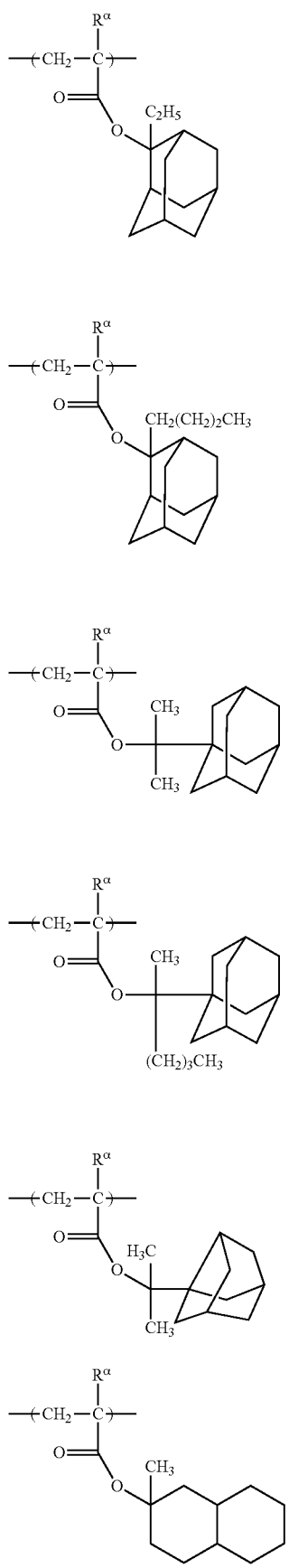
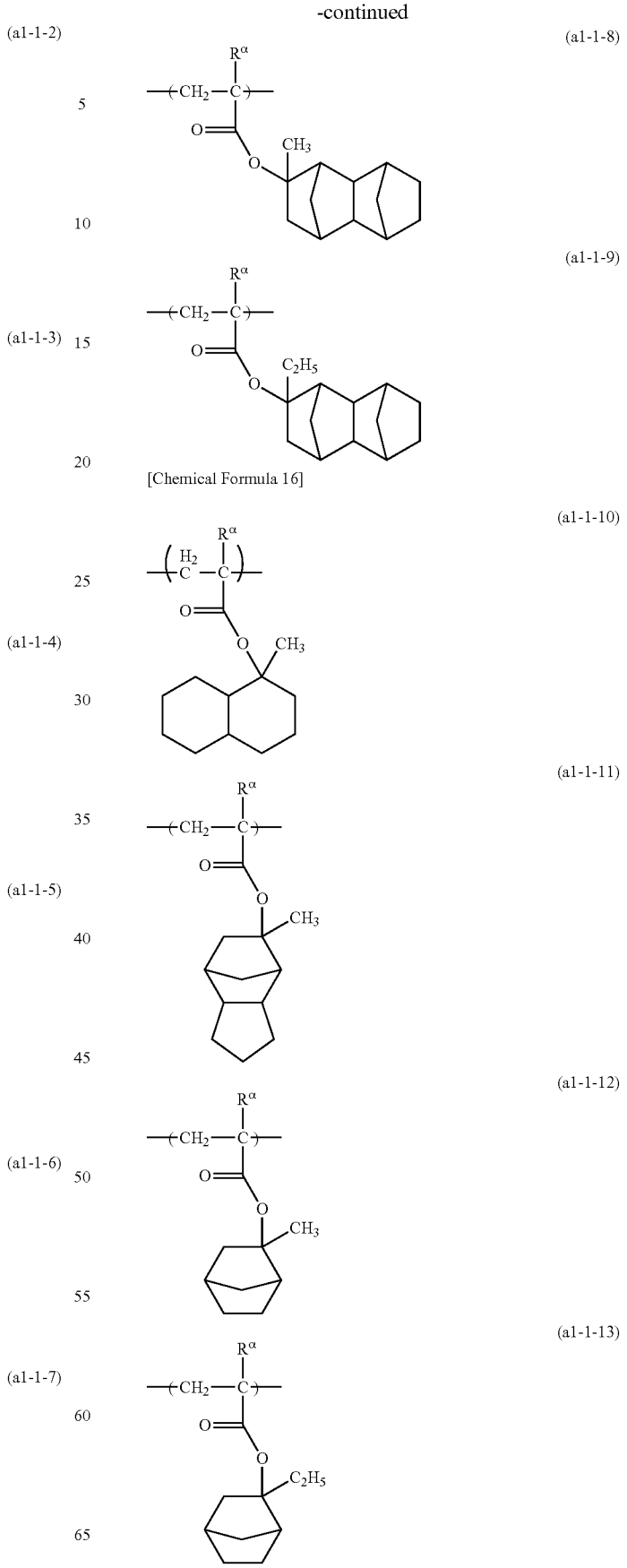

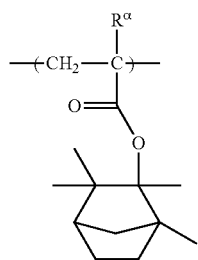 (a1-1-14)
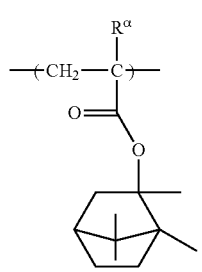 (a1-1-15)
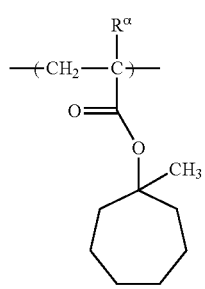 (a1-1-16)
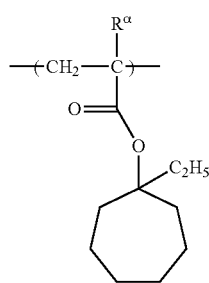 (a1-1-17)
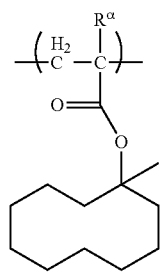 (a1-1-18)
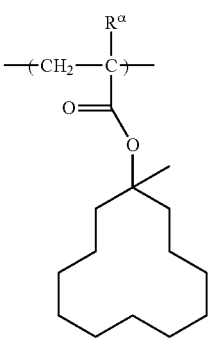 (a1-1-19)
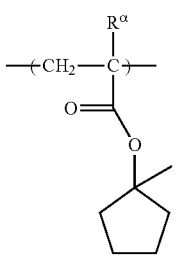 (a1-1-20)
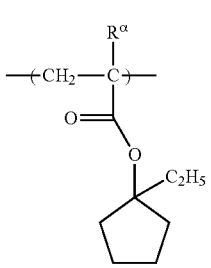 (a1-1-21)
[Chemical Formula 17]
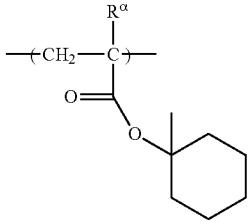 (a1-1-22)
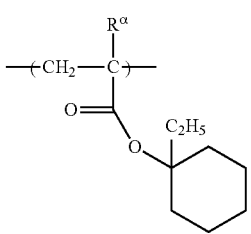 (a1-1-23)
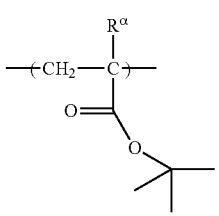 (a1-1-24)

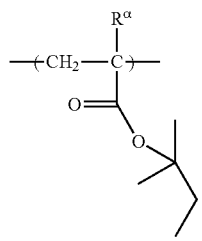
(a1-1-25)
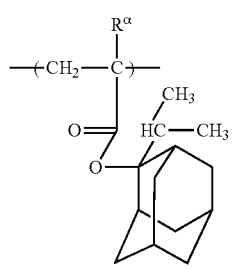
(a1-1-26)
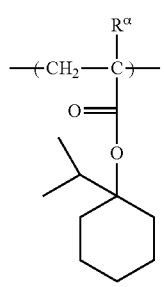
(a1-1-27)
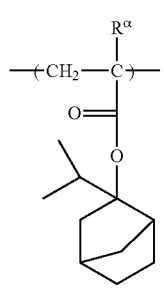
(a1-1-28)
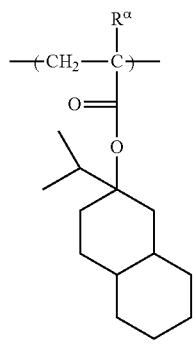
(a1-1-29)
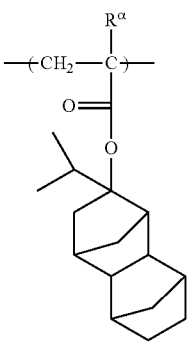
(a1-1-30)
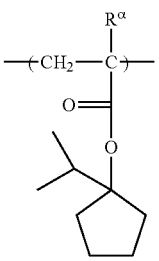
(a1-1-31)
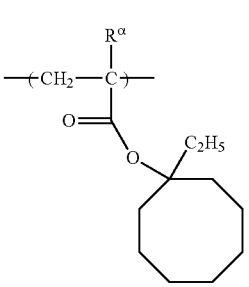
(a1-1-32)
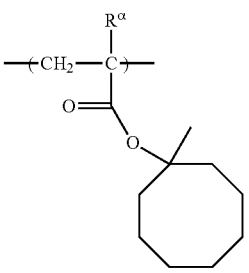
(a1-1-33)
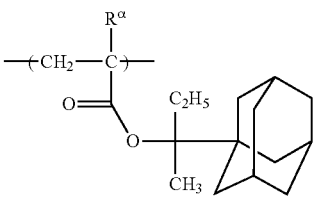
(a1-1-34)
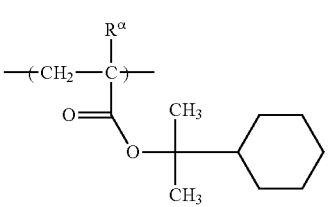
(a1-1-35)

(a1-1-36)
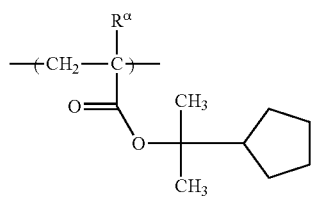
[Chemical Formula 18]
(a1-2-1)
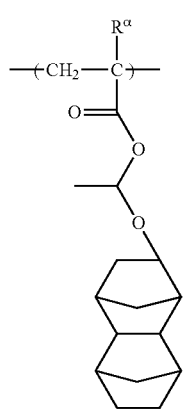
(a1-2-2)
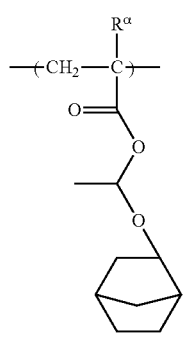
(a1-2-3)
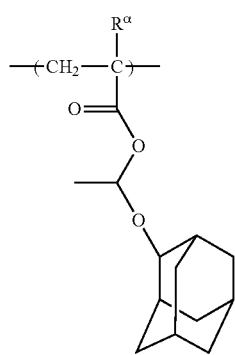
(a1-2-4)
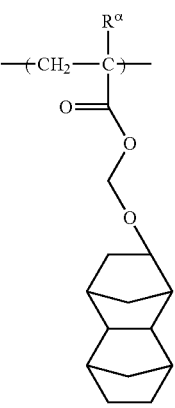
(a1-2-5)
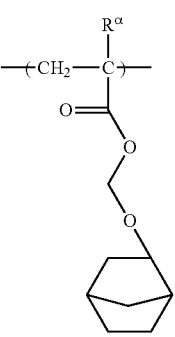
(a1-2-6)
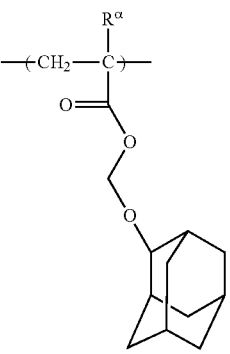
(a1-2-7)
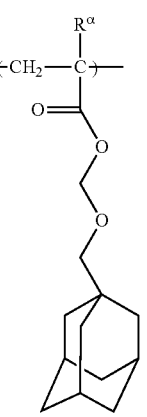

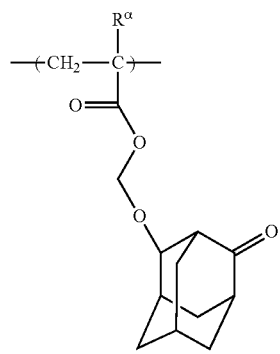 (a1-2-8)
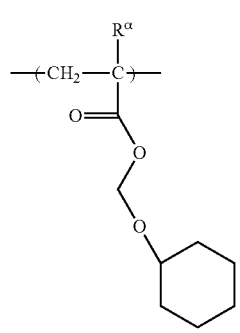 (a1-2-9)
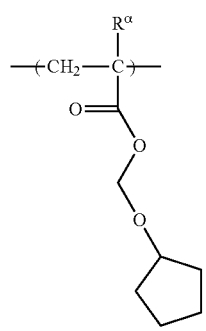 (a1-2-10)
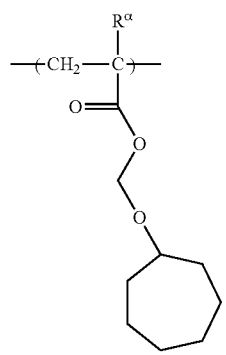 (a1-2-11)
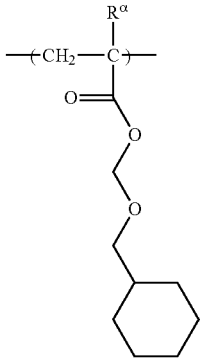 (a1-2-12)
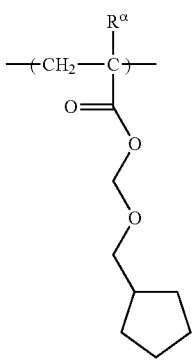 (a1-2-13)
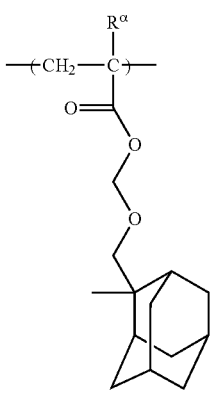 (a1-2-14)
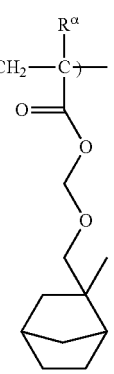 (a1-2-15)

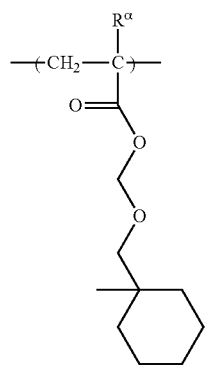 (a1-2-16)
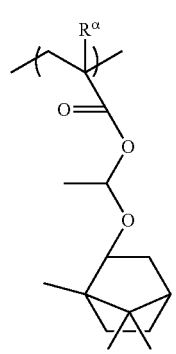 (a1-2-17)
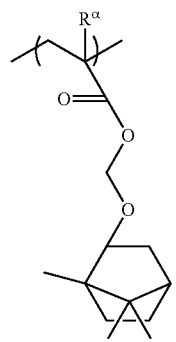 (a1-2-18)
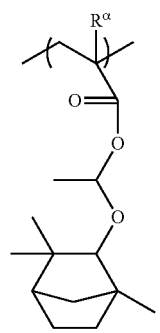 (a1-2-19)
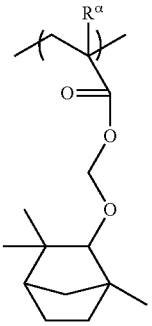 (a1-2-20)
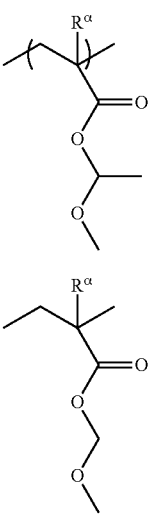 (a1-2-21)
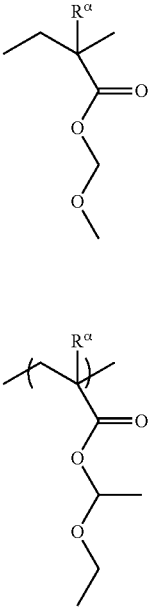 (a1-2-22)
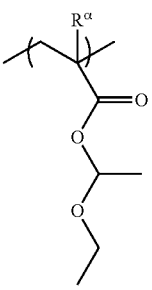 (a1-2-23)
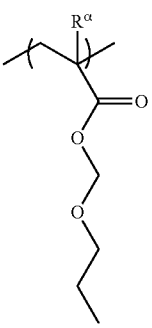 (a1-2-24)

[Chemical Formula 19]
(a1-3-1) 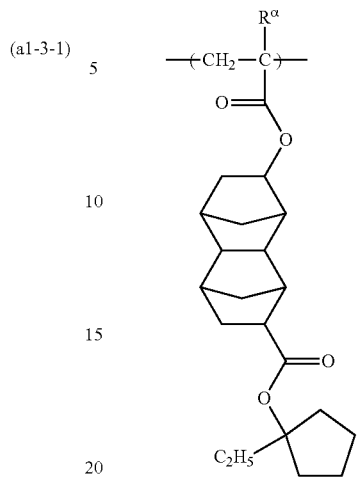
(a1-3-2) 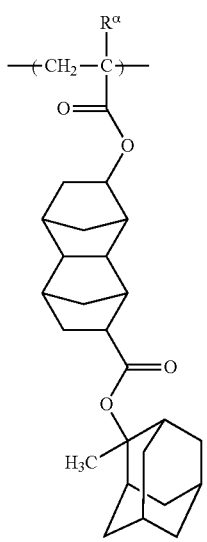
(a1-3-3) 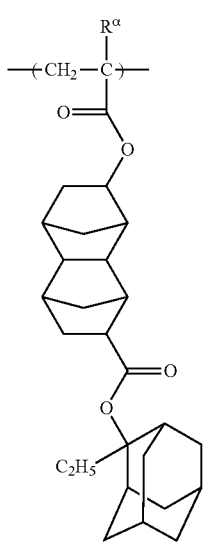
(a1-3-4) 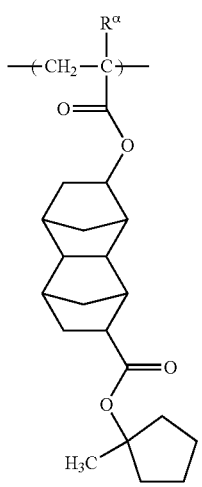
(a1-3-5) 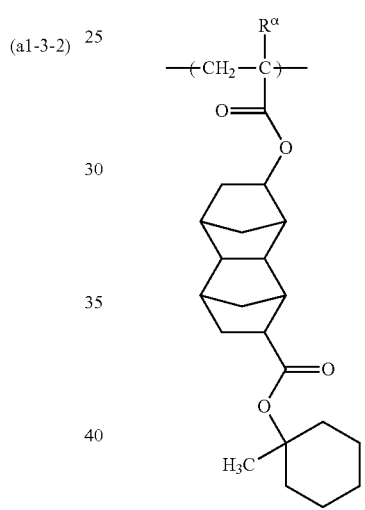
(a1-3-6) 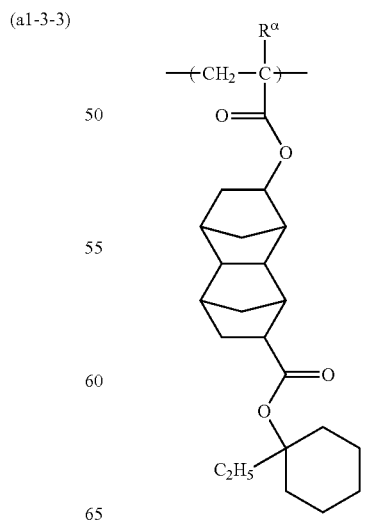

(a1-3-7)
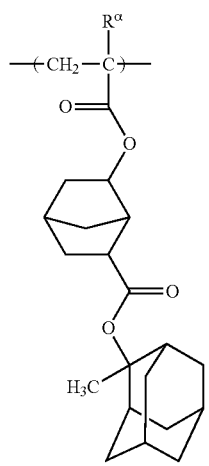
(a1-3-8)
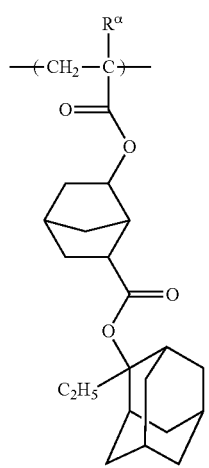
(a1-3-9)
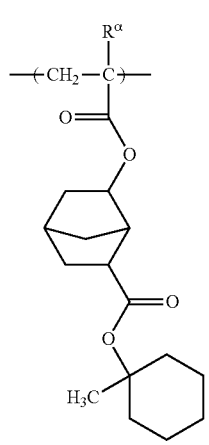
(a1-3-10)
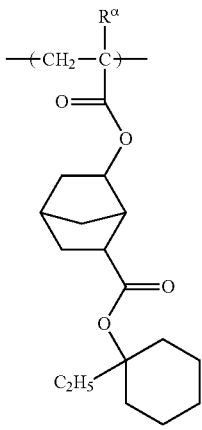
(a1-3-11)
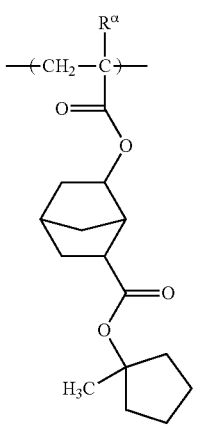
(a1-3-12)
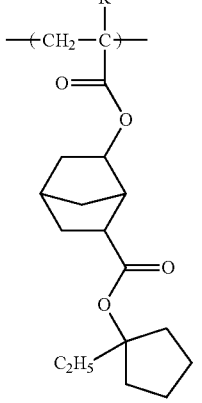
(a1-3-13)
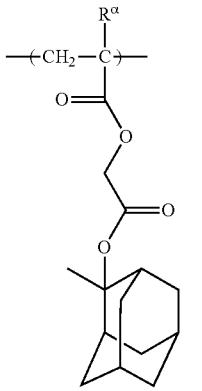

(a1-3-14)
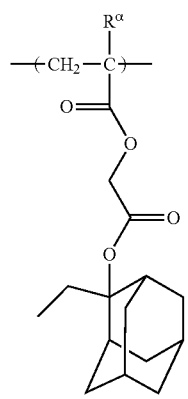
(a1-3-15)
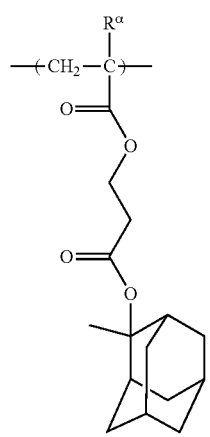
(a1-3-16)
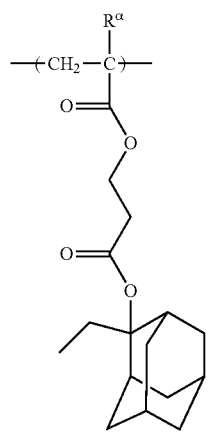
(a1-3-17)
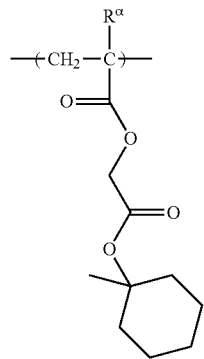
(a1-3-18)
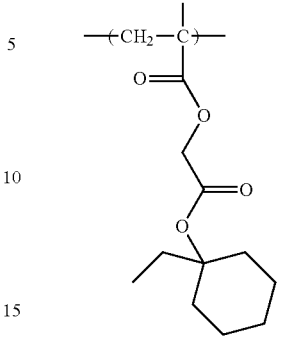
[Chemical Formula 20]
(a1-3-19)
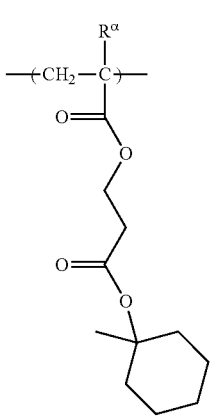
(a1-3-20)
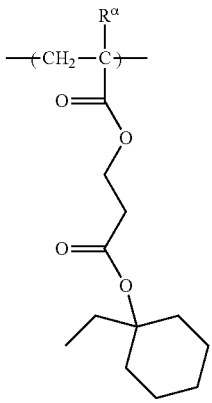
(a1-3-21)
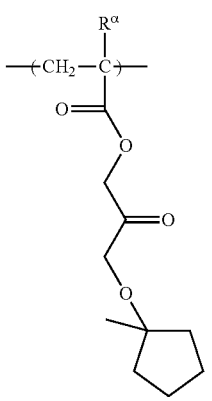

(a1-3-22)
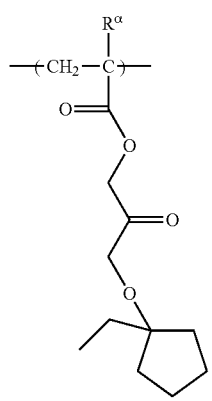
(a1-3-23)
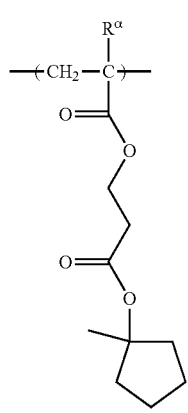
(a1-2-24)
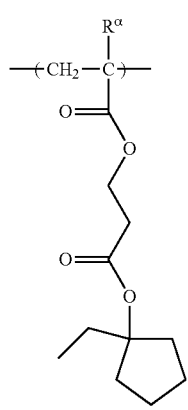
[Chemical Formula 21]
(a1-3-25)
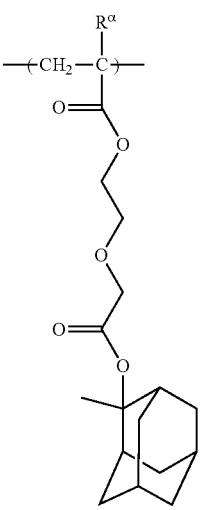
(a1-3-26)
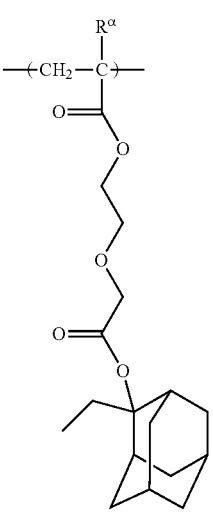
(a1-3-27)
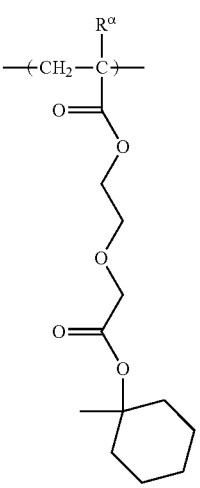

(a1-3-28) 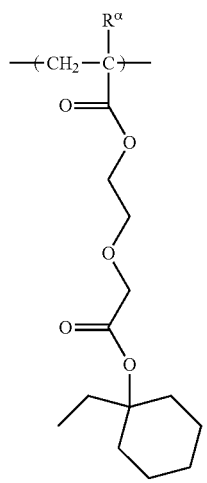
(a1-3-29) 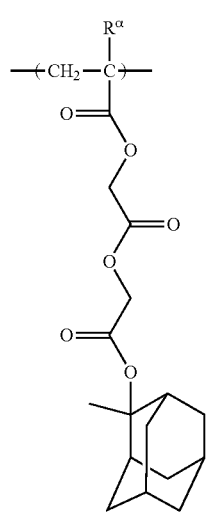
(a1-3-30) 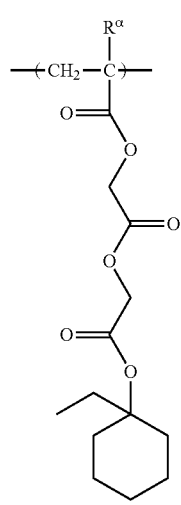
(a1-3-31) 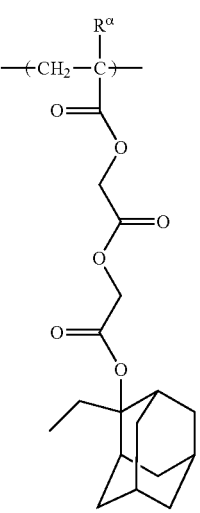
(a1-3-32) 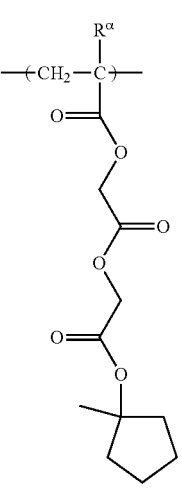
[Chemical Formula 22]
(a1-4-1) 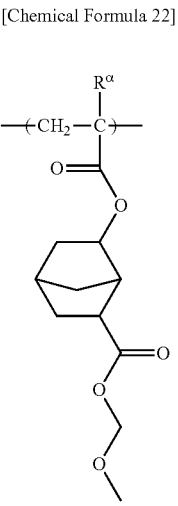

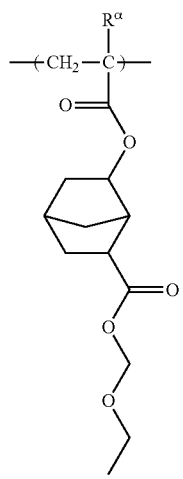
(a1-4-2)
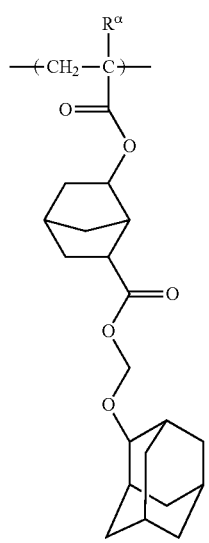
(a1-4-3)
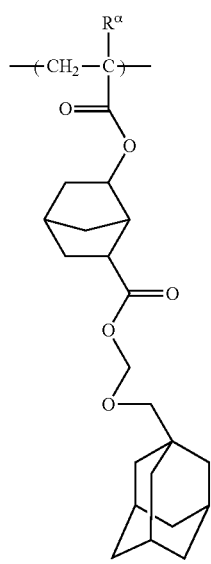
(a1-4-3)
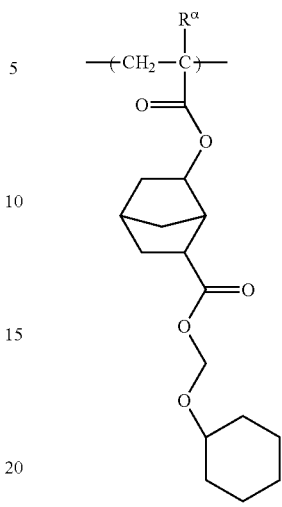
(a1-4-5)
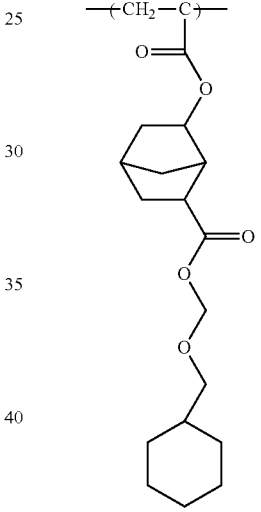
(a1-4-6)
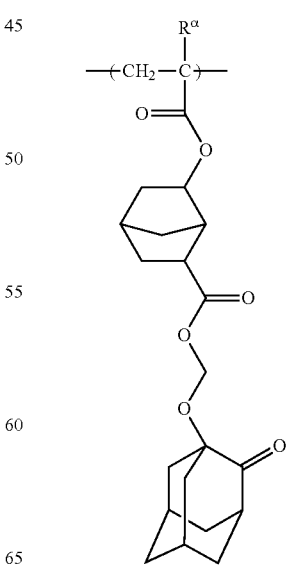
(a1-4-7)

(a1-4-8) 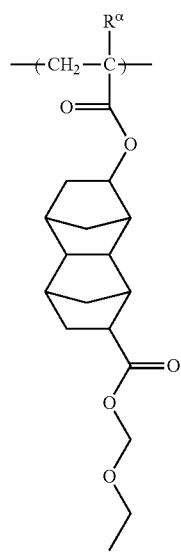
(a1-4-10) 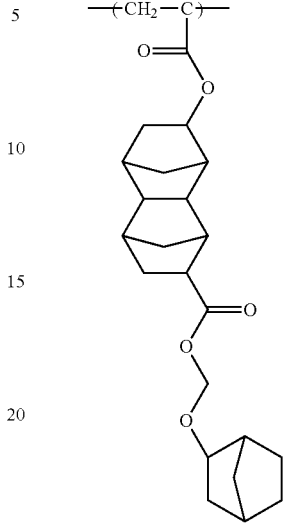
(a1-4-9) 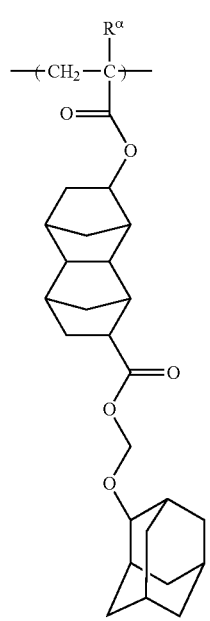
(a1-4-11) 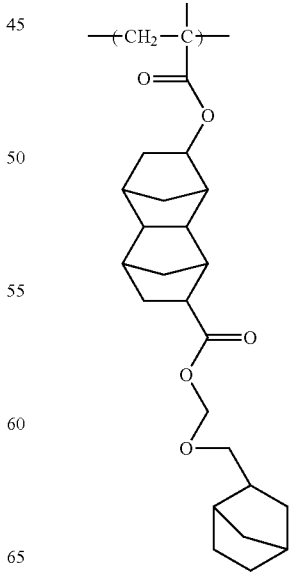

(a1-4-12)

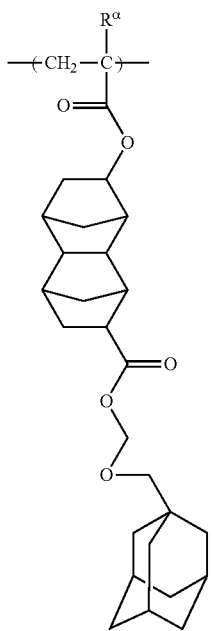

(a1-4-13)

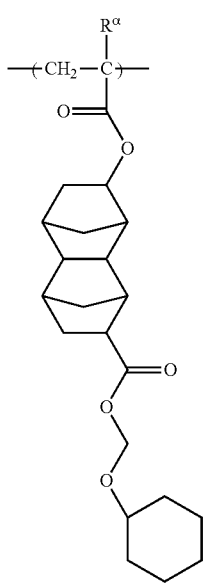

(a1-4-14)

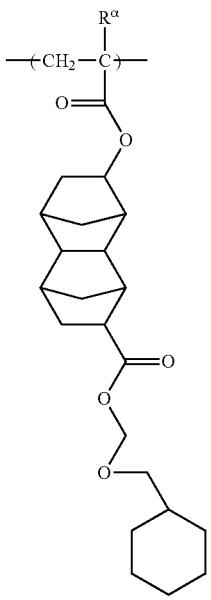

(a1-4-15)

In the present invention, as the structural unit (a11), it is preferable to include at least one member selected from the group consisting of structural units represented by general formulae (a1-0-11) to (a1-0-15), (a1-2) and (a1-0-2), and it is more preferable to include at least one member selected from the group consisting of a structural unit represented by general formula (a1-0-11), a structural unit represented by general formula (a1-0-12), a structural unit represented by general formula (a1-0-15) and a structural unit represented by general formula (a1-2).

[Chemical Formula 23]

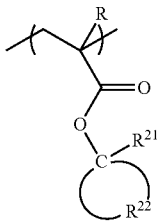
(a1-0-11)

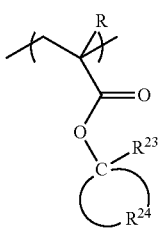
(a1-0-12)

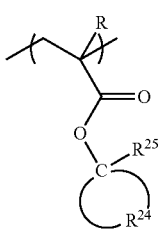
(a1-0-13)

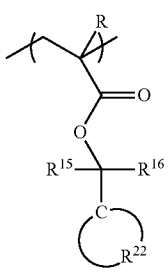
(a1-0-14)

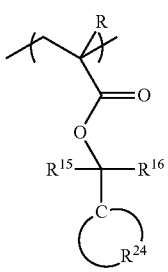
(a1-0-15)

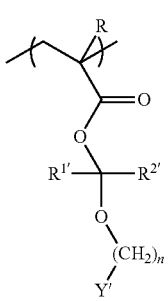
(a1-2)

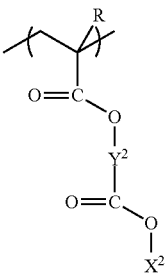
(a1-0-2)

In the formulas, R represents a hydrogen atom, an alkyl group of 1 to 5 carbon atoms or a halogenated alkyl group of 1 to 5 carbon atoms; $R^{21}$ represents an alkyl group; $R^{22}$ represents a group which forms an aliphatic monocyclic group with the carbon atom to which $R^{22}$ is bonded; $R^{23}$ represents a branched alkyl group; $R^{24}$ represents a group which forms an aliphatic polycyclic group with the carbon atom to which $R^{24}$ is bonded; $R^{25}$ represents a linear alkyl group of 1 to 5 carbon atoms; $R^{15}$ and $R^{16}$ each independently represents an alkyl group; each of $R^{1\prime}$ and $R^{2\prime}$ independently represents a hydrogen atom or an alkyl group of 1 to 5 carbon atoms; n represents an integer of 0 to 3; $Y'$ represents an alkyl group of 1 to 5 carbon atoms or an aliphatic cyclic group; $Y^2$ represents a divalent linking group; and $X^2$ represents an acid dissociable group.

In the formulas, R, $Y^2$ and $X^2$ are the same as defined above.

In general formula (a1-0-11), as the alkyl group for $R^{21}$, the same alkyl groups as those described above for $R^{14}$ in formulas (1-1) to (1-9) can be used, preferably a methyl group, an ethyl group or an isopropyl group, and more preferably a methyl group or an ethyl group.

As the aliphatic monocyclic group formed by $R^{22}$ and the carbon atoms to which $R^{22}$ is bonded, the same aliphatic cyclic groups as those described above for the aforementioned tertiary alkyl ester-type acid dissociable group and which are monocyclic can be used. Specific examples include groups in which one or more hydrogen atoms have been removed from a monocycloalkane. The monocycloalkane is preferably a 3- to 11-membered ring, more preferably a 3- to 8-membered ring, still more preferably a 4- to 6-membered ring, and most preferably a 5- or 6-membered ring.

The monocycloalkane may or may not have part of the carbon atoms constituting the ring replaced with an ether bond (—O—).

Further, the monocycloalkane may have a substituent such as an alkyl group of 1 to 5 carbon atoms, a fluorine atom or a fluorinated alkyl group of 1 to 5 carbon atoms.

As an examples of $R^{22}$ constituting such an aliphatic cyclic group, an alkylene group which may have an ether bond (—O—) interposed between the carbon atoms can be given.

Specific examples of structural units represented by general formula (a1-0-11) include structural units represented by the aforementioned formulas (a1-1-16) to (a1-1-23), (a1-1-27) and (a1-1-31) to (a1-1-33). Among these, a structural unit represented by general formula (a1-1-02) shown below which includes the structural units represented by the aforementioned formulas (a1-1-16), (a1-1-17), (a1-1-20) to (a1-1-23), (a1-1-27) and (a1-1-31) to (a1-1-33) is preferable. Further, a structural unit represented by general formula (a1-1-02') shown below is also preferable.

In the formulas, h is preferably 1 or 2.

[Chemical Formula 24]

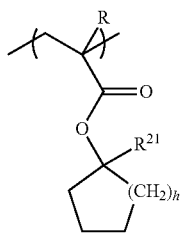

(a1-1-02)

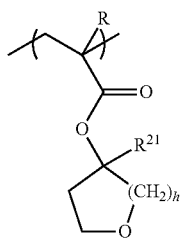

(a1-1-02′)

In the formulae, R and $R^{21}$ are the same as defined above; and h represents an integer of 1 to 4.

In general formula (a1-0-12), as the branched alkyl group for $R^{23}$, the same alkyl groups as those described above for $R^{14}$ which are branched can be used, and an isopropyl group is particularly desirable.

As the aliphatic polycyclic group formed by $R^{24}$ and the carbon atoms to which $R^{24}$ is bonded, the same aliphatic cyclic groups as those described above for the aforementioned tertiary alkyl ester-type acid dissociable group and which are polycyclic can be used.

Specific examples of structural units represented by general formula (a1-0-12) include structural units represented by the aforementioned formulas (a1-1-26) and (a1-1-28) to (a1-1-30).

As the structural unit (a1-0-12), a structural unit in which the aliphatic polycyclic group formed by $R^{24}$ and the carbon atom to which $R^{24}$ is bonded is a 2-adamantyl group is preferable, and a structural unit represented by the aforementioned formula (a1-1-26) is particularly desirable.

In general formula (a1-0-13), R and $R^{24}$ are the same as defined above.

As the linear alkyl group for $R^{25}$, the same linear alkyl groups as those described above for $R^{14}$ in the aforementioned formulas (1-1) to (1-9) can be mentioned, and a methyl group or an ethyl group is particularly desirable.

Specific examples of structural units represented by general formula (a1-0-13) include structural units represented by the aforementioned formulas (a1-1-1) to (a1-1-3) and (a1-1-7) to (a1-1-15) which were described above as specific examples of the structural unit represented by general formula (a1-1).

As the structural unit (a1-0-13), a structural unit in which the aliphatic polycyclic group formed by $R^{24}$ and the carbon atom to which $R^{24}$ is bonded is a 2-adamantyl group is preferable, and a structural unit represented by the aforementioned formula (a1-1-1), (a1-1-2) or (a1-1-9) is particularly desirable.

In general formula (a1-0-14), R and $R^{22}$ are the same as defined above. $R^{15}$ and $R^{16}$ are the same as $R^{15}$ and $R^{16}$ in the aforementioned general formulae (2-1) to (2-6), respectively.

Specific examples of structural units represented by general formula (a1-0-14) include structural units represented by the aforementioned formulae (a1-1-35) and (a1-1-36) which were described above as specific examples of the structural unit represented by general formula (a1-1).

In general formula (a1-0-15), R and $R^{24}$ are the same as defined above. $R^{15}$ and $R^{16}$ are the same as $R^{15}$ and $R^{16}$ in the aforementioned general formulae (2-1) to (2-6), respectively.

Specific examples of structural units represented by general formula (a1-0-15) include structural units represented by the aforementioned formulae (a1-1-4) to (a1-1-6) and (a1-1-34) which were described above as specific examples of the structural unit represented by general formula (a1-1).

In formula (a1-2), $R^{1'}$, $R^{2'}$, n and Y' are the same as defined above.

It is preferable that at least one of $R^{1'}$ and $R^{2'}$ is a hydrogen atom, and it is particularly desirable that both $R^{1'}$ and $R^{2'}$ are hydrogen atoms.

n is more preferably 0 or 1, and most preferably 0.

Y' is preferably an aliphatic cyclic group, and the same aliphatic cyclic groups as those given as examples for the aforementioned "acid dissociable group containing an aliphatic cyclic group" can be mentioned, and a group in which one or more hydrogen atoms have been removed from a polycycloalkane is more preferable.

Specific examples of the structural unit represented by formula (a1-2) include a structural unit represented by formula (a1-2-6).

Examples of structural units represented by general formula (a1-0-2) include structural units represented by the aforementioned formulas (a1-3) and (a1-4).

As the structural unit represented by formula (a1-0-2), a structural unit in which $Y^2$ is a group represented by the aforementioned formula —$Y^{21}$—O—$Y^{22}$—, a group represented by the aforementioned formula —[$Y^{21}$—C(=O)—O]$_{m'}$—$Y^{22}$— or a group represented by the aforementioned formula —$Y^{21}$—O—C(=O)—$Y^{22}$— is particularly desirable.

Preferable examples of such structural units include a structural unit represented by general formula (a1-3-01) shown below, a structural unit represented by general formula (a1-3-02) shown below, and a structural unit represented by general formula (a1-3-03) shown below.

[Chemical Formula 25]

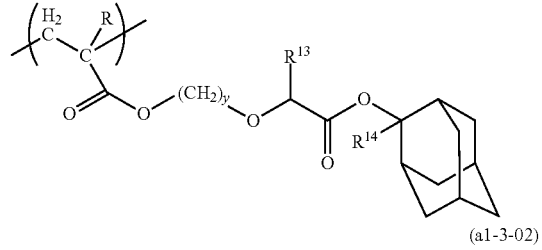

(a1-3-01)

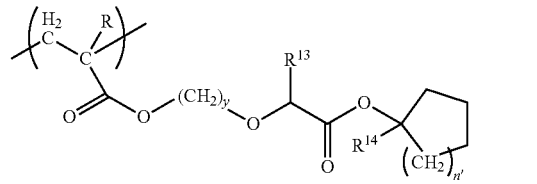

(a1-3-02)

In the formulas, R is the same as defined above; $R^{13}$ represents a hydrogen atom or a methyl group; $R^{14}$ represents an alkyl group; y represents an integer of 1 to 10; and n' represents an integer of 0 to 3.

[Chemical Formula 26]

(a1-3-03)

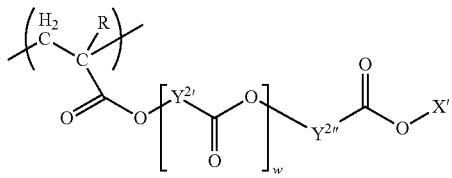

In the formula, R is as defined above; each of $Y^{2\prime}$ and $Y^{2\prime\prime}$ independently represents a divalent linking group; X' represents an acid dissociable group; and w represents an integer of 0 to 3.

In general formulas (a1-3-01) and (a1-3-02), $R^{13}$ is preferably a hydrogen atom.

$R^{14}$ is the same as defined for $R^{14}$ in the aforementioned formulas (1-1) to (1-9).

w is preferably an integer of 1 to 8, more preferably 1 to 5, and most preferably 1 or 2.

n' is preferably 1 or 2, and most preferably 2.

Specific examples of structural units represented by general formula (a1-3-01) include structural units represented by the aforementioned formulas (a1-3-25) and (a1-3-26).

Specific examples of structural units represented by general formula (a1-3-02) include structural units represented by the aforementioned formulas (a1-3-27) and (a1-3-28).

In general formula (a1-3-03), as the divalent linking group for $Y^{2\prime}$ and $Y^{2\prime\prime}$, the same groups as those described above for $Y^2$ in general formula (a1-3) can be used.

As $Y^{2\prime}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As $Y^{2\prime\prime}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As the acid dissociable group for X', the same groups as those described above can be used. X' is preferably a tertiary alkyl ester-type acid dissociable group, more preferably the aforementioned group (i) in which a substituent is bonded to the carbon atom to which an atom adjacent to the acid dissociable group is bonded to on the ring skeleton to form a tertiary carbon atom. Among these, a group represented by the aforementioned general formula (1-1) is particularly desirable.

w represents an integer of 0 to 3, preferably an integer of 0 to 2, more preferably 0 or 1, and most preferably 1.

As the structural unit represented by general formula (a1-3-03), a structural unit represented by general formula (a1-3-03-1) or (a1-3-03-2) shown below is preferable, and a structural unit represented by general formula (a1-3-03-1) is particularly desirable.

[Chemical Formula 27]

(a1-3-03-1)

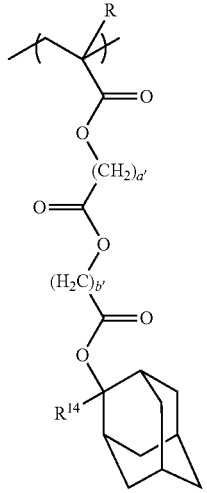

(a1-3-03-2)

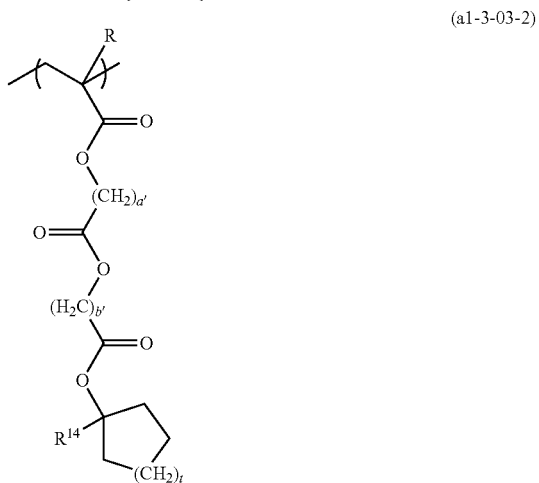

In the formulas, R and $R^{14}$ are the same as defined above; a' represents an integer of 1 to 10; b' represents an integer of 1 to 10; and t represents an integer of 0 to 3.

In general formulas (a1-3-03-1) and (a1-3-03-2), a' is preferably an integer of 1 to 8, more preferably 1 to 5, and most preferably 1 or 2.

b' is preferably an integer of 1 to 8, more preferably 1 to 5, and most preferably 1 or 2.

t is preferably an integer of 1 to 3, and most preferably 1 or 2.

Specific examples of structural units represented by general formula (a1-3-03-1) or (a1-3-03-2) include structural units represented by the aforementioned formulas (a1-3-29) to (a1-3-32).

(Structural Unit (a12)):

The structural unit (a12) is a structural unit derived from hydroxystyrene in which the hydrogen atom of the hydroxy group has been substituted with an acid dissociable group or a substituent containing an acid dissociable group, wherein the hydrogen atom bonded to the carbon atom on the α-position may be substituted with a substituent, and a hydrogen atom bonded to the benzene ring may be substituted with a substituent other than a hydroxy group.

As the acid dissociable group which substitutes the hydrogen atom of the hydroxy group, the same acid dissociable groups as those described above can be given, a tertiary alkyl ester-type acid dissociable group or an acetal-type acid dissociable group is preferable, and an acetal-type acid dissociable group is more preferable.

Examples of the substituent containing an acid dissociable group include a group constituted of an acid dissociable group and a divalent linking group. As the divalent linking group, the same divalent linking groups as those described above for $Y^2$ in the aforementioned formula (a1-0-2) can be given, and a group in which the terminal structure of the acid dissociable group-side is a carbonyloxy group is particularly desirable. In such a case, it is preferable that the acid dissociable group is bonded to the oxygen atom (—O—) of the carbonyloxy group.

As the substituent containing an acid dissociable group, a group represented by formula $R^{11'}$—O—C(=O)— or a group represented by formula $R^{11'}$—O—C(=O)— is preferable. In the formulae, $R^{11'}$ represents an acid dissociable group, and $R^{12'}$ represents a linear or branched alkylene group.

The acid dissociable group for $R^{11'}$ is preferably a tertiary alkyl ester-type acid dissociable group or an acetal-type acid dissociable group, and more preferably a tertiary alkyl ester-type acid dissociable group. Preferable examples of the tertiary alkyl ester-type acid dissociable group include the aforementioned aliphatic branched acid dissociable group represented by the formula —C($R^{71}$)($R^{72}$)($R^{73}$), a group represented by any one of formulae (1-1) to (1-9), and a group represented by any one of formulae (2-1) to (2-6).

Examples of the alkylene group for $R^{12'}$ include a methylene group, an ethylene group, a trimethylene group, a tetramethylene group and a 1,1-dimethylethylene group. As $R^{12'}$, a linear alkylene group is preferable.

(Structural Unit (a13)):

The structural unit (a13) is a structural unit derived from vinyl(hydroxynaphthalene) in which the hydrogen atom of the hydroxy group has been substituted with an acid dissociable group or a substituent containing an acid dissociable group, wherein the hydrogen atom bonded to the carbon atom on the α-position may be substituted with a substituent, and a hydrogen atom bonded to the naphthalene ring may be substituted with a substituent other than a hydroxy group.

In the structural unit (a13), as the acid dissociable group or the substituent containing an acid dissociable group which substitutes the hydrogen atom of the hydroxy group, the same groups as those described above for the structural unit (a12) can be mentioned.

When the component (A1-1) has a structural unit (a1), as the structural unit (a1), one type of structural unit may be used, or two or more types may be used.

In the component (A1-1), the amount of the structural unit (a1) based on the combined total of all structural units constituting the component (A1-1) is preferably 15 to 70 mol %, more preferably 15 to 60 mol %, and still more preferably 20 to 55 mol %.

When the amount of the structural unit (a1)) is at least as large as the lower limit of the above-mentioned range, a pattern can be easily formed using a resist composition prepared from the component (A1), and various lithography properties such as sensitivity, resolution, pattern shape and the like are improved. On the other hand, when the amount of the structural unit (a1) is no more than the upper limit of the above-mentioned range, a good balance can be achieved with the other structural units.

Structural Unit (a2)

In the present invention, the structural unit (a2) is a structural unit containing a —$SO_2$— containing cyclic group or a lactone-containing cyclic group.

When the component (A1-1) is used for forming a resist film, the —$SO_2$— containing cyclic group or the lactone-containing cyclic group within the structural unit (a2) is effective in improving the adhesion between the resist film and the substrate.

The aforementioned structural unit (a5) or (a1) which contains a —$SO_2$— containing cyclic group or a lactone-containing cyclic group falls under the definition of the structural unit (a2); however, such a structural unit is regarded as a structural unit (a5) or (a1), and does not fall under the definition of the structural unit (a2).

Here, an "—$SO_2$— containing cyclic group" refers to a cyclic group having a ring containing —$SO_2$— within the ring structure thereof, i.e., a cyclic group in which the sulfur atom (S) within —$SO_2$— forms part of the ring skeleton of the cyclic group. The ring containing —$SO_2$— within the ring skeleton thereof is counted as the first ring. A cyclic group in which the only ring structure is the ring that contains —$SO_2$— in the ring skeleton thereof is referred to as a monocyclic group, and a group containing other ring structures is described as a polycyclic group regardless of the structure of the other rings. The —$SO_2$— containing cyclic group may be either a monocyclic group or a polycyclic group.

As the —$SO_2$— containing cyclic group, a cyclic group containing —O—$SO_2$— within the ring skeleton thereof, i.e., a cyclic group containing a sultone ring in which —O—S— within the —O—$SO_2$— group forms part of the ring skeleton thereof is particularly desirable.

The —$SO_2$— containing cyclic group preferably has 3 to 30 carbon atoms, more preferably 4 to 20, still more preferably 4 to 15, and most preferably 4 to 12. Herein, the number of carbon atoms refers to the number of carbon atoms constituting the ring skeleton, excluding the number of carbon atoms within a substituent.

The —$SO_2$— containing cyclic group may be either a —$SO_2$— containing aliphatic cyclic group or a —$SO_2$— containing aromatic cyclic group. A —$SO_2$— containing aliphatic cyclic group is preferable.

Examples of the —$SO_2$— containing aliphatic cyclic group include aliphatic cyclic groups in which part of the carbon atoms constituting the ring skeleton has been substituted with a —$SO_2$— group or a —O—$SO_2$— group and has at least one hydrogen atom removed from the aliphatic hydrocarbon ring. Specific examples include an aliphatic hydrocarbon ring in which a —$CH_2$— group constituting the ring skeleton thereof has been substituted with a —$SO_2$— group and has at least one hydrogen atom removed therefrom; and an aliphatic hydrocarbon ring in which a —$CH_2$—$CH_2$— group constituting the ring skeleton has been substituted with a —O—$SO_2$— group and has at least one hydrogen atom removed therefrom.

The alicyclic hydrocarbon ring preferably has 3 to 20 carbon atoms, and more preferably 3 to 12 carbon atoms.

The alicyclic hydrocarbon ring may be either a monocyclic group or a polycyclic group. As the monocyclic group, a group in which two hydrogen atoms have been removed from a monocycloalkane of 3 to 6 carbon atoms is preferable. Examples of the monocycloalkane include cyclopentane and cyclohexane. As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The —SO₂— containing cyclic group may have a substituent. Examples of the substituent include an alkyl group, an alkoxy group, a halogen atom, a halogenated alkyl group, a hydroxy group, an oxygen atom (=O), —COOR", —OC(=O)R", a hydroxyalkyl group and a cyano group.

The alkyl group for the substituent is preferably an alkyl group of 1 to 6 carbon atoms. Further, the alkyl group is preferably a linear alkyl group or a branched alkyl group. Specific examples include a methyl group, an ethyl group, a propyl group, an isopropyl group, an n-butyl group, an isobutyl group, a tert-butyl group, a pentyl group, an isopentyl group, a neopentyl group and a hexyl group. Among these, a methyl group or ethyl group is preferable, and a methyl group is particularly desirable.

As the alkoxy group for the substituent, an alkoxy group of 1 to 6 carbon atoms is preferable. Further, the alkoxy group is preferably a linear or branched alkoxy group. Specific examples of the alkoxy group include the aforementioned alkyl groups for the substituent having an oxygen atom (—O—) bonded thereto.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

As examples of the halogenated alkyl group for the substituent, groups in which part or all of the hydrogen atoms of the aforementioned alkyl groups for the substituent have been substituted with the aforementioned halogen atoms can be given. As the halogenated alkyl group, a fluorinated alkyl group is preferable, and a perfluoroalkyl group is particularly desirable.

In the —COOR" group and the —OC(=O)R" group, R" represents a hydrogen atom or a linear, branched or cyclic alkyl group of 1 to 15 carbon atoms.

When R" represents a linear or branched alkyl group, it is preferably an alkyl group of 1 to 10 carbon atoms, more preferably an alkyl group of 1 to 5 carbon atoms, and most preferably a methyl group or an ethyl group.

When R" is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

The hydroxyalkyl group for the substituent preferably has 1 to 6 carbon atoms, and specific examples thereof include the aforementioned alkyl groups for the substituent in which at least one hydrogen atom has been substituted with a hydroxy group.

More specific examples of the —SO₂— containing cyclic group include groups represented by general formulas (3-1) to (3-4) shown below.

[Chemical Formula 28]

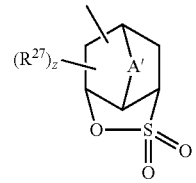

(3-1)

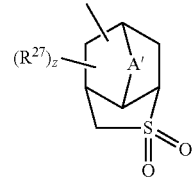

(3-2)

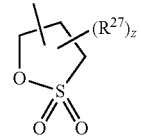

(3-3)

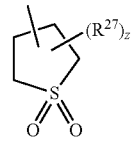

(3-4)

In the formulas, A' represents an oxygen atom, a sulfur atom or an alkylene group of 1 to 5 carbon atoms which may contain an oxygen atom or a sulfur atom; z represents an integer of 0 to 2; and $R^{27}$ represents an alkyl group, an alkoxy group, a halogenated alkyl group, a hydroxyl group, —COOR", —OC(=O)R", a hydroxyalkyl group or a cyano group, wherein R" represents a hydrogen atom or an alkyl group.

In general formulas (3-1) to (3-4) above, A' represents an oxygen atom (—O—), a sulfur atom (—S—) or an alkylene group of 1 to 5 carbon atoms which may contain an oxygen atom or a sulfur atom.

As the alkylene group of 1 to 5 carbon atoms represented by A', a linear or branched alkylene group is preferable, and examples thereof include a methylene group, an ethylene group, an n-propylene group and an isopropylene group.

Examples of alkylene groups that contain an oxygen atom or a sulfur atom include the aforementioned alkylene groups in which —O— or —S— is bonded to the terminal of the alkylene group or present between the carbon atoms of the alkylene group. Specific examples of such alkylene groups include —O—CH₂—, —CH₂—O—CH₂—, —S—CH₂—, —CH₂—S—CH₂—.

As A', an alkylene group of 1 to 5 carbon atoms or —O— is preferable, more preferably an alkylene group of 1 to 5 carbon atoms, and most preferably a methylene group.

z represents an integer of 0 to 2, and is most preferably 0.

When z is 2, the plurality of $R^{27}$ may be the same or different from each other.

As the alkyl group, alkoxy group, halogenated alkyl group, —COOR", —OC(=O)R" and hydroxyalkyl group for $R^{27}$, the same alkyl groups, alkoxy groups, halogenated alkyl groups, —COOR", —OC(=O)R" and hydroxyalkyl groups as those described above as the substituent for the —SO₂— containing cyclic group can be mentioned.

Specific examples of the cyclic groups represented by general formulas (3-1) to (3-4) are shown below. In the formulas shown below, "Ac" represents an acetyl group.
[Chemical Formula 29]
(3-1-1)
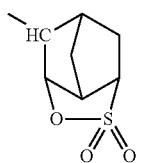
(3-1-2)
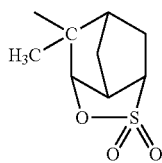
(3-1-3)
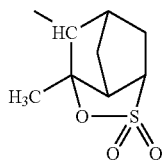
(3-1-4)
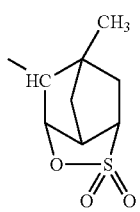
(3-1-5)
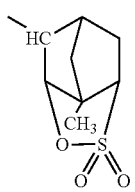
(3-1-6)
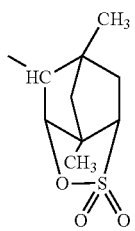
(3-1-7)
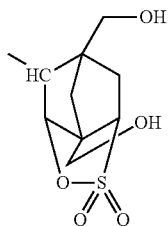
-continued
(3-1-8)
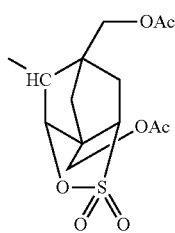
(3-1-9)
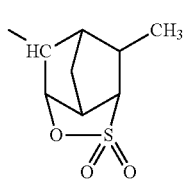
(3-1-10)
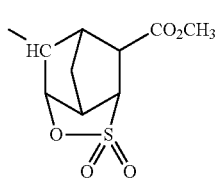
(3-1-11)
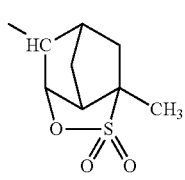
(3-1-12)
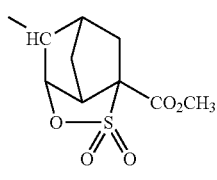
(3-1-13)
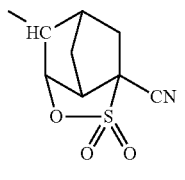
(3-1-14)
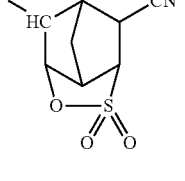
(3-1-15)
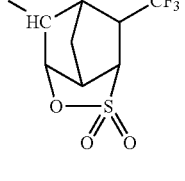
(3-1-16)
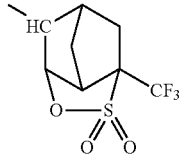

-continued
(3-1-17)
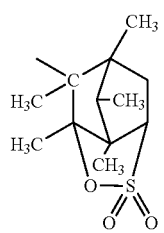
(3-1-18)
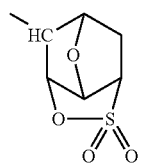
(3-1-19)
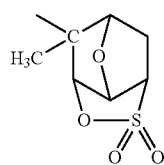
(3-1-20)
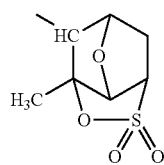
(3-1-21)
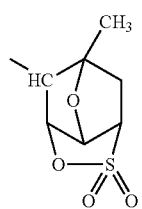
[Chemical Formula 30]
(3-1-22)
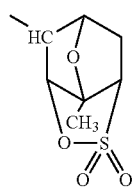
(3-1-23)
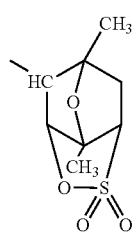
-continued
(3-1-24)
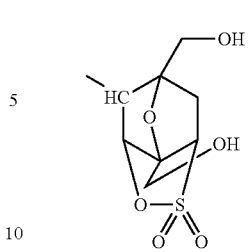
(3-1-25)
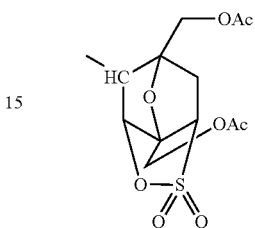
(3-1-26)
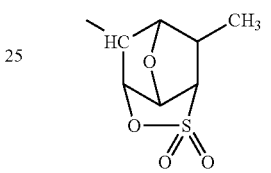
(3-1-27)
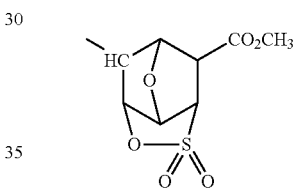
(3-1-28)
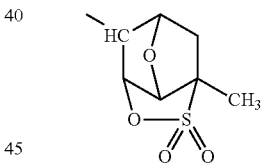
(3-1-29)
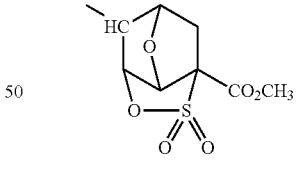
(3-1-30)
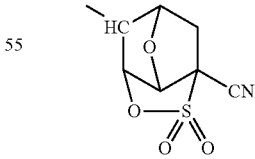
(3-1-31)
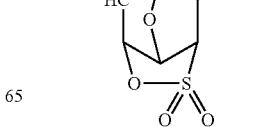

(3-1-32)

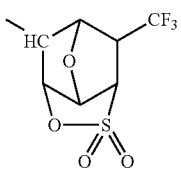

(3-1-33)

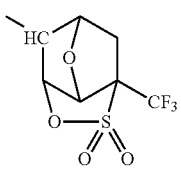

[Chemical Formula 31]

(3-2-1)

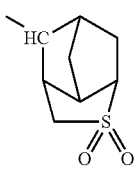

(3-2-2)

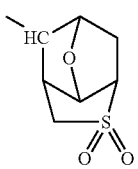

(3-3-1)

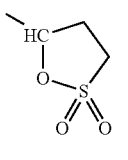

(3-4-1)

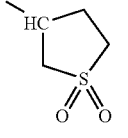

As the —SO$_2$— containing cyclic group, a group represented by the aforementioned general formula (3-1) is preferable, at least one member selected from the group consisting of groups represented by the aforementioned chemical formulas (3-1-1), (3-1-18), (3-3-1) and (3-4-1) is more preferable, and a group represented by chemical formula (3-1-1) is most preferable.

The term "lactone-containing cyclic group" refers to a cyclic group including a ring containing a —O—C(=O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings. The lactone-containing cyclic group may be either a monocyclic group or a polycyclic group.

The lactone-containing cyclic group for the structural unit (a2) is not particularly limited, and an arbitrary structural unit may be used. Specific examples of lactone-containing monocyclic groups include a group in which one hydrogen atom has been removed from a 4- to 6-membered lactone ring, such as a group in which one hydrogen atom has been removed from β-propionolatone, a group in which one hydrogen atom has been removed from γ-butyrolactone, and a group in which one hydrogen atom has been removed from δ-valerolactone. Further, specific examples of lactone-containing polycyclic groups include groups in which one hydrogen atom has been removed from a lactone ring-containing bicycloalkane, tricycloalkane or tetracycloalkane.

With respect to the structural unit (a2), there is not particular limitation to the structure of the other portion, as long as the structural unit has a —SO$_2$— containing cyclic group or a lactone-containing cyclic group. The structural unit (a2) is preferably at least one structural unit selected from the group consisting of a structural unit (a2$^S$) derived from an acrylate ester which may have the hydrogen atom bonded to the carbon atom on the α-position substituted with a substituent and contains an —SO$_2$— containing cyclic group, and a structural unit (a2$^L$) derived from an acrylate ester which may have the hydrogen atom bonded to the carbon atom on the α-position substituted with a substituent and contains a lactone-containing cyclic group.

Structural Unit (a2$^S$):

More specific examples of the structural unit (a2$^S$) include structural units represented by general formula (a2-0) shown below.

[Chemical Formula 32]

(a2-0)

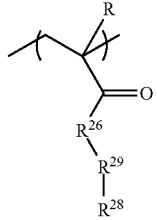

In the formula, R represents a hydrogen atom, an alkyl group of 1 to 5 carbon atoms or a halogenated alkyl group of 1 to 5 carbon atoms; $R^{26}$ represents —O— or —NH—; $R^{28}$ represents a —SO$_2$— containing cyclic group; and $R^{29}$ represents a single bond or a divalent linking group.

In general formula (a2-0), R is the same as defined above.

$R^{26}$ represents —O— or —NH—.

$R^{28}$ is the same as defined for the aforementioned —SO$_2$— containing group.

$R^{29}$ may be either a single bond or a divalent linking group. In terms of the effects of the present invention, a divalent linking group is preferable.

The divalent linking group for $R^{29}$ is not particularly limited, and examples thereof include the same divalent linking groups as those described above for $R^2$ in the aforementioned formula (a5-0). Among these, an alkylene group or a divalent linking group containing an ester bond (—C(=O)—O—) is preferable.

As the alkylene group, a linear or branched alkylene group is preferable. Specific examples include the same linear alkylene groups and branched alkylene groups as those described above for the aliphatic hydrocarbon group represented by $R^2$ in the aforementioned formula (a5-0).

As the divalent linking group containing an ester bond, a group represented by general formula: —$R^{30}$—C(=O)—O— (in the formula, $R^{30}$ represents a divalent linking group) is particularly desirable. That is, the structural unit (a2$^S$) is preferably a structural unit represented by general formula (a2-0-1) shown below.

[Chemical Formula 33]

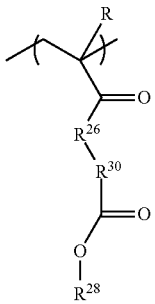

(a2-0-1)

In the formula, R, $R^{26}$ and $R^{28}$ are the same as defined above; and $R^{30}$ represents a divalent linking group.

$R^{30}$ is not particularly limited, and examples thereof include the same divalent linking groups as those described above for $R^2$ in the aforementioned formula (a5-0).

As the divalent linking group for $R^{30}$, a linear or branched alkylene group, an aliphatic hydrocarbon group having a ring in the structure thereof, or a divalent linking group containing a hetero atom is preferable, and a linear or branched alkylene group or a divalent linking group containing a hetero atom is more preferable.

As the linear alkylene group, a methylene group or an ethylene group is preferable, and a methylene group is particularly desirable.

As the branched alkylene group, an alkylmethylene group or an alkylethylene group is preferable, and —CH(CH$_3$)—, —C(CH$_3$)$_2$— or —C(CH$_3$)$_2$CH$_2$— is particularly desirable. As the divalent linking group containing a hetero atom, a divalent linking group containing an ether bond or an ester bond is preferable, and a group represented by the aforementioned formula —$Y^{21}$—O—$Y^{22}$—, —[$Y^{21}$—C(=O)—O]$_{m'}$—$Y^{22}$— or —$Y^{21}$—O—C(=O)—$Y^{22}$— is more preferable. Each of $Y^{21}$ and $Y^{22}$ independently represents a divalent hydrocarbon group which may have a substituent; and m' represents an integer of 0 to 3. Among these, —$Y^{21}$—O—C(=O)—$Y^{22}$— is preferable, and a group represented by the formula —(CH$_2$)$_c$—O—C(=O)—(CH$_2$)$_d$— is particularly desirable. c represents an integer of 1 to 5, and preferably 1 or 2. d represents an integer of 1 to 5, and preferably 1 or 2.

In particular, as the structural unit (a2$^S$), a structural unit represented by general formula (a2-0-11) or (a2-0-12) shown below is preferable, and a structural unit represented by general formula (a2-0-12) shown below is more preferable.

[Chemical Formula 34]

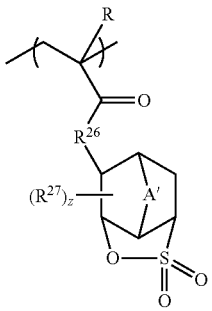

(a2-0-11)

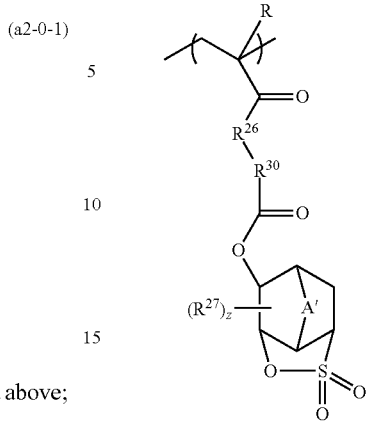

(a2-0-12)

In the formulae, R, A', $R^{26}$, $R^{27}$, z and $R^{30}$ are the same as defined above.

In general formula (a2-0-11), A' is preferably a methylene group, an oxygen atom (—O—) or a sulfur atom (—S—).

As $R^{30}$, a linear or branched alkylene group or a divalent linking group containing an oxygen atom is preferable. As the linear or branched alkylene group and the divalent linking group containing an oxygen atom represented by $R^{30}$, the same linear or branched alkylene groups and the divalent linking groups containing an oxygen atom as those described above can be mentioned.

As the structural unit represented by general formula (a2-0-12), a structural unit represented by general formula (a2-0-12a) or (a2-0-12b) shown below is particularly desirable.

[Chemical Formula 35]

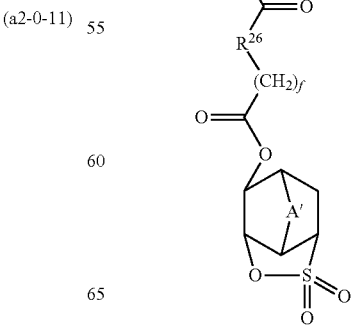

(a2-0-12a)

(a2-0-12b)

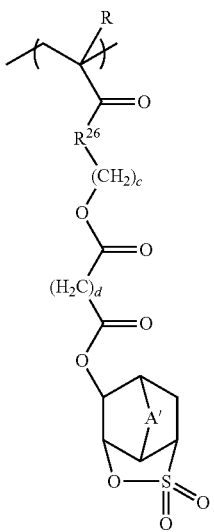

In the formulae, R, $R^{26}$ and A' are the same as defined above; and each of c, d and f independently represents an integer of 1 to 3.

Structural Unit ($a2^L$):

Examples of the structural unit ($a2^L$) include structural units represented by the aforementioned general formula (a2-0) in which the $R^{28}$ group has been substituted with a lactone-containing cyclic group. Specific examples include structural units represented by general formulas (a2-1) to (a2-5) shown below.

[Chemical Formula 36]

(a2-1)

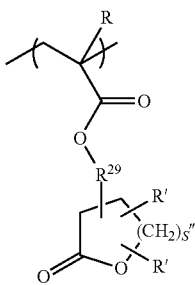

(a2-2)

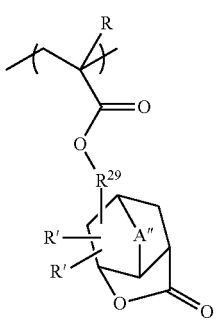

(a2-3)

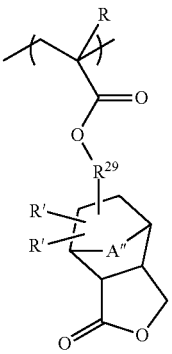

(a2-4)

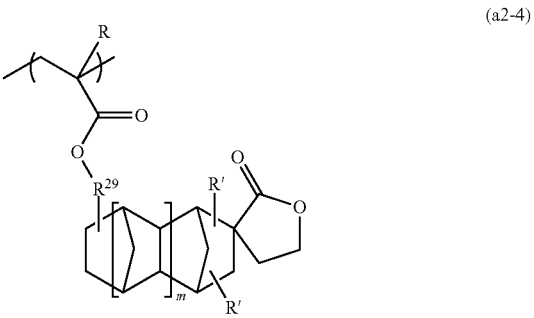

(a2-5)

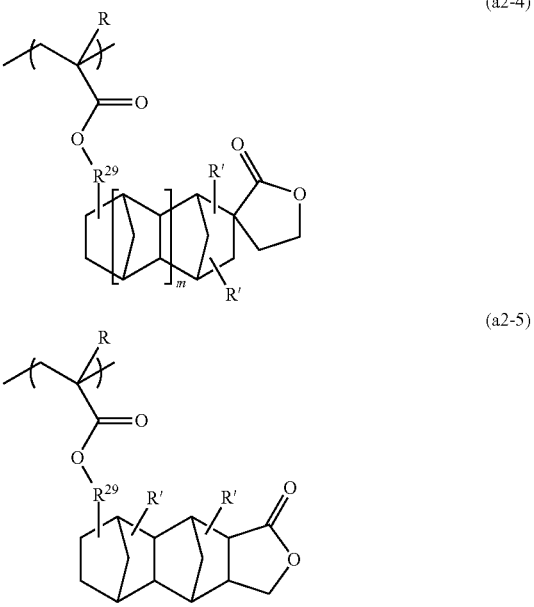

In the formulas, R represents a hydrogen atom, an alkyl group of 1 to 5 carbon atoms or a halogenated alkyl group of 1 to 5 carbon atoms; each R' independently represents a hydrogen atom, an alkyl group, an alkoxy group, a halogenated alkyl group, a hydroxy group, —COOR", OC(=O)R", a hydroxyalkyl group or a cyano group, wherein R" represents a hydrogen atom or an alkyl group; $R^{29}$ represents a single bond or a divalent linking group; s" represents an integer of 0 to 2; A" represents an oxygen atom, a sulfur atom or an alkylene group of 1 to 5 carbon atoms which may contain an oxygen atom or a sulfur atom; and m represents 0 or 1.

In general formulas (a2-1) to (a2-5), R is the same as defined above.

As the alkyl group, alkoxy group, halogenated alkyl group, —COOR", —OC(=O)R" and hydroxyalkyl group for R', the same alkyl groups, alkoxy groups, halogenated alkyl groups, —COOR", —OC(=O)R" and hydroxyalkyl groups as those described above as the substituent for the —SO₂— containing cyclic group can be mentioned.

In terms of industrial availability, R' is preferably a hydrogen atom.

The alkyl group for R" may be any of linear, branched or cyclic.

When R" is a linear or branched alkyl group, it preferably has 1 to 10 carbon atoms, more preferably 1 to 5 carbon atoms.

When R" is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Examples of such groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

As examples of A", the same groups as those described above for A' in general formula (3-1) can be given. A" is preferably an alkylene group of 1 to 5 carbon atoms, an oxygen atom (—O—) or a sulfur atom (—S—), and more preferably an alkylene group of 1 to 5 carbon atoms or —O—. As the alkylene group of 1 to 5 carbon atoms, a methylene group or a dimethylethylene group is preferable, and a methylene group is particularly desirable.

$R^{29}$ is the same as defined for $R^{29}$ in the aforementioned general formula (a2-0).

In formula (a2-1), s" is preferably 1 or 2.

Specific examples of structural units represented by general formulas (a2-1) to (a2-5) are shown below. In the formulae shown below, $R^\alpha$ represents a hydrogen atom, a methyl group or a trifluoromethyl group.

[Chemical Formula 37]

(a2-1-1)

(a2-1-2)

(a2-1-3)

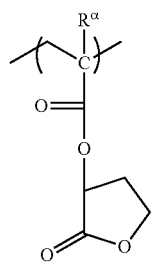
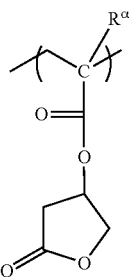
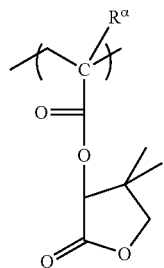

-continued (a2-1-4)

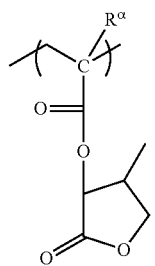

(a2-1-5)

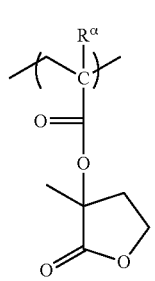

(a2-1-6)

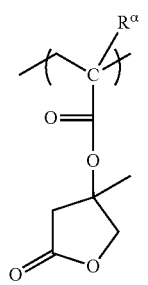

(a2-1-7)

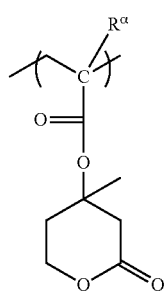

(a2-1-8)

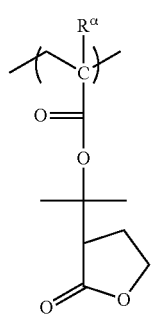

-continued
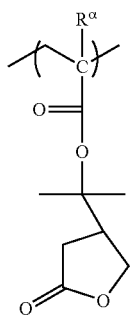 (a2-1-9)
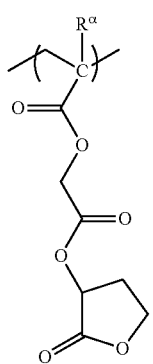 (a2-1-10)
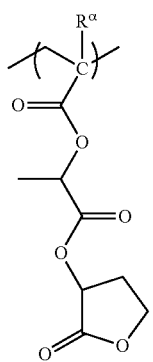 (a2-1-11)
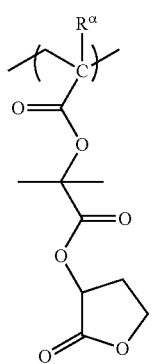 (a2-1-12)
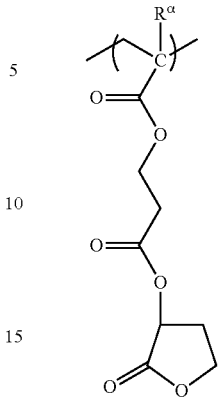 (a2-1-13)
[Chemical Formula 38]
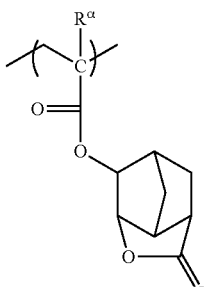 (a2-2-1)
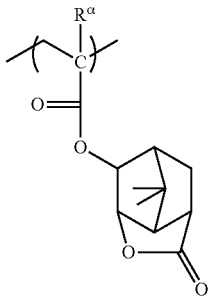 (a2-2-2)
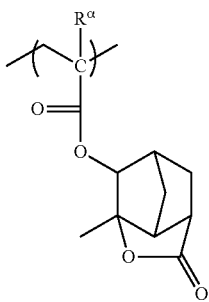 (a2-2-3)

(a2-2-4)
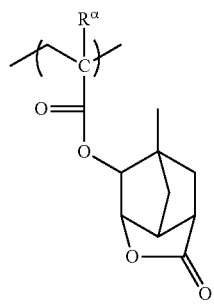
(a2-2-5)
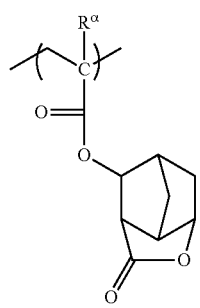
(a2-2-6)
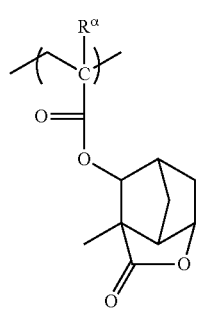
(a2-2-7)
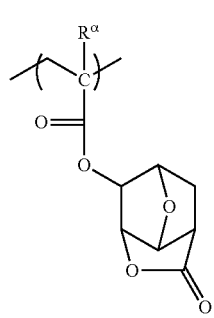
(a2-2-8)
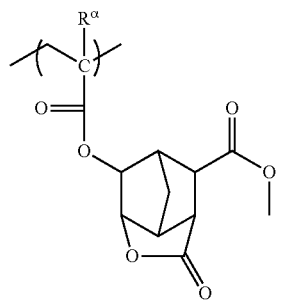
(a2-2-9)
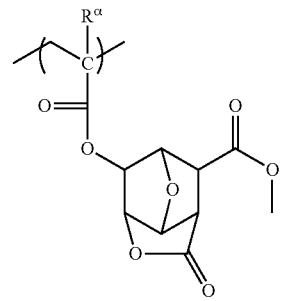
(a2-2-10)
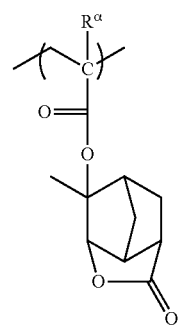
(a2-2-11)
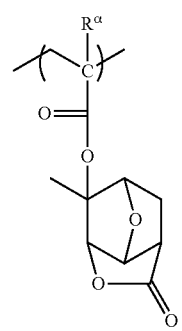
(a2-2-12)
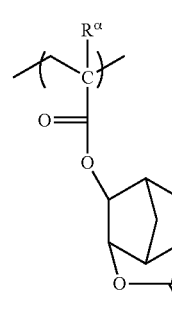

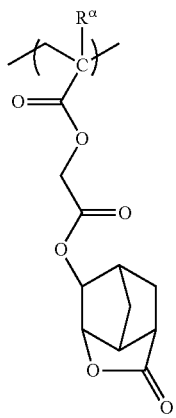
(a2-2-13)
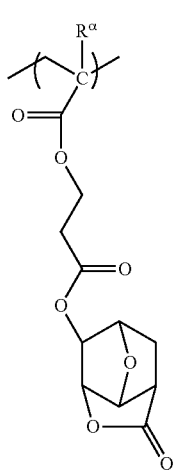
(a2-2-14)
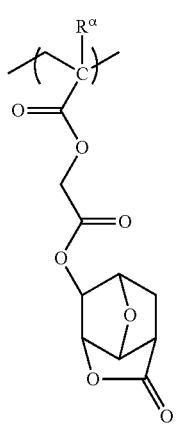
(a2-2-15)
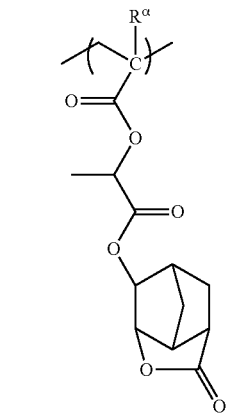
(a2-2-16)
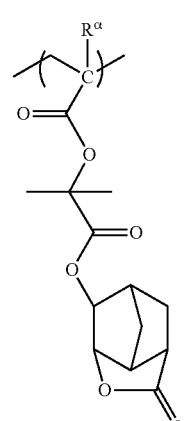
(a2-2-17)
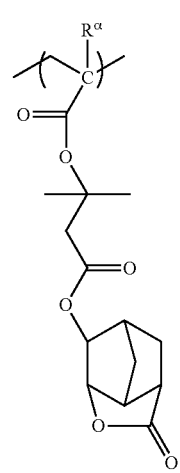
(a2-2-18)
[Chemical Formula 39]
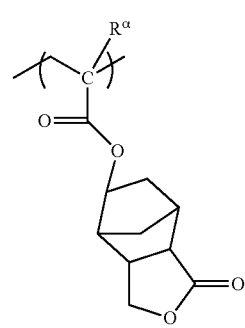
(a2-3-1)

(a2-3-2) 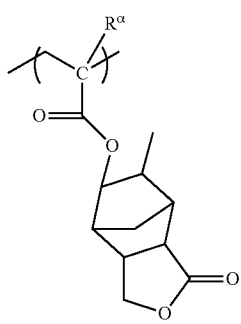
(a2-3-3) 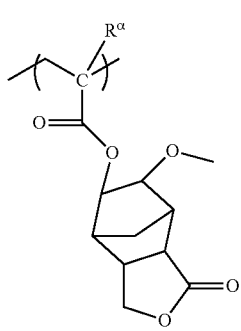
(a2-3-4) 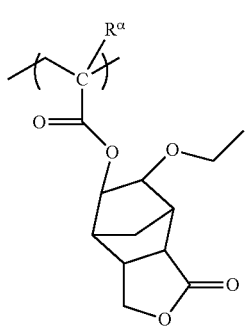
(a2-3-5) 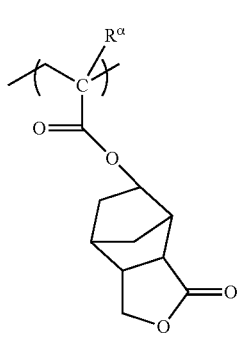
[Chemical Formula 40]
(a2-4-1) 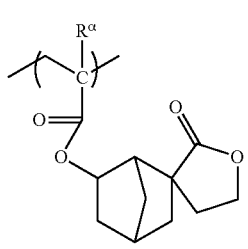
(a2-4-2) 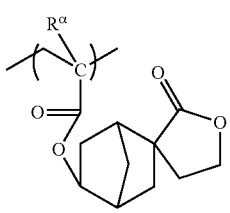
(a2-4-3) 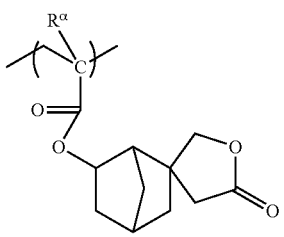
(a2-4-4) 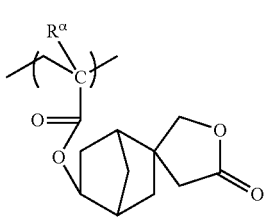
(a2-4-5) 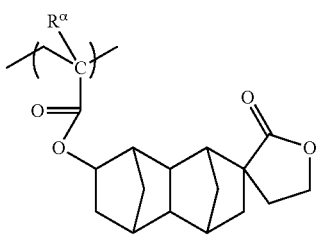
(a2-4-6) 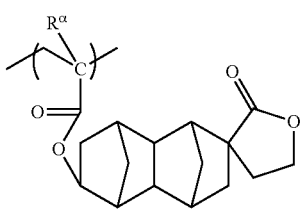
(a2-4-7) 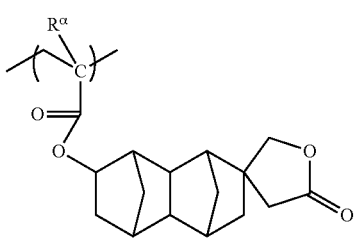
(a2-4-8) 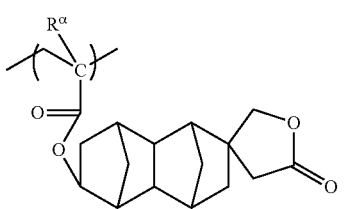

[Chemical Formula 41]
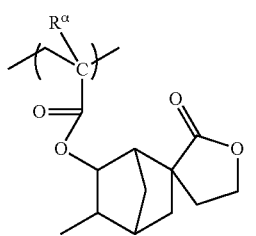 (a2-4-9)
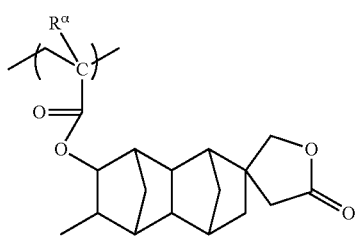 (a2-4-10)
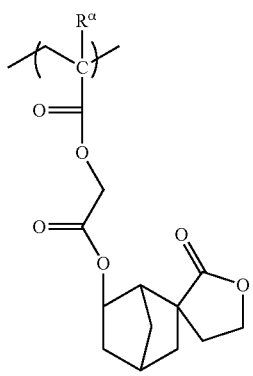 (a2-4-11)
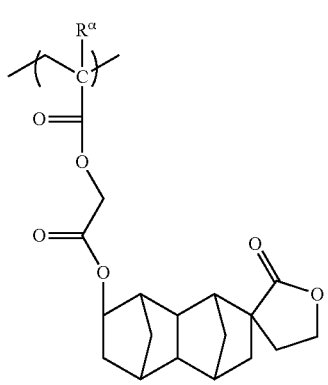 (a2-4-12)
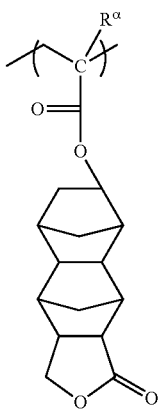 (a2-5-1)
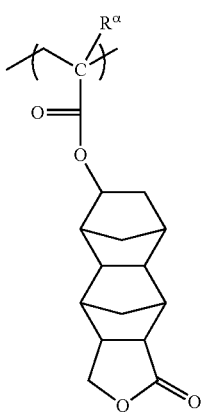 (a2-5-2)
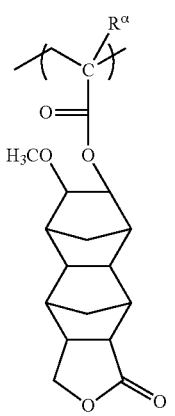 (a2-5-3)
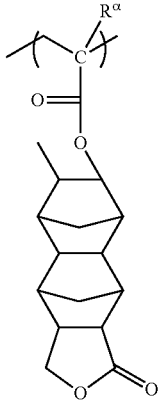 (a2-5-4)

(a2-5-5)

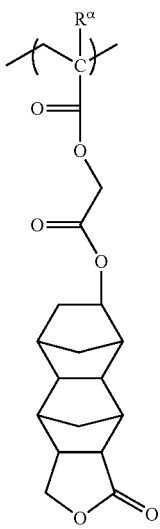

[Chemical Formula 42]

(a 2-6)

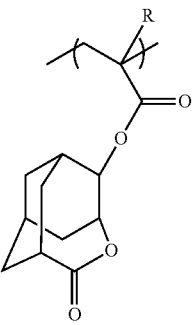

(a 2-7)

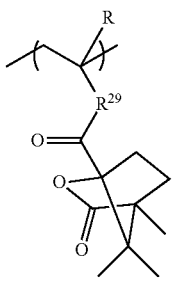

(a2-5-6)

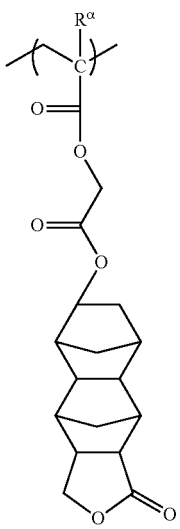

As the structural unit (a2$^L$), it is preferable to include at least one structural unit selected from the group consisting of structural units represented by the aforementioned general formulas (a2-1) to (a2-5), more preferably at least one structural unit selected from the group consisting of structural units represented by the aforementioned general formulas (a2-1) to (a2-3), and most preferably at least one structural unit selected from the group consisting of structural units represented by the aforementioned general formulas (a2-1) and (a2-3).

Specifically, it is preferable to use at least one structural unit selected from the group consisting of formulae (a2-1-1), (a2-1-2), (a2-2-1), (a2-2-7), (a2-2-12), (a2-2-13), (a2-2-15), (a2-3-1) and (a2-3-5).

Further, as the structural unit (a2$^L$), a structural unit represented by general formula (a2-6) or (a2-7) shown below is also preferable.

In the formulae, R and R$^{29}$ are the same as defined above.

When the component (A1-1) has a structural unit (a2), as the structural unit (a2), one type of structural unit may be used, or two or more types may be used. For example, as the structural unit (a2), a structural unit (a2$^S$) may be used alone, or a structural unit (a2$^L$), or a combination of these structural units may be used. Further, as the structural unit (a2$^S$) or the structural unit (a2$^L$), either a single type of structural unit may be used, or two or more types may be used in combination.

In the component (A1-1), the amount of the structural unit (a2) based on the combined total of all structural units constituting the component (A1-1) is preferably 1 to 80 mol %, more preferably 10 to 70 mol %, still more preferably 10 to 65 mol %, and most preferably 10 to 60 mol %.

When the amount of the structural unit (a2) is at least as large as the lower limit of the above-mentioned range, the effect of using the structural unit (a2) can be satisfactorily achieved. On the other hand, when the amount of the structural unit (a2) is no more than the upper limit of the above-mentioned range, a good balance can be achieved with the other structural units, and various lithography properties and pattern shape can be improved.

Structural Unit (a3)

In the present invention, the structural unit (a3) is a structural unit containing a polar group.

When the component (A1-1) includes the structural unit (a3), the polarity of the component (A1-1) after exposure is further increased. Increase in the polarity of the component (A1-1) as the base resin contributes to improvement in terms of resolution and the like, particularly in an alkali developing process.

Examples of the polar group include —OH, —COOH, —CN, —SO$_2$NH$_2$ and —CONH$_2$. Structural units that contain —COOH include structural units of (α-substituted) acrylic acid.

The structural unit (a3) is preferably a structural unit containing a hydrocarbon group in which part of the hydrogen atoms has been substituted with a polar group. The hydrocarbon group may be either an aliphatic hydrocarbon group or an aromatic hydrocarbon group. Among these, as the hydrocarbon group, an aliphatic hydrocarbon group is preferable.

Examples of the aliphatic hydrocarbon group as the hydrocarbon group include linear or branched hydrocarbon groups (preferably alkylene groups) of 1 to 10 carbon atoms, and aliphatic cyclic groups (monocyclic groups and polycyclic groups).

These aliphatic cyclic groups (monocyclic groups and polycyclic groups) can be selected appropriately from the multitude of groups that have been proposed for the resins of resist compositions designed for use with ArF excimer lasers. The aliphatic cyclic group preferably has 3 to 30 carbon atoms, more preferably 5 to 30, still more preferably 5 to 20, still more preferably 6 to 15, and most preferably 6 to 12. As the aliphatic cyclic group, a group in which two or more hydrogen atoms have been removed from a monocycloalkane or a polycycloalkane such as a bicycloalkane, tricycloalkane or tetracycloalkane can be used. Specific examples include groups in which two or more hydrogen atoms have been removed from a monocycloalkane such as cyclopentane or cyclohexane; and groups in which two or more hydrogen atoms have been removed from a polycycloalkane such as adamantane, norbornane, isobornane, tricyclodecane or tetracyclododecane. The aliphatic cyclic group may or may not have a substituent. Examples of the substituent include an alkyl group of 1 to 5 carbon atoms, a fluorine atom, and a fluorinated alkyl group of 1 to 5 carbon atoms.

The aromatic hydrocarbon group as the hydrocarbon group is a hydrocarbon group having at least one aromatic ring.

The aromatic ring is not particularly limited, as long as it is a cyclic conjugated compound having 4n+2π electrons (wherein n represents 0 or a natural number), and may be either monocyclic or polycyclic. The aromatic ring preferably has 5 to 30 carbon atoms, more preferably 5 to 20, still more preferably 6 to 15, and most preferably 6 to 12. Here, the number of carbon atoms within a substituent(s) is not included in the number of carbon atoms of the aromatic hydrocarbon group. Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring.

Specific examples of the aromatic hydrocarbon group as the divalent hydrocarbon group include a group in which two or more hydrogen atoms have been removed from the aforementioned aromatic hydrocarbon ring or aromatic hetero ring (arylene group or heteroarylene group); a group in which two ore more hydrogen atoms have been removed from an aromatic compound having two or more aromatic rings (biphenyl, fluorene or the like); and a group in which one hydrogen atom of the aforementioned aromatic ring has been substituted with an alkylene group (an arylalkyl group such as a benzyl group, a phenethyl group, a 1-naphthylmethyl group, a 2-naphthylmethyl group, a 1-naphthylethyl group, or a 2-naphthylethyl group, or a heteroarylalkyl group) and has one hydrogen atom removed from the aromatic ring. The alkylene group which substitutes the hydrogen atom of the aforementioned aromatic hydrocarbon ring or the aromatic hetero ring preferably has 1 to 4 carbon atoms, more preferably 1 or 2 carbon atoms, and most preferably 1 carbon atom.

The aromatic hydrocarbon group may have a substituent. For example, the hydrogen atom bonded to the aromatic ring within the aromatic hydrocarbon group may be substituted with a substituent. Examples of substituents include an alkyl group, an alkoxy group, a halogen atom, a halogenated alkyl group, a hydroxyl group and an oxygen atom (=O).

The alkyl group as the substituent is preferably an alkyl group of 1 to 5 carbon atoms, and a methyl group, an ethyl group, a propyl group, an n-butyl group or a tert-butyl group is particularly desirable.

Examples of the halogen atom as the substituent for the aromatic hydrocarbon group include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

As the structural unit (a3), a structural unit represented by general formula (a3-1) shown below is preferable.

[Chemical Formula 43]

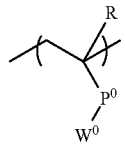

(a3-1)

In the formula, R represents a hydrogen atom, an alkyl group of 1 to 5 carbon atoms or a halogenated alkyl group of 1 to 5 carbon atoms; $P^0$ represents —C(=O)—O—, —C(=O)—$NR^0$— (wherein $R^0$ represents a hydrogen atom or an alkyl group of 1 to 5 carbon atoms) or a single bond; and $W^0$ represents —COOH or a hydrocarbon group which has at least one substituent group selected from the group consisting of —OH, —COOH, —CN, —$SO_2NH_2$ and —$CONH_2$, provided that the hydrocarbon group may have an oxygen atom or a sulfur atom at an arbitrary position, and may be substituted with a halogen atom.

In the formula (a3-1), as the alkyl group for R, a linear or branched alkyl group is preferable, and specific examples include a methyl group, an ethyl group, a propyl group, an isopropyl group, an n-butyl group, an isobutyl group, a tert-butyl group, a pentyl group, an isopentyl group and a neopentyl group.

Examples of the halogenated alkyl group for R include groups in which part or all of the hydrogen atoms within the aforementioned alkyl groups of 1 to 5 carbon atoms has been substituted with a halogen atom. Examples of the halogen atom include a fluorine atom, a chlorine atom, a bromine atom and an iodine atom, and a fluorine atom is particularly desirable.

As R, a hydrogen atom, an alkyl group of 1 to 5 carbon atoms or a fluorinated alkyl group of 1 to 5 carbon atoms is preferable, and a hydrogen atom or a methyl group is particularly desirable.

In the formula (a3-1), $P^0$ represents —C(=O)—O—, —C(=O)—$NR^0$— (wherein $R^0$ represents a hydrogen atom or an alkyl group of 1 to 5 carbon atoms) or a single bond. The alkyl group for $R^0$ is the same as defined for the alkyl group for R.

In the formula (a3-1), $W^0$ represents —COOH or a hydrocarbon group which has at least one substituent group selected from the group consisting of —OH, —COOH, —CN, —$SO_2NH_2$ and —$CONH_2$, provided that the hydrocarbon group may have an oxygen atom or a sulfur atom at an arbitrary position, and may be substituted with a halogen atom.

A "hydrocarbon group which has a substituent" refers to a hydrocarbon group in which at least part of the hydrogen atoms bonded to the hydrocarbon group is substituted with a substituent.

The hydrocarbon group for $W^0$ may be either an aliphatic hydrocarbon group, or an aromatic hydrocarbon group.

Preferable examples of the aliphatic hydrocarbon group for $W^0$ include linear or branched hydrocarbon groups of 1 to 10 carbon atoms (preferably alkylene groups) and aliphatic cyclic groups (monocyclic groups and polycyclic groups), and are the same as explained above.

The aromatic hydrocarbon group for $W^0$ is a hydrocarbon group having at least one aromatic ring, and is the same as explained above.

$W^0$ may have an oxygen atom or a sulfur atom at an arbitrary position. Here, the expression "may have an oxygen atom or a sulfur atom at an arbitrary position" means that part of the carbon atoms constituting the hydrocarbon group or the hydrocarbon group having a substituent (including the carbon atoms of the substituent part) may be substituted with an oxygen atom or a sulfur atom, or a hydrogen atom bonded to the hydrocarbon group may be substituted with an oxygen atom or a sulfur atom.

Further, the hydrocarbon group for $W^0$ may have a hydrogen atom bonded thereto substituted with a substituent. Examples of the halogen atom include a fluorine atom, a chlorine atom, a bromine atom and an iodine atom, and a fluorine atom is preferable.

Examples of $W^0$ which has an oxygen atom (O) at an arbitrary position are shown below.

[Chemical Formula 44]

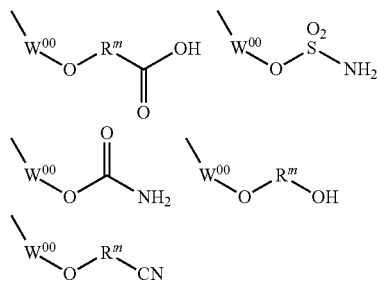

In the formulae, $W^{00}$ represents a hydrocarbon group; and $R^m$ represents an alkylene group of 1 to 5 carbon atoms.

In the formulae above, $W^{00}$ represents a hydrocarbon group, and is the same as defined for $W^0$ in the aforementioned formula (a3-1). $W^{00}$ is preferably an aliphatic hydrocarbon group, and more preferably an aliphatic cyclic group (a monocyclic group or a polycyclic group).

$R^m$ is preferably linear or branched, preferably an alkylene group of 1 to 3 carbon atoms, and more preferably a methylene group or an ethylene group.

Specific examples of preferable structural units as the structural unit (a3) include a structural unit derived from an (α-substituted) acrylate ester, and structural units represented by general formulae (a3-11) to (a3-13) shown below.

Examples of the structural unit derived from an (α-substituted) acrylate ester include a structural unit in which $P^0$ in the aforementioned formula (a3-1) is a single bond and $W^0$ is —COOH.

[Chemical Formula 43]

(a3-11)

(a3-12)

(a3-13)

In the formulae, R represents a hydrogen atom, an alkyl group of 1 to 5 carbon atoms or a halogenated alkyl group of 1 to 5 carbon atoms; $W^{01}$ represents an aromatic hydrocarbon group which has at least one substituent selected from the group consisting of —OH, —COOH, —CN, —SO$_2$NH$_2$ and —CONH$_2$; each of $P^{02}$ and $P^{03}$ independently represents —C(=O)—O—, —C(=O)—NR$^0$— (wherein R$^0$ represents a hydrogen atom or an alkyl group of 1 to 5 carbon atoms) or a single bond; $W^{02}$ represents a cyclic hydrocarbon group having at least one substituent selected from the group consisting of —OH, —COOH, —CN, —SO$_2$NH$_2$ and —CONH$_2$, provided that the hydrocarbon group may have an oxygen atom or a sulfur atom at an arbitrary position; and $W^{03}$ represents a chain-like hydrocarbon group having at least one substituent selected from the group consisting of —OH, —COOH, —CN, —SO$_2$NH$_2$ and —CONH$_2$.

[Structural Unit Represented by General Formula (a3-11)]

In the formula (a3-11), R is the same as defined for R in the aforementioned formula (a3-1).

The aromatic hydrocarbon group for $W^{01}$ is the same as defined for the aromatic hydrocarbon group for $W^0$ in the aforementioned formula (a3-1).

Specific examples of structural units preferable as a structural unit represented by general formula (a3-11) are shown below. In the formulae shown below, $R^\alpha$ represents a hydrogen atom, a methyl group or a trifluoromethyl group.

[Chemical Formula 46]

(a3-11-1)

(a3-11-2)
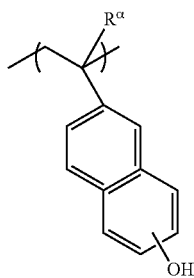

(a3-11-3)
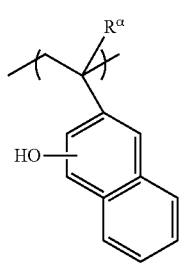

(a3-11-4)
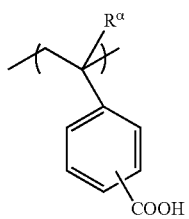

(a3-11-5)
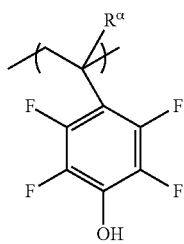

[Structural Unit Represented by General Formula (a3-12)]
In the formula (a3-12), R is the same as defined for R in the aforementioned formula (a3-1).

$P^{02}$ represents —C(=O)—O— or —C(=O)—NR⁰— (wherein R⁰ represents a hydrogen atom or an alkyl group of 1 to 5 carbon atoms), and is preferably —C(=O)—O—. The alkyl group for R⁰ is the same as defined for the alkyl group for R.

The cyclic hydrocarbon group for $W^{02}$ is the same as defined for the aliphatic cyclic groups (monocyclic groups and polycyclic groups) and aromatic hydrocarbon groups explained above for W⁰ in the aforementioned formula (a3-1).

$W^{02}$ may have an oxygen atom or a sulfur atom at an arbitrary position, and is the same as defined for W⁰ in the aforementioned formula (a3-1).

Specific examples of structural units preferable as a structural unit represented by general formula (a3-12) are shown below. In the formulae shown below, $R^{\alpha}$ represents a hydrogen atom, a methyl group or a trifluoromethyl group.

[Chemical Formula 47]

(a3-12-1)
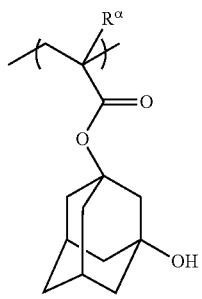

(a3-12-2)
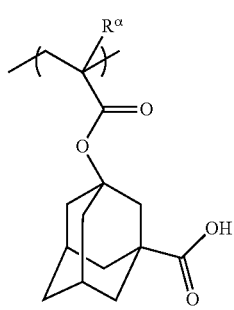

(a3-12-3)
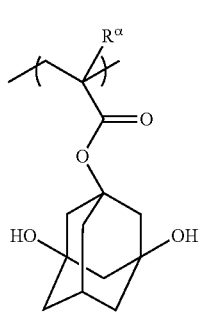

(a3-12-4)
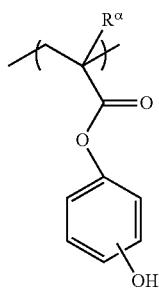

(a3-12-5)
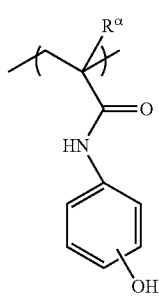

(a3-12-6)
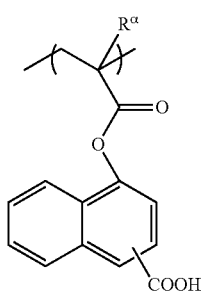
(a3-12-7)
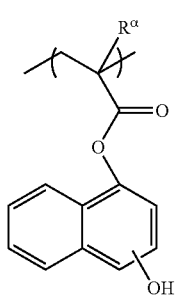
(a3-12-8)
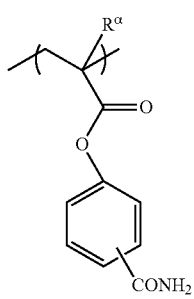
(a3-12-9)
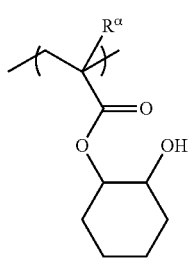
(a3-12-10)
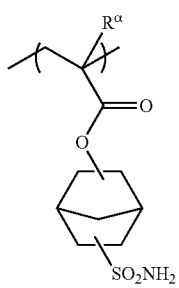
(a3-12-11)
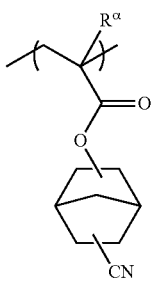
(a3-12-12)
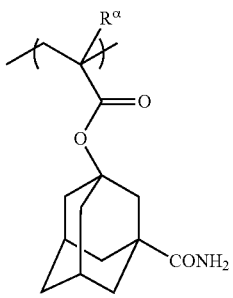
[Chemical Formula 48]
(a3-12-13)
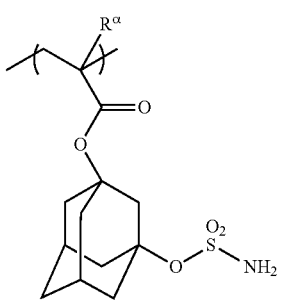
(a3-12-14)
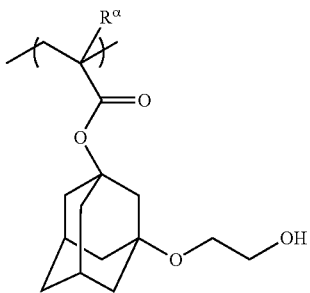
(a3-12-15)
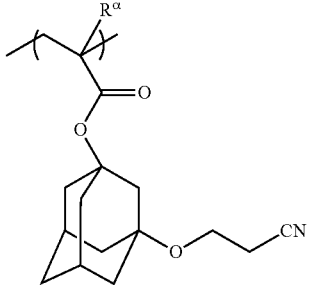

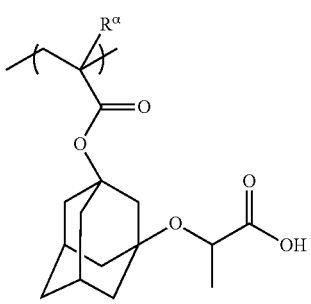

(a3-12-16)

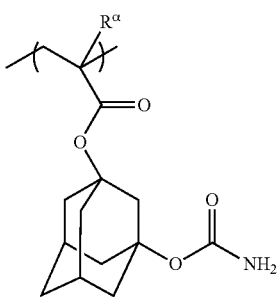

(a3-12-17)

[Structural Unit Represented by General Formula (a3-13)]

In the formula (a3-13), R is the same as defined for R in the aforementioned formula (a3-1).

$P^{o3}$ represents —C(=O)—O— or —C(=O)—NR°— (wherein R° represents a hydrogen atom or an alkyl group of 1 to 5 carbon atoms), and is preferably —C(=O)—O—. The alkyl group for R° is the same as defined for the alkyl group for R.

The chain-like hydrocarbon group for $W^{o3}$ preferably has 1 to 10 carbon atoms, more preferably 1 to 5 carbon atoms, and still more preferably 1 to 3 carbon atoms.

The chain-like hydrocarbon group for $W^{o3}$ may have a substituent (a) other than —OH, —COOH, —SO₂NH₂ and —CONH₂. Examples of the substituent (a) include an alkyl group of 1 to 5 carbon atoms, an aliphatic cyclic group (a monocyclic group or a polycyclic group), a fluorine atom, and a fluorinated alkyl group of 1 to 5 carbon atoms. The aliphatic cyclic group (a monocyclic group or a polycyclic group) for the substituent (a) preferably has 3 to 30 carbon atoms, more preferably 5 to 30 carbon atoms, still more preferably 5 to 20 carbon atoms, still more preferably 6 to 15 carbon atoms, and most preferably 6 to 12 carbon atoms. As the aliphatic cyclic group, a group in which one or more hydrogen atoms have been removed from a monocycloalkane or a polycycloalkane such as a bicycloalkane, tricycloalkane or tetracycloalkane can be used. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

Further, as exemplified by a structural unit represented by general formula (a3-13-a) shown below, the chain-like hydrocarbon group for $W^{o3}$ may have a plurality of substituents (a), and the plurality of substituents (a) may be mutually bonded to form a ring.

[Chemical Formula 49]

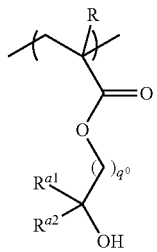

(a3-13-a)

In the formula, R represents a hydrogen atom, an alkyl group of 1 to 5 carbon atoms or a halogenated alkyl group of 1 to 5 carbon atoms; each of $R^{a1}$ and $R^{a2}$ independently represents an alkyl group of 1 to 5 carbon atoms, an aliphatic cyclic group (a monocyclic group or a polycyclic group), a fluorine atom, or a fluorinated alkyl group of 1 to 5 carbon atoms, provided that $R^{a1}$ and $R^{a2}$ may be mutually bonded to form a ring; and $q^0$ represents an integer of 1 to 4 carbon atoms.

In the formula (a3-13-a), R is the same as defined for R in the aforementioned formula (a3-1).

The aliphatic cyclic group (a monocyclic group or a polycyclic group) for $R^{a1}$ and $R^{a2}$ is the same as defined for the aliphatic cyclic group (a monocyclic group or a polycyclic group) for the substituent (a).

Further, $R^{a1}$ and $R^{a2}$ may be mutually bonded to form a ring. In such a case, a cyclic group is formed by $R^{a1}$, $R^{a2}$ and the carbon atom having $R^{a1}$ and $R^{a2}$ bonded thereto. The cyclic group may be a monocyclic group or a polycyclic group, and specific examples thereof include a group in which one or more hydrogen atoms have been removed from the monocycloalkane or polycycloalkane given as examples in the explanation of the aliphatic cyclic group (a monocyclic group or a polycyclic group) for the substituent (a).

$q^0$ is preferably 1 or 2, and more preferably 1.

Specific examples of structural units preferable as a structural unit represented by general formula (a3-13) are shown below. In the formulae shown below, $R^\alpha$ represents a hydrogen atom, a methyl group or a trifluoromethyl group.

[Chemical Formula 50]

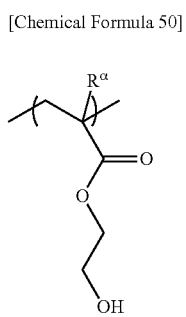

(a3-13-1)

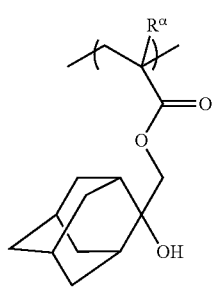

(a3-13-2)

(a3-13-3)

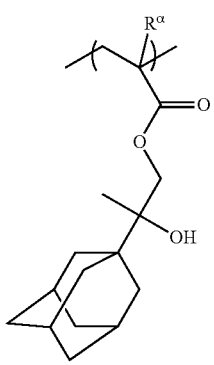

As the structural unit (a3) contained in the component (A1-1), one type of structural unit may be used, or two or more types may be used.

In the component (A1-1), the amount of the structural unit (a3) based on the combined total of all structural units constituting the component (A1-1) is preferably 5 to 50 mol %, more preferably 5 to 40 mol %, and still more preferably 5 to 25 mol %.

When the amount of the structural unit (a3) is at least as large as the lower limit of the above-mentioned range, the effect of using the structural unit (a3) (effect of improving resolution, lithography properties and pattern shape) can be satisfactorily achieved. On the other hand, when the amount of the structural unit (a3) is no more than the upper limit of the above-mentioned range, a good balance can be achieved with the other structural units.

Other Structural Units

Depending on the application, the component (A1-1) may include a structural unit other than the structural units (a5) and (a1) to (a3), as long as the effects of the present invention are not impaired.

As such a structural unit, any other structural unit which cannot be classified as the aforementioned structural units can be used without any particular limitation, and any of the multitude of conventional structural units used within resist resins for ArF excimer lasers or KrF excimer lasers (and particularly for ArF excimer lasers) can be used.

Examples of the other structural unit include a structural unit (a4) derived from an acrylate ester which may have the hydrogen atom bonded to the carbon atom on the α-position substituted with a substituent and contains an acid non-dissociable aliphatic polycyclic group.

Structural Unit (a4):

The structural unit (a4) is a structural unit derived from an acrylate ester which may have the hydrogen atom bonded to the carbon atom on the α-position substituted with a substituent and contains an acid non-dissociable aliphatic polycyclic group. When the component (A1-1) includes the structural unit (a4), lithography properties and etching resistance are improved.

In the structural unit (a4), examples of this polycyclic group include the same polycyclic groups as those described above in relation to the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecyl group, adamantyl group, tetracyclododecyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-5) shown below.

[Chemical Formula 51]

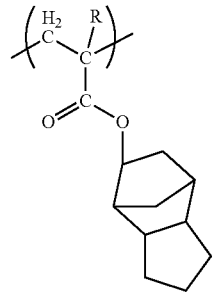
(a4-1)

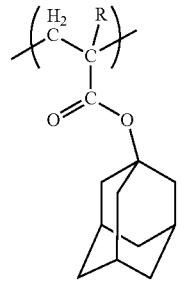
(a4-2)

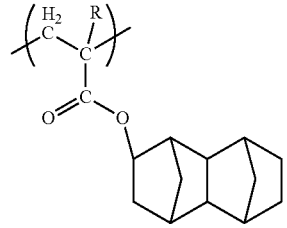
(a4-3)

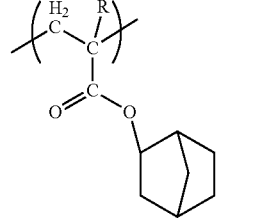
(a4-4)

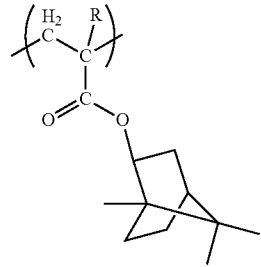
(a4-5)

In the formulae, R is the same as defined above.

When the component (A1-1) includes a structural unit (a4), as the structural unit (a4), one type of structural unit may be used, or two or more types may be used in combination.

When the structural unit (a4) is included in the component (A1-1), the amount of the structural unit (a4) based on the combined total of all the structural units that constitute the component (A1-1) is preferably within the range from 1 to 30 mol %, and more preferably from 10 to 20 mol %.

When the amount of the structural unit (a4) is at least as large as the lower limit of the above-mentioned range, the effect of using the structural unit (a4) can be satisfactorily achieved. On the other hand, when the amount of the structural unit (a4) is no more than the upper limit of the above-mentioned range, a good balance can be achieved with the other structural units.

In the present invention, the component (A) contains a polymeric compound (A1) including a structural unit (a5), and the component (A1) is preferably a polymeric compound (A1-1) which exhibits increased polarity by the action of acid.

Specific examples of the component (A1-1) include a polymeric compound consisting of a repeating structure of the structural unit (a5) and the structural unit (a1); a polymeric compound consisting of a repeating structure of the structural unit (a5), the structural unit (a1) and the structural unit (a2); and a polymeric compound consisting of a repeating structure of the structural unit (a5), the structural unit (a1), the structural unit (a2) and the structural unit (a3).

More specifically, preferable examples of the component (A1-1) include a polymeric compound consisting of a repeating structure of a structural unit represented by general formula (a5-2), a structural unit represented by general formula (a1-0-12) and a structural unit represented by general formula (a2-1); a polymeric compound consisting of a repeating structure of a structural unit represented by general formula (a5-2), a structural unit represented by general formula (a1-0-11) and a structural unit represented by general formula (a2-1); a polymeric compound consisting of a repeating structure of a structural unit represented by general formula (a5-2), a structural unit represented by general formula (a1-2) and a structural unit represented by general formula (a2-1); a polymeric compound consisting of a repeating structure of a structural unit represented by general formula (a5-2), a structural unit represented by general formula (a1-0-12) and a structural unit represented by general formula (a2-0-12); a polymeric compound consisting of a repeating structure of a structural unit represented by general formula (a5-2), a structural unit represented by general formula (a1-0-15) and a structural unit represented by general formula (a2-0-12); a polymeric compound consisting of a repeating structure of a structural unit represented by general formula (a5-2), a structural unit represented by general formula (a1-0-12), a structural unit represented by general formula (a1-0-11), a structural unit represented by general formula (a2-1) and a structural unit represented by general formula (a2-0-12); a polymeric compound consisting of a repeating structure of a structural unit represented by general formula (a5-2), a structural unit represented by general formula (a1-0-12), a structural unit represented by general formula (a2-0-12) and a structural unit represented by general formula (a3-12); a polymeric compound consisting of a repeating structure of a structural unit represented by general formula (a5-1), a structural unit represented by general formula (a1-0-12) and a structural unit represented by general formula (a2-1); and a polymeric compound consisting of a repeating structure of a structural unit represented by general formula (a5-2) and a structural unit represented by general formula (a1-0-12).

The weight average molecular weight (Mw) (the polystyrene equivalent value determined by gel permeation chromatography) of the component (A1-1) is not particularly limited, but is preferably 1,000 to 50,000, more preferably 1,500 to 30,000, and most preferably 2,000 to 20,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) is not particularly limited, but is preferably 1.0 to 5.0, more preferably 1.0 to 3.0, and most preferably 1.0 to 2.5. Here, Mn is the number average molecular weight.

The component (A1-1) can be obtained, for example, by a conventional radical polymerization or the like of the monomers corresponding with each of the structural units, using a radical polymerization initiator such as azobisisobutyronitrile (AIBN).

Furthermore, in the component (A1-1), by using a chain transfer agent such as HS—$CH_2$—$CH_2$—$CH_2$—$C(CF_3)_2$—OH, a —$C(CF_3)_2$—OH group can be introduced at the terminals of the component (A1-1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

As the monomers for deriving the corresponding structural units, commercially available monomers may be used, or the monomers may be synthesized by a conventional method.

In the component (A), as the component (A1), one type may be used alone, or two or more types may be used in combination.

In the component (A), the amount of the component (A1) based on the total weight of the component (A) is preferably 50% by weight or more, more preferably 75% by weight or more, and may even be 100% by weight.

When the amount of the component (A1) is 50% by weight or more, sensitivity, resolution and lithography properties can be more reliably improved.

The component (A) may contain a base component other than the component (A1) (hereafter, referred to as "component (A2)"), as long as the effects of the present invention are not impaired. The component (A2) is not particularly limited, and any resins and low molecular weight compounds conventionally proposed can be used.

In the resist composition of the present invention, the amount of the component (A) can be appropriately adjusted depending on the thickness of the resist film to be formed, and the like.

<Component (B)>

The component (B) is an acid-generator component, and any of the known acid generators used in conventional chemically amplified resist compositions can be used.

Examples of these acid generators are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators.

As an onium salt acid generator, a compound represented by general formula (b-1) or (b-2) shown below can be used.

[Chemical Formula 52]

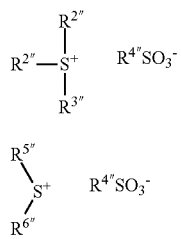

(b-1)

(b-2)

In the formulae, $R^{1\prime\prime\prime}$ to $R^{3\prime\prime\prime}$, $R^{5\prime\prime}$ and $R^{6\prime\prime}$ each independently represents an aryl group which may have a substituent, an alkyl group which may have a substituent or an alkenyl group which may have a substituent, provided that, in formula (b-1), two of $R^{1\prime\prime}$ to $R^{3\prime\prime}$ may be mutually bonded to form a ring with the sulfur atom; and $R^{4\prime\prime}$ represents an alkyl group which may have a substituent, a halogenated alkyl group which may have a substituent, an aryl group which may have a substituent or an alkenyl group which may have a substituent.

In formula (b-1), $R^{1\prime\prime}$ to $R^{3\prime\prime}$ each independently represents an aryl group which may have a substituent or an alkyl group which may have a substituent. Two of $R^{1\prime\prime}$ to $R^{3\prime\prime}$ may be mutually bonded to form a ring with the sulfur atom.

In terms of improvement in lithography properties and resist pattern shape, it is preferable that at least one of $R^{1\prime\prime}$ to $R^{3\prime\prime}$ is an aryl group, it is more preferable that two or more of $R^{1\prime\prime}$ to $R^{3\prime\prime}$ are aryl groups, and it is most preferable that all of $R^{1\prime\prime}$ to $R^{3\prime\prime}$ are aryl groups.

Examples of the aryl group for $R^{1\prime\prime}$ to $R^{3\prime\prime}$ include an unsubstituted aryl group of 6 to 20 carbon atoms; a substituted aryl group in which part or all of the hydrogen atoms of the aforementioned unsubstituted aryl group has been substituted with an alkyl group, an alkoxy group, a halogen atom, a hydroxy group, an oxo group (=O), an aryl group, an alkoxyalkyloxy group, an alkoxycarbonylalkyloxy group, —C(=O)—O—$R^{6\prime}$, —O—C(=O)—$R^{7\prime}$ or —O—$R^{8\prime}$. Each of $R^{6\prime}$, $R^{7\prime}$ and $R^{8\prime}$ independently represents a linear or branched saturated hydrocarbon group of 1 to 25 atoms, a cyclic saturated hydrocarbon group of 3 to 20 carbon atoms or a linear or branched, aliphatic unsaturated hydrocarbon group of 2 to 5 carbon atoms.

The unsubstituted aryl group for $R^{1\prime\prime}$ to $R^{3\prime\prime}$ is preferably an aryl group having 6 to 10 carbon atoms because it can be synthesized at a low cost. Specific examples thereof include a phenyl group and a naphthyl group.

The alkyl group as the substituent for the substituted aryl group represented by $R^{1\prime\prime}$ to $R^{3\prime\prime}$ is preferably an alkyl group having 1 to 5 carbon atoms, and a methyl group, an ethyl group, a propyl group, an n-butyl group, or a tert-butyl group is particularly desirable.

The alkoxy group as the substituent for the substituted aryl group is preferably an alkoxy group having 1 to 5 carbon atoms, and a methoxy group, an ethoxy group, an n-propoxy group, an iso-propoxy group, an n-butoxy group or a tert-butoxy group is particularly desirable.

The halogen atom as the substituent for the substituted aryl group is preferably a fluorine atom.

As the aryl group as the substituent for the substituted aryl group, the same aryl groups as those described above for $R^{1\prime\prime}$ to $R^{3\prime\prime}$ can be mentioned, and an aryl group of 6 to 20 carbon atoms is preferable, an aryl group of 6 to 10 carbon atoms is more preferable, and a phenyl group or a naphthyl group is still more preferable.

Examples of alkoxyalkyloxy groups as the substituent for the substituted aryl group include groups represented by a general formula shown below:

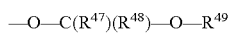

In the formula, $R^{47}$ and $R^{48}$ each independently represents a hydrogen atom or a linear or branched alkyl group; and $R^{49}$ represents an alkyl group.

The alkyl group for $R^{47}$ and $R^{48}$ preferably has 1 to 5 carbon atoms, and may be either linear or branched. As the alkyl group, an ethyl group or a methyl group is preferable, and a methyl group is most preferable.

It is preferable that at least one of $R^{47}$ and $R^{48}$ be a hydrogen atom. It is particularly desirable that at least one of $R^{47}$ and $R^{48}$ be a hydrogen atom, and the other be a hydrogen atom or a methyl group.

The alkyl group for $R^{49}$ preferably has 1 to 15 carbon atoms, and may be linear, branched or cyclic.

The linear or branched alkyl group for $R^{49}$ preferably has 1 to 5 carbon atoms. Examples thereof include a methyl group, an ethyl group, a propyl group, an n-butyl group and a tert-butyl group.

The cyclic alkyl group for $R^{49}$ preferably has 4 to 15 carbon atoms, more preferably 4 to 12, and most preferably 5 to 10. Specific examples thereof include groups in which one or more hydrogen atoms have been removed from a monocycloalkane or a polycycloalkane such as a bicycloalkane, tricycloalkane or tetracycloalkane, and which may or may not be substituted with an alkyl group of 1 to 5 carbon atoms, a fluorine atom or a fluorinated alkyl group. Examples of the monocycloalkane include cyclopentane and cyclohexane. Examples of polycycloalkanes include adamantane, norbornane, isobornane, tricyclodecane and tetracyclododecane. Among these, a group in which one or more hydrogen atoms have been removed from adamantane is preferable.

Examples of the alkoxycarbonylalkyloxy group as the substituent for the substituted aryl group include groups represented by a general formula shown below:

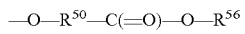

In the formula, $R^{50}$ represents a linear or branched alkylene group, and $R^{56}$ represents a tertiary alkyl group.

The linear or branched alkylene group for $R^{50}$ preferably has 1 to 5 carbon atoms, and examples thereof include a methylene group, an ethylene group, a trimethylene group, a tetramethylene group and a 1,1-dimethylethylene group.

Examples of the tertiary alkyl group for $R^{56}$ include a 2-methyl-2-adamantyl group, a 2-ethyl-2-adamantyl group, a 1-methyl-1-cyclopentyl group, a 1-ethyl-1-cyclopentyl group, a 1-methyl-1-cyclohexyl group, a 1-ethyl-1-cyclohexyl group, a 1-(1-adamantyl)-1-methylethyl group, a 1-(1-adamantyl)-1-methylpropyl group, a 1-(1-adamantyl)-1-methylbutyl group, a 1-(1-adamantyl)-1-methylpentyl group, a 1-(1-cyclopentyl)-1-methylethyl group, a 1-(1-cyclopentyl)-1-methylpropyl group, a 1-(1-cyclopentyl)-1-methylbutyl group, a 1-(1-cyclopentyl)-1-methylpentyl group, a 1-(1-cyclohexyl)-1-methylethyl group, a 1-(1-cyclohexyl)-1-methylpropyl group, a 1-(1-cyclohexyl)-1-methylbutyl group, a 1-(1-cyclohexyl)-1-methylpentyl group, a tert-butyl group, a tert-pentyl group and a tert-hexyl group.

Further, a group in which $R^{56}$ in the group represented by the aforementioned general formula: —O—$R^{50}$—C(=O)—O—$R^{56}$ has been substituted with $R^{56\prime}$ can also be mentioned. $R^{56\prime}$ represents a hydrogen atom, an alkyl group, a fluorinated alkyl group or an aliphatic cyclic group which may contain a hetero atom.

The alkyl group for $R^{56'}$ is the same as defined for the alkyl group for the aforementioned $R^{49}$.

Examples of the fluorinated alkyl group for $R^{56'}$ include groups in which part or all of the hydrogen atoms within the alkyl group for $R^{49}$ has been substituted with a fluorine atom.

Examples of the aliphatic cyclic group for $R^{56'}$ which may contain a hetero atom include an aliphatic cyclic group which does not contain a hetero atom, an alipahtic cyclic group containing a hetero atom in the ring structure, and an aliphatic cyclic group in which a hydrogen atom has been substituted with a hetero atom.

As an aliphatic cyclic group for $R^{56'}$ which does not contain a hetero atom, a group in which one or more hydrogen atoms have been removed from a monocycloalkane or a polycycloalkane such as a bicycloalkane, a tricycloalkane or a tetracycloalkane can be mentioned. Examples of the monocycloalkane include cyclopentane and cyclohexane. Examples of polycycloalkanes include adamantane, norbornane, isobornane, tricyclodecane and tetracyclododecane. Among these, a group in which one or more hydrogen atoms have been removed from adamantane is preferable.

Specific examples of the aliphatic cyclic group for $R^{56'}$ containing a hetero atom in the ring structure include groups represented by formulas (L1) to (L6) and (S1) to (S4) described later.

As the aliphatic cyclic group for $R^{56'}$ in which a hydrogen atom has been substituted with a hetero atom, an aliphatic cyclic group in which a hydrogen atom has been substituted with an oxygen atom (═O) can be mentioned.

In formulae —C(═O)—O—$R^{6'}$, —O—C(═O)—$R^{7'}$ and —O—$R^{8'}$, $R^{6'}$, $R^{7'}$ and $R^{8'}$ each independently represents a linear or branched saturated hydrocarbon group of 1 to 25 atoms, a cyclic saturated hydrocarbon group of 3 to 20 carbon atoms or a linear or branched, aliphatic unsaturated hydrocarbon group of 2 to 5 carbon atoms.

The linear or branched, saturated hydrocarbon group preferably has 1 to 25 carbon atoms, more preferably 1 to 15, and still more preferably 4 to 10.

Examples of the linear, saturated hydrocarbon group include a methyl group, an ethyl group, a propyl group, a butyl group, a pentyl group, a hexyl group, a heptyl group, an octyl group, a nonyl group and a decyl group.

Examples of the branched, saturated hydrocarbon group include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group, but excluding tertiary alkyl groups. The linear or branched, saturated hydrocarbon group may have a substituent.

Examples of the substituent include an alkoxy group, a halogen atom, a halogenated alkyl group, a hydroxyl group, an oxygen atom (═O), a cyano group and a carboxy group.

The alkoxy group as the substituent for the linear or branched saturated hydrocarbon group is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom as the substituent for the linear or branched, saturated alkyl group include a fluorine atom, a chlorine atom, a bromine atom and an iodine atom, and a fluorine atom is preferable.

Example of the halogenated alkyl group as the substituent for the linear or branched, saturated hydrocarbon group includes a group in which part or all of the hydrogen atoms within the aforementioned linear or branched, saturated hydrocarbon group have been substituted with the aforementioned halogen atoms.

The cyclic saturated hydrocarbon group of 3 to 20 carbon atoms for $R^{6'}$, $R^{7'}$ and $R^{8'}$ may be either a polycyclic group or a monocyclic group, and examples thereof include groups in which one hydrogen atom has been removed from a monocycloalkane, and groups in which one hydrogen atom has been removed from a polycycloalkane (e.g., a bicycloalkane, a tricycloalkane or a tetracycloalkane). More specific examples include groups in which one hydrogen atom has been removed from a monocycloalkane such as cyclopentane, cyclohexane, cycloheptane or cyclooctane; and groups in which one or more hydrogen atoms have been removed from a polycycloalkane such as adamantane, norbornane, isobornane, tricyclodecane or tetracyclododecane.

The cyclic, saturated hydrocarbon group may have a substituent. For example, part of the carbon atoms constituting the ring within the cyclic alkyl group may be substituted with a hetero atom, or a hydrogen atom bonded to the ring within the cyclic alkyl group may be substituted with a substituent.

In the former example, a heterocycloalkane in which part of the carbon atoms constituting the ring within the aforementioned monocycloalkane or polycycloalkane has been substituted with a hetero atom such as an oxygen atom, a sulfur atom or a nitrogen atom, and one hydrogen atom has been removed therefrom, can be used. Further, the ring may contain an ester bond (—C(═O)—O—). More specific examples include a lactone-containing monocyclic group, such as a group in which one hydrogen atom has been removed from γ-butyrolactone; and a lactone-containing polycyclic group, such as a group in which one hydrogen atom has been removed from a bicycloalkane, tricycloalkane or tetracycloalkane containing a lactone ring.

In the latter example, as the substituent, the same substituent groups as those for the aforementioned linear or branched alkyl group, or a lower alkyl group can be used.

Alternatively, $R^{6'}$, $R^{7'}$ and $R^{8'}$ may be a combination of a linear or branched alkyl group and a cyclic group.

Examples of the combination of a linear or branched alkyl group with a cyclic alkyl group include groups in which a cyclic alkyl group as a substituent is bonded to a linear or branched alkyl group, and groups in which a linear or branched alkyl group as a substituent is bonded to a cyclic alkyl group.

Examples of the linear aliphatic unsaturated hydrocarbon group for $R^{6'}$, $R^{7'}$ and $R^{8'}$ include a vinyl group, a propenyl group (an allyl group) and a butynyl group.

Examples of the branched aliphatic unsaturated hydrocarbon group for $R^{6'}$, $R^{7'}$ and $R^{8'}$ include a 1-methylpropenyl group and a 2-methylpropenyl group.

The aforementioned linear or branched, aliphatic unsaturated hydrocarbon group may have a substituent. Examples of substituents include the same substituents as those which the aforementioned linear or branched alkyl group may have.

Among the aforementioned examples, as $R^{7'}$ and $R^{8'}$, in terms of improvement in lithography properties and shape of the resist pattern, a linear or branched, saturated hydrocarbon group of 1 to 15 carbon atoms or a cyclic saturated hydrocarbon group of 3 to 20 carbon atoms is preferable.

The aryl group for each of $R^{1'''}$ to $R^{3'''}$ is preferably a phenyl group or a naphthyl group.

Examples of the alkyl group for $R^{1'''}$ to $R^{3'''}$ include linear, branched or cyclic alkyl groups of 1 to 10 carbon atoms. Among these, alkyl groups of 1 to 5 carbon atoms are preferable as the resolution becomes excellent. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decyl group, and a methyl group is most preferable because it is excellent in resolution and can be synthesized at a low cost.

The alkenyl group for $R^{1\prime\prime}$ to $R^{3\prime\prime}$ preferably has 2 to 10 carbon atoms, more preferably 2 to 5, and still more preferably 2 to 4. Specific examples thereof include a vinyl group, a propenyl group (an allyl group), a butynyl group, a 1-methylpropenyl group and a 2-methylpropenyl group.

When two of $R^{1\prime\prime}$ to $R^{3\prime\prime}$ are bonded to each other to form a ring with the sulfur atom, it is preferable that the two of to $R^{3\prime\prime}$ form a 3 to 10-membered ring including the sulfur atom, and it is particularly desirable that the two of $R^{1\prime\prime}$ to $R^{3\prime\prime}$ form a 5 to 7-membered ring including the sulfur atom.

When two of $R^{1\prime\prime}$ to $R^{3\prime\prime}$ are bonded to each other to form a ring with the sulfur atom, the remaining one of $R^{1\prime\prime}$ to $R^{3\prime\prime}$ is preferably an aryl group. As examples of the aryl group, the same as the above-mentioned aryl groups for $R^{1\prime\prime}$ to $R^{3\prime\prime}$ can be given.

Specific examples of cation moiety of the compound represented by general formula (b-1) include triphenylsulfonium, (3,5-dimethylphenyl)diphenylsulfonium, (4-(2-adamantoxymethyloxy)-3,5-dimethylphenyl) diphenylsulfonium, (4-(2-adamantoxymethyloxy)phenyl) diphenylsulfonium, (4-(tert-butoxycarbonylmethyloxy) phenyl)diphenylsulfonium, (4-(tert-butoxycarbonylmethyloxy)-3,5-dimethylphenyl) diphenylsulfonium, (4-(2-methyl-2-adamantyloxycarbonylmethyloxy)phenyl) diphenylsulfonium, (4-(2-methyl-2-adamantyloxycarbonylmethyloxy)-3,5-dimethylphenyl) diphenylsulfonium, tri(4-methylphenyl)sulfonium, dimethyl (4-hydroxynaphthyl)sulfonium, monophenyldimethylsulfonium, diphenylmonomethylsulfonium, (4-methylphenyl) diphenylsulfonium, (4-methoxyphenyl)diphenylsulfonium, tri(4-tert-butyl)phenylsulfonium, diphenyl(1-(4-methoxy) naphthyl)sulfonium, di(1-naphthyl)phenylsulfonium, 1-phenyltetrahydrothiophenium, 1-(4-methylphenyl)tetrahydrothiophenium, 1-(3,5-dimethyl-4-hydroxyphenyl) tetrahydrothiophenium, 1-(4-methoxynaphthalene-1-yl) tetrahydrothiophenium, 1-(4-ethoxynaphthalene-1-yl) tetrahydrothiophenium, 1-(4-n-butoxynaphthalene-1-yl) tetrahydrothiophenium, 1-phenyltetrahydrothiopyranium, 1-(4-hydroxyphenyl)tetrahydrothiopyranium, 1-(3,5-dimethyl-4-hydroxyphenyl)tetrahydrothiopyranium and 1-(4-methylphenyl)tetrahydrothiopyranium.

Preferable examples of the cation moiety of the compound represented by the aforementioned formula (b-1) are shown below.

[Chemical Formula 53]

(b-1-1)

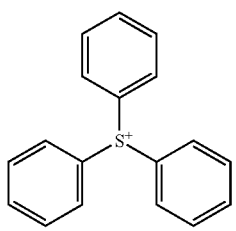

(b-1-2)

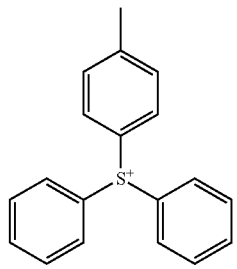

(b-1-3)

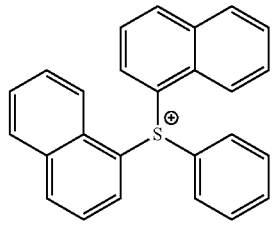

[Chemical Formula 54]

(b-1-4)

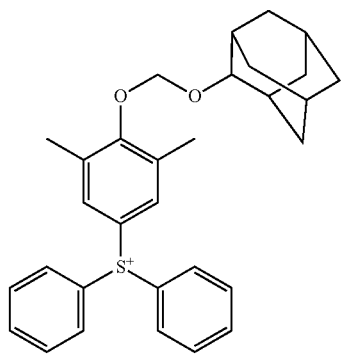

(b-1-5)

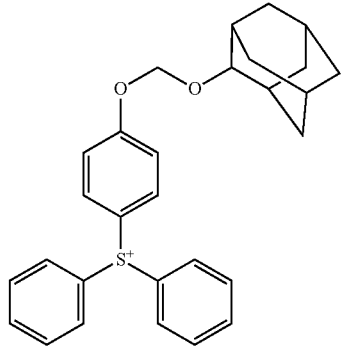

(b-1-6)

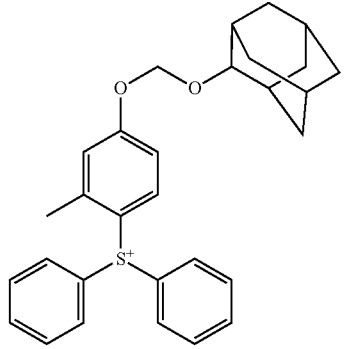

[Chemical Formula 55]
(b-1-7)
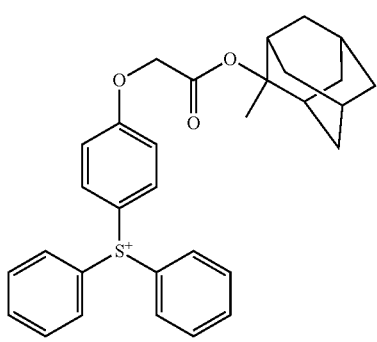
(b-1-8)
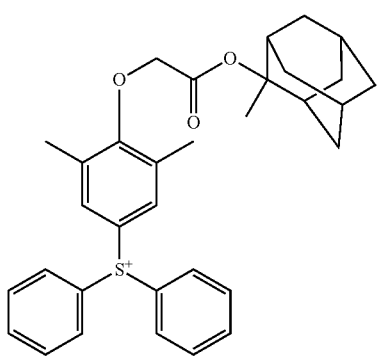
(b-1-9)
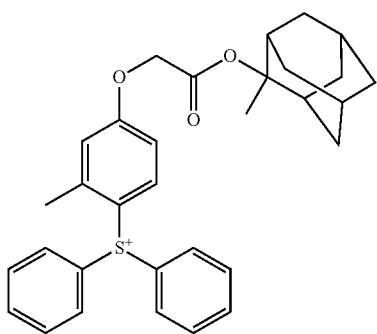
[Chemical Formula 56]
(b-1-10)
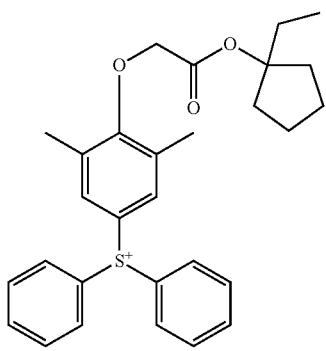
(b-1-11)
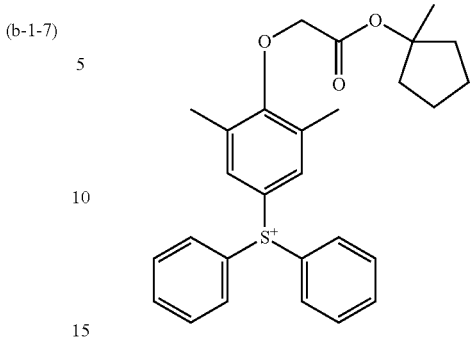
(b-1-12)
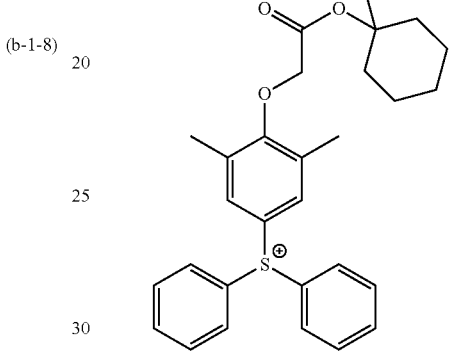
(b-1-13)
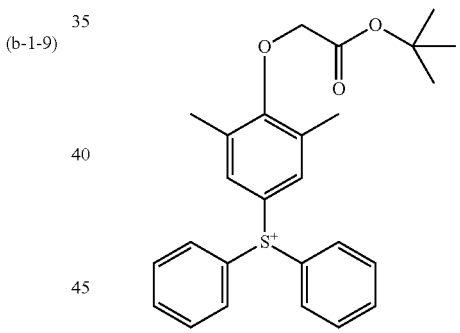
[Chemical Formula 57]
(b-1-14)
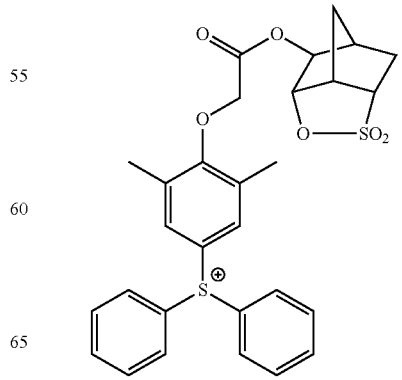

(b-1-15)
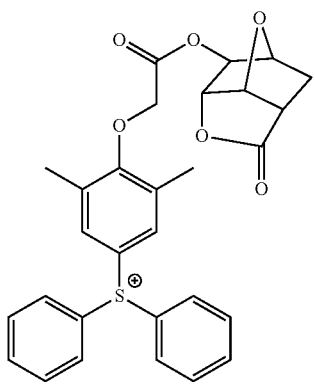
(b-1-16)
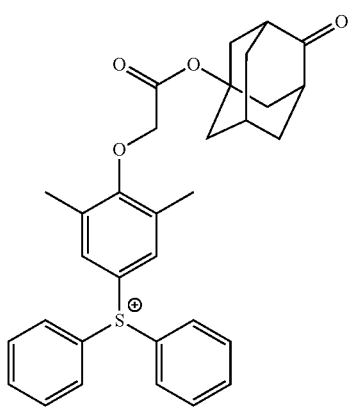
[Chemical Formula 58]
(b-1-17)
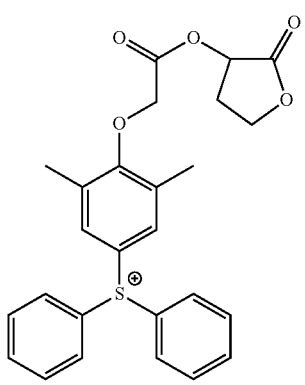
(b-1-18)
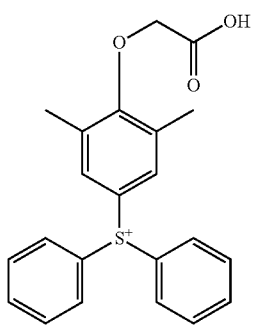
(b-1-19)
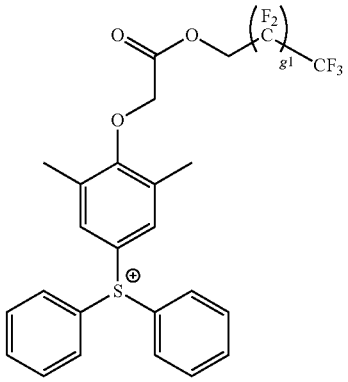
In the formula, g1 represents a recurring number, and is an integer of 1 to 5.
[Chemical Formula 59]
(b-1-20)
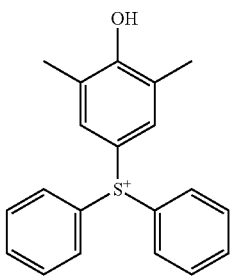
(b-1-21)
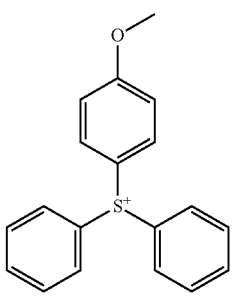
(b-1-22)
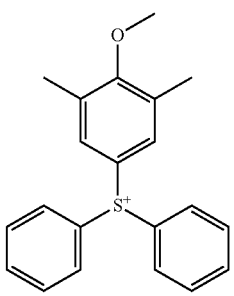

[Chemical Formula 60]
(b-1-23)
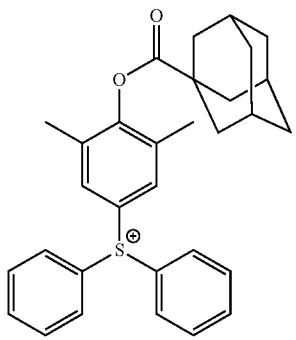
(b-1-24)
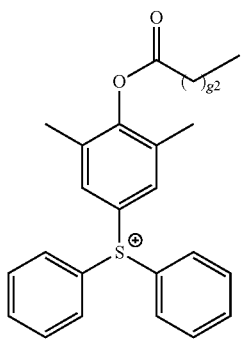
(b-1-25)
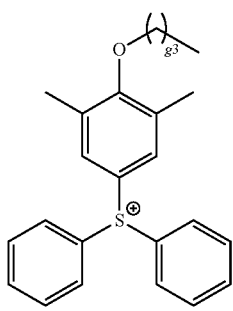
In the formula, g2 and g3 represent recurring numbers, wherein g2 is an integer of 0 to 20, and g3 is an integer of 0 to 20.
[Chemical Formula 61]
(b-1-26)
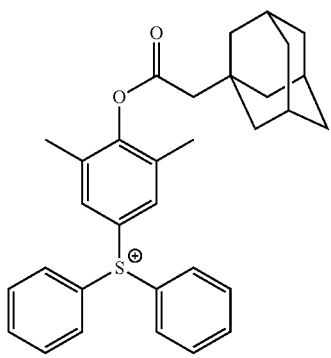
(b-1-27)
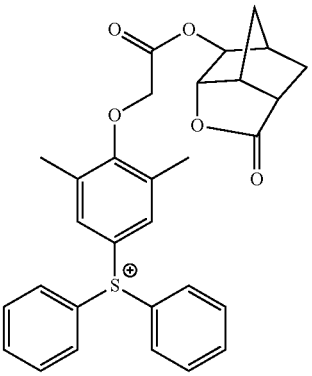
(b-1-28)
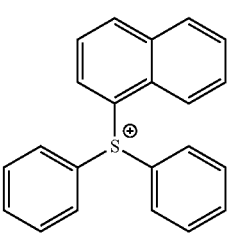
[Chemical Formula 62]
(b-1-29)
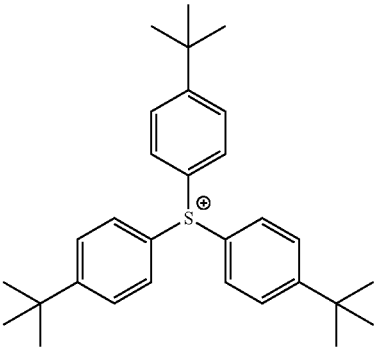
(b-1-30)
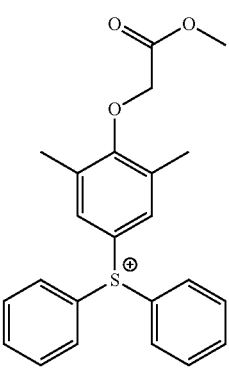

(b-1-31)

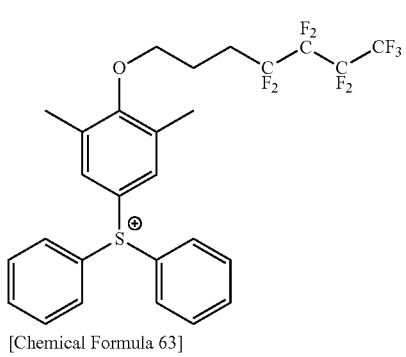

[Chemical Formula 63]

(b-1-32)

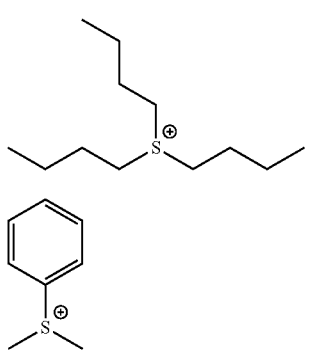

(b-1-33)

In formulas (b-1) and (b-2), $R^{4'''}$ represents an alkyl group, a halogenated alkyl group, an aryl group or an alkenyl group which may have a substituent.

The alkyl group for $R^{4'''}$ may be any of linear, branched or cyclic.

The linear or branched alkyl group preferably has 1 to 10 carbon atoms, more preferably 1 to 8 carbon atoms, and most preferably 1 to 4 carbon atoms.

The cyclic alkyl group preferably has 4 to 15 carbon atoms, more preferably 4 to 10 carbon atoms, and most preferably 6 to 10 carbon atoms.

As an example of the halogenated alkyl group for $R^{4'''}$, a group in which part of or all of the hydrogen atoms of the aforementioned linear, branched or cyclic alkyl group have been substituted with halogen atoms can be given. Examples of the aforementioned halogen atom include a fluorine atom, a chlorine atom, a bromine atom and an iodine atom, and a fluorine atom is preferable.

In the halogenated alkyl group, the percentage of the number of halogen atoms based on the total number of halogen atoms and hydrogen atoms (halogenation ratio (%)) is preferably 10 to 100%, more preferably 50 to 100%, and most preferably 100%. Higher halogenation ratio is preferable because the acid strength increases.

The aryl group for $R^{4'''}$ is preferably an aryl group of 6 to 20 carbon atoms.

The alkenyl group for $R^{4'''}$ is preferably an alkenyl group of 2 to 10 carbon atoms.

With respect to $R^{4'''}$, the expression "may have a substituent" means that part of or all of the hydrogen atoms within the aforementioned linear, branched or cyclic alkyl group, halogenated alkyl group, aryl group or alkenyl group may be substituted with substituents (atoms other than hydrogen atoms, or groups).

$R^{4'''}$ may have one substituent, or two or more substituents. Examples of the substituent include a halogen atom, a hetero atom, an alkyl group, a hydroxy group, and a group represented by the formula $X^3$-$Q^1$- (in the formula, $Q^1$ represents a divalent linking group containing an oxygen atom; and $X^3$ represents a hydrocarbon group of 3 to 30 carbon atoms which may have a substituent).

Examples of halogen atoms and alkyl groups as substituents for $R^{4'''}$ include the same halogen atoms and alkyl groups as those described above with respect to the halogenated alkyl group for $R^{4'''}$.

Examples of hetero atoms include an oxygen atom, a nitrogen atom, and a sulfur atom.

In the group represented by formula $X^3$-$Q^1$-, $Q^1$ represents a divalent linking group containing an oxygen atom.

$Q^1$ may contain an atom other than oxygen. Examples of atoms other than oxygen include a carbon atom, a hydrogen atom, a sulfur atom and a nitrogen atom.

Examples of divalent linking groups containing an oxygen atom include non-hydrocarbon, oxygen atom-containing linking groups such as an oxygen atom (an ether bond; —O—), an ester bond (—C(=O)—O—), an amido bond (—C(=O)—NH—), a carbonyl group (—C(=O)—) and a carbonate bond (—O—C(=O)—O—); and combinations of the aforementioned non-hydrocarbon, hetero atom-containing linking groups with an alkylene group.

Specific examples of the combinations of the aforementioned non-hydrocarbon, hetero atom-containing linking groups and an alkylene group include —$R^{91}$—O—, —$R^{92}$—O—C(=O)—, —C(=O)—O—$R^{93}$—O—C(=O)— (in the formulas, each of $R^{91}$ to $R^{93}$ independently represents an alkylene group).

The alkylene group for $R^{91}$ to $R^{93}$ is preferably a linear or branched alkylene group, and preferably has 1 to 12 carbon atoms, more preferably 1 to 5, and most preferably 1 to 3.

Specific examples of alkylene groups include a methylene group [—$CH_2$—]; alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$—; an ethylene group [—$CH_2CH_2$—]; alkylethylene groups such as —CH($CH_3$)$CH_2$—, —CH($CH_3$)CH($CH_3$)—, —C($CH_3$)$_2$$CH_2$— and —CH($CH_2CH_3$)$CH_2$—; a trimethylene group (n-propylene group) [—$CH_2CH_2CH_2$—]; alkyltrimethylene groups such as —CH($CH_3$)$CH_2CH_2$— and —$CH_2$CH($CH_3$)$CH_2$—; a tetramethylene group [—$CH_2CH_2CH_2CH_2$—]; alkyltetramethylene groups such as —CH($CH_3$)$CH_2CH_2CH_2$— and —$CH_2$CH($CH_3$)$CH_2CH_2$—; and a pentamethylene group [—$CH_2CH_2CH_2CH_2CH_2$—].

$Q^1$ is preferably a divalent linking group containing an ester linkage or ether linkage, and more preferably a group of —$R^{91}$—O—, —$R^{92}$—O—C(=O)— or —C(=O)—O—$R^{93}$—O—C(=O)—.

In the group represented by the formula $X^3$-$Q^1$-, the hydrocarbon group for $X^3$ may be either an aromatic hydrocarbon group or an aliphatic hydrocarbon group.

The aromatic hydrocarbon group is a hydrocarbon group having an aromatic ring. The aromatic hydrocarbon ring preferably has 3 to 30 carbon atoms, more preferably 5 to 30, still more preferably 5 to 20, still more preferably 6 to 15, and most preferably 6 to 12. Here, the number of carbon atoms within a substituent(s) is not included in the number of carbon atoms of the aromatic hydrocarbon group.

Specific examples of aromatic hydrocarbon groups include an aryl group which is an aromatic hydrocarbon ring having one hydrogen atom removed therefrom, such as a phenyl group, a biphenyl group, a fluorenyl group, a naphthyl group, an anthryl group or a phenanthryl group; and an alkylaryl group such as a benzyl group, a phenethyl group, a 1-naphthylmethyl group, a 2-naphthylmethyl group, a 1-naphthylethyl group, or a 2-naphthylethyl group. The alkyl chain within the arylalkyl group preferably has 1 to 4 carbon atom, more preferably 1 or 2, and most preferably 1.

The aromatic hydrocarbon group may have a substituent. For example, part of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

In the former example, a heteroaryl group in which part of the carbon atoms constituting the ring within the aforementioned aryl group has been substituted with a hetero atom such as an oxygen atom, a sulfur atom or a nitrogen atom, and a heteroarylalkyl group in which part of the carbon atoms constituting the aromatic hydrocarbon ring within the aforementioned arylalkyl group has been substituted with the aforementioned heteroatom can be used.

In the latter example, as the substituent for the aromatic hydrocarbon group, an alkyl group, an alkoxy group, a halogen atom, a halogenated alkyl group, a hydroxyl group, an oxygen atom (═O) or the like can be used.

The alkyl group as the substituent for the aromatic hydrocarbon group is preferably an alkyl group of 1 to 5 carbon atoms, and a methyl group, an ethyl group, a propyl group, an n-butyl group or a tert-butyl group is particularly desirable.

The alkoxy group as the substituent for the aromatic hydrocarbon group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom as the substituent for the aromatic hydrocarbon group include a fluorine atom, a chlorine atom, a bromine atom and an iodine atom, and a fluorine atom is preferable.

Example of the halogenated alkyl group as the substituent for the aromatic hydrocarbon group includes a group in which part or all of the hydrogen atoms within the aforementioned alkyl group have been substituted with the aforementioned halogen atoms.

The aliphatic hydrocarbon group for $X^3$ may be either a saturated aliphatic hydrocarbon group, or an unsaturated aliphatic hydrocarbon group. Further, the aliphatic hydrocarbon group may be linear, branched or cyclic.

In the aliphatic hydrocarbon group for $X^3$, part of the carbon atoms constituting the aliphatic hydrocarbon group may be substituted with a substituent group containing a hetero atom, or part or all of the hydrogen atoms constituting the aliphatic hydrocarbon group may be substituted with a substituent group containing a hetero atom.

As the "hetero atom" for $X^3$, there is no particular limitation as long as it is an atom other than carbon and hydrogen.

Examples of the halogen atom include a fluorine atom, a chlorine atom, an iodine atom and a bromine atom.

The substituent group containing a hetero atom may consist of a hetero atom, or may be a group containing a group or atom other than a hetero atom.

Specific examples of the substituent group for substituting part of the carbon atoms include —O—, —C(═O)—O—, —C(═O)—, —O—C(═O)—O—, —C(═O)—NH—, —NH— (the H may be replaced with a substituent such as an alkyl group or an acyl group), —S—, —S(═O)$_2$— and —S(═O)$_2$—O—. When the aliphatic hydrocarbon group is cyclic, the aliphatic hydrocarbon group may contain any of these substituent groups in the ring structure.

Examples of the substituent group for substituting part or all of the hydrogen atoms include an alkoxy group, a halogen atom, a halogenated alkyl group, a hydroxyl group, an oxygen atom (═O) and a cyano group.

The aforementioned alkoxy group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the aforementioned halogen atom include a fluorine atom, a chlorine atom, a bromine atom and an iodine atom, and a fluorine atom is preferable.

Example of the aforementioned halogenated alkyl group includes a group in which part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

As the aliphatic hydrocarbon group, a linear or branched saturated hydrocarbon group, a linear or branched monovalent unsaturated hydrocarbon group, or a cyclic aliphatic hydrocarbon group (aliphatic cyclic group) is preferable.

The linear saturated hydrocarbon group (alkyl group) preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group (alkyl group) preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The unsaturated hydrocarbon group preferably has 2 to 10 carbon atoms, more preferably 2 to 5, still more preferably 2 to 4, and most preferably 3. Examples of linear monovalent unsaturated hydrocarbon groups include a vinyl group, a propenyl group (an allyl group) and a butynyl group. Examples of branched monovalent unsaturated hydrocarbon groups include a 1-methylpropenyl group and a 2-methylpropenyl group.

Among the above-mentioned examples, as the unsaturated hydrocarbon group, a propenyl group is particularly desirable.

The aliphatic cyclic group may be either a monocyclic group or a polycyclic group. The aliphatic cyclic group preferably has 3 to 30 carbon atoms, more preferably 5 to 30, still more preferably 5 to 20, still more preferably 6 to 15, and most preferably 6 to 12.

As the aliphatic cyclic group, a group in which one or more hydrogen atoms have been removed from a monocycloalkane or a polycycloalkane such as a bicycloalkane, tricycloalkane or tetracycloalkane can be used. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

When the aliphatic cyclic group does not contain a hetero atom-containing substituent group in the ring structure thereof, the aliphatic cyclic group is preferably a polycyclic group, more preferably a group in which one or more hydrogen atoms have been removed from a polycycloalkane, and a group in which one or more hydrogen atoms have been removed from adamantane is particularly desirable.

When the aliphatic cyclic group contains a hetero atom-containing substituent group in the ring structure thereof, the hetero atom-containing substituent group is preferably —O—, —C(=O)—O—, —S—, —S(=O)$_2$— or —S(=O)$_2$—O—. Specific examples of such aliphatic cyclic groups include groups represented by formulas (L1) to (L6) and (S1) to (S4) shown below.

[Chemical Formula 64]

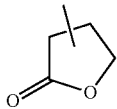
(L1)

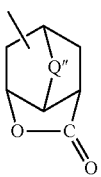
(L2)

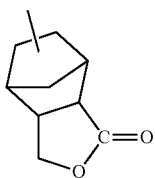
(L3)

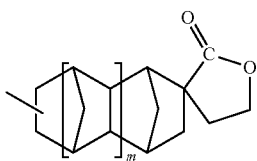
(L4)

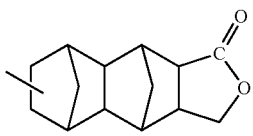
(L5)

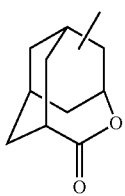
(L6)

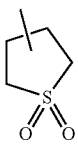
(S1)

-continued

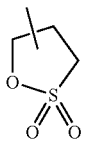
(S2)

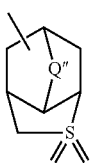
(S3)

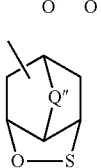
(S4)

In the formula, Q" represents an alkylene group of 1 to 5 carbon atoms, —O—, —S—, —O—R$^{94}$— or —S—R$^{95}$— (wherein each of R$^{94}$ and R$^{95}$ independently represents an alkylene group of 1 to 5 carbon atoms); and m represents 0 or 1.

As the alkylene group for Q", R$^{94}$ and R$^{95}$, the same alkylene groups as those described above for R$^{91}$ to R$^{93}$ can be used.

In these aliphatic cyclic groups, part of the hydrogen atoms bonded to the carbon atoms constituting the ring structure may be substituted with a substituent. Examples of substituents include an alkyl group, an alkoxy group, a halogen atom, a halogenated alkyl group, a hydroxyl group and an oxygen atom (=O).

As the alkyl group, an alkyl group of 1 to 5 carbon atoms is preferable, and a methyl group, an ethyl group, a propyl group, an n-butyl group or a tert-butyl group is particularly desirable.

As the alkoxy group and the halogen atom, the same groups as the substituent groups for substituting part or all of the hydrogen atoms can be used.

In the present invention, as X$^3$, a cyclic group which may have a substituent is preferable. The cyclic group may be either an aromatic hydrocarbon group which may have a substituent, or an aliphatic cyclic group which may have a substituent, and an aliphatic cyclic group which may have a substituent is preferable.

As the aromatic hydrocarbon group, a naphthyl group which may have a substituent, or a phenyl group which may have a substituent is preferable.

As the aliphatic cyclic group which may have a substituent, an aliphatic polycyclic group which may have a substituent is preferable. As the aliphatic polycyclic group, the aforementioned group in which one or more hydrogen atoms have been removed from a polycycloalkane, and a group represented by any one of the aforementioned formulae (L2) to (L6), (S3) and (S4) is preferable.

In the present invention, R$^{4'''}$ preferably has X$^3$-Q$^1$- as a substituent. In such a case, R$^{4'''}$ is preferably a group represented by the formula X$^3$-Q$^1$-Y$^{10}$— (in the formula, Q$^1$ and X$^3$ are the same as defined above; and Y$^{10}$ represents an alkylene group of 1 to 4 carbon atoms which may have a substituent, or a fluorinated alkylene group of 1 to 4 carbon atoms which may have a substituent).

In the group represented by the formula: $X^3$-$Q^1$-$Y^{10}$—, examples of the alkylene group for $Y^{10}$ include the same alkylene groups as those described above for $Q^1$ which has 1 to 4 carbon atoms.

As the fluorinated alkylene group, the aforementioned alkylene group in which part or all of the hydrogen atoms has been substituted with fluorine atoms can be used.

Specific examples of $Y^{10}$ include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, —$C(CF_3)(CF_2CF_3)$—; —$CHF$—, —$CH_2CF_2$—, —$CH_2CH_2CF_2$—, —$CH_2CF_2CF_2$—, —$CH(CF_3)CH_2$—, —$CH(CF_2CF_3)$—, —$C(CH_3)(CF_3)$—, —$CH_2CH_2CH_2CF_2$—, —$CH_2CH_2CF_2CF_2$—, —$CH(CF_3)CH_2CH_2$—, —$CH_2CH(CF_3)CH_2$—, —$CH(CF_3)CH(CF_3)$—, —$C(CF_3)_2CH_2$—; —$CH_2$—, —$CH_2CH_2$—, —$CH_2CH_2CH_2$—, —$CH(CH_3)CH_2$—, —$CH(CH_2CH_3)$—, —$C(CH_3)_2$—, —$CH_2CH_2CH_2CH_2$—, —$CH(CH_3)CH_2CH_2$—, —$CH_2CH(CH_3)CH_2$—, —$CH(CH_3)CH(CH_3)$—, —$C(CH_3)_2CH_2$—, —$CH(CH_2CH_3)CH_2$—, —$CH(CH_2CH_2CH_3)$—, and —$C(CH_3)(CH_2CH_3)$—.

$Y^{10}$ is preferably a fluorinated alkylene group, and particularly preferably a fluorinated alkylene group in which the carbon atom bonded to the adjacent sulfur atom is fluorinated. Examples of such fluorinated alkylene groups include —$CF_2$—, —$CF_2CF_2$—, —$CF_2CF_2CF_2$—, —$CF(CF_3)CF_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—; —$CH_2CF_2$—, —$CH_2CH_2CF_2$—, —$CH_2CF_2CF_2$—; —$CH_2CH_2CH_2CF_2$—, —$CH_2CH_2CF_2CF_2$—, and —$CH_2CF_2CF_2CF_2$—.

Of these, —$CF_2$—, —$CF_2CF_2$—, —$CF_2CF_2CF_2$— or $CH_2CF_2CF_2$— is preferable, —$CF_2$—, —$CF_2CF_2$— or —$CF_2CF_2CF_2$— is more preferable, and —$CF_2$— is particularly desirable.

The alkylene group or fluorinated alkylene group may have a substituent. The alkylene group or fluorinated alkylene group "has a substituent" means that part or all of the hydrogen atoms or fluorine atoms in the alkylene group or fluorinated alkylene group has been substituted with groups other than hydrogen atoms and fluorine atoms.

Examples of substituents which the alkylene group or fluorinated alkylene group may have include an alkyl group of 1 to 4 carbon atoms, an alkoxy group of 1 to 4 carbon atoms, and a hydroxyl group.

In formula (b-2), $R^{5\prime\prime\prime}$ and $R^{6\prime\prime\prime}$ each independently represents an aryl group which may have a substituent or an alkyl group which may have a substituent.

In terms of improvement in lithography properties and resist pattern shape, it is preferable that at least one of $R^{5\prime\prime\prime}$ and $R^{6\prime\prime\prime}$ is an aryl group, and it is more preferable that both $R^{5\prime\prime\prime}$ and $R^{6\prime\prime\prime}$ represent an aryl group.

As the aryl group for $R^{5\prime\prime\prime}$ and $R^{6\prime\prime\prime}$, the same aryl groups as those described above for $R^{1\prime\prime\prime}$ to $R^{3\prime\prime\prime}$ can be used.

As the alkyl group for $R^{5\prime\prime\prime}$ and $R^{6\prime\prime\prime}$, the same alkyl groups as those described above for $R^{1\prime\prime\prime}$ to $R^{3\prime\prime\prime}$ can be used.

As the alkenyl group for $R^{5\prime\prime\prime}$ and $R^{6\prime\prime\prime}$, the same as the alkenyl groups for $R^{1\prime\prime\prime}$ to $R^{3\prime\prime\prime}$ can be used.

It is particularly desirable that both of $R^{5\prime\prime\prime}$ and $R^{6\prime\prime\prime}$ represents a phenyl group.

Specific examples of the cation moiety of the compound represented by general formula (b-2) include diphenyliodonium and bis(4-tert-butylphenyl)iodonium.

As $R^{4\prime\prime\prime}$ in formula (b-2), the same groups as those mentioned above for $R^{4\prime\prime\prime}$ in formula (b-1) can be used.

Specific examples of suitable onium salt acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

Furthermore, onium salts in which the anion moiety of these onium salts are replaced by an anion moiety represented by any one of formulae (b1) to (b9) shown below can be used. Among these, it is more preferable to use onium salts in which the anion moiety of these onium salts are replaced by an anion moiety represented by any one of formulae (b3) to (b6) and (b9) shown below, and it is particularly desirable to use an onium salt in which the anion moiety has been replaced by an anion moiety represented by any formula (b9) shown below.

These anions have a structure similar to the anion moieties of the component (D1) described later. Therefore, it is presumed that, by using an onium salt in which the anion moiety is replaced by any of these anions, the effects of the present invention can be improved.

[Chemical Formula 65]

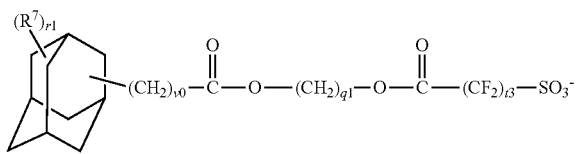
(b1)

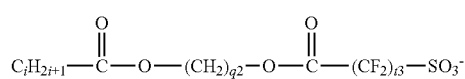
(b2)

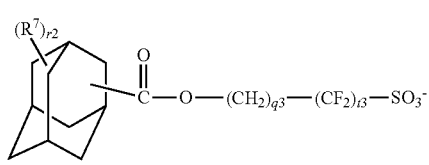
(b3)

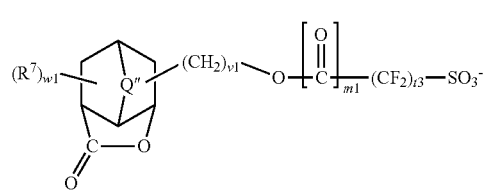
(b4)

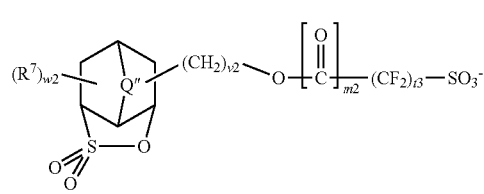
(b5)

[Chemical Formula 66]

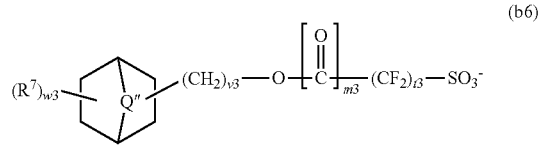
(b6)

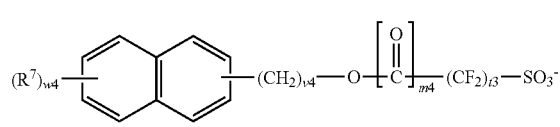
(b7)

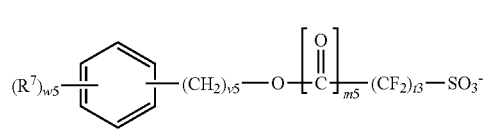
(b8)

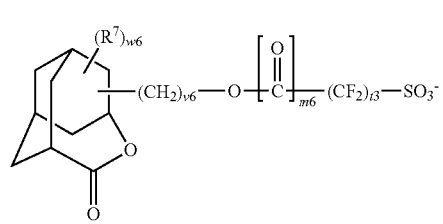
(b9)

In the formulae, q1 and q2 each independently represents an integer of 1 to 5; q3 represents an integer of 1 to 12; t3 represents an integer of 1 to 3; r1 and r2 each independently represents an integer of 0 to 3; i represents an integer of 1 to 20; $R^7$ represents a substituent; m1 to m6 each independently represents 0 or 1; v0 to v6 each independently represents an integer of 0 to 3; w1 to w6 each independently represents an integer of 0 to 3; and Q" is the same as defined above.

As the substituent for $R^7$, the same groups as those which the aforementioned aliphatic hydrocarbon group or aromatic hydrocarbon group for $X^3$ may have as a substituent can be used.

If there are two or more of the $R^7$ group, as indicated by the values r1, r2, and w1 to w6, then the two or more of the $R^7$ groups may be the same or different from each other.

Further, onium salt-based acid generators in which the anion moiety in general formula (b-1) or (b-2) is replaced by an anion represented by general formula (b-3) or (b-4) shown below (the cation moiety is the same as (b-1) or (b-2)) may be used.

[Chemical Formula 67]

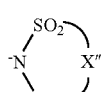
(b-3)

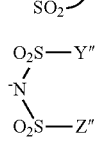
(b-4)

In the formulas, X" represents an alkylene group of 2 to 6 carbon atoms in which at least one hydrogen atom has been substituted with a fluorine atom; and each of Y" and Z" independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Each of Y" and Z" independently represents a linear or branched alkyl group in which at least one hydrogen atom has been substituted with a fluorine atom, and the alkyl group has 1 to 10 carbon atoms, preferably 1 to 7 carbon atoms, and most preferably 1 to 3 carbon atoms.

The smaller the number of carbon atoms of the alkylene group for X" or those of the alkyl group for Y" and Z" within the above-mentioned range of the number of carbon atoms, the more the solubility in a resist solvent is improved.

Further, in the alkylene group for X" or the alkyl group for Y" and Z", it is preferable that the number of hydrogen atoms substituted with fluorine atoms is as large as possible because the acid strength increases and the transparency to high energy radiation of 200 nm or less or electron beam is improved.

The fluorination ratio of the alkylene group or alkyl group is preferably from 70 to 100%, more preferably from 90 to 100%, and it is particularly desirable that the alkylene group or alkyl group be a perfluoroalkylene group or perfluoroalkyl group in which all hydrogen atoms are substituted with fluorine atoms.

Furthermore, as an onium salt-based acid generator, a sulfonium salt having a cation represented by general formula (b-5) or (b-6) shown below as the cation moiety may be used.

[Chemical Formula 68]

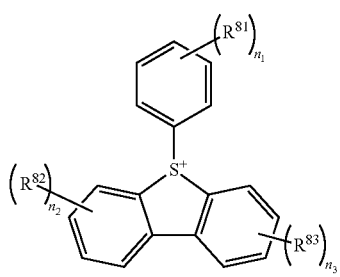
(b-5)

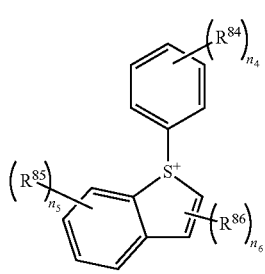
(b-6)

In formulas (b-5) and (b-6) above, each of $R^{81}$ to $R^{86}$ independently represents an alkyl group, an acetyl group, an alkoxy group, a carboxy group, a hydroxyl group or a hydroxyalkyl group; each of $n_1$ to $n_5$ independently represents an integer of 0 to 3; and $n_6$ represents an integer of 0 to 2.

With respect to $R^{81}$ to $R^{86}$, the alkyl group is preferably an alkyl group of 1 to 5 carbon atoms, more preferably a linear or branched alkyl group, and most preferably a methyl group, ethyl group, propyl group, isopropyl group, n-butyl group or tert butyl group.

The alkoxy group is preferably an alkoxy group of 1 to 5 carbon atoms, more preferably a linear or branched alkoxy group, and most preferably a methoxy group or ethoxy group.

The hydroxyalkyl group is preferably the aforementioned alkyl group in which one or more hydrogen atoms have been substituted with hydroxy groups, and examples thereof include a hydroxymethyl group, a hydroxyethyl group and a hydroxypropyl group.

If there are two or more of an individual $R^{81}$ to $R^{86}$ group, as indicated by the corresponding value of $n_1$ to $n_6$, then the two or more of the individual $R^{81}$ to $R^{86}$ group may be the same or different from each other.

$n_1$ is preferably 0 to 2, more preferably 0 or 1, and still more preferably 0.

It is preferable that $n_2$ and $n_3$ each independently represent 0 or 1, and more preferably 0.

$n_4$ is preferably 0 to 2, and more preferably 0 or 1.

$n_5$ is preferably 0 or 1, and more preferably 0.

$n_6$ is preferably 0 or 1, and more preferably 1.

Preferable examples of the cation represented by formula (b-5) or (b-6) are shown below.

[Chemical Formula 69]

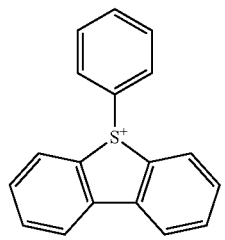
(b-5-1)

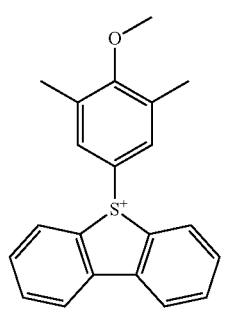
(b-5-2)

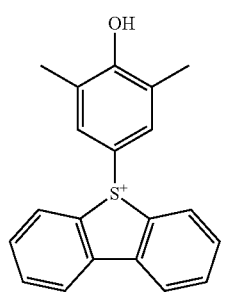
(b-5-3)

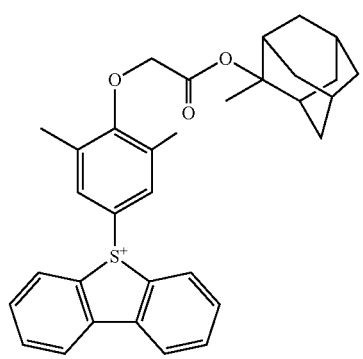
(b-5-4)

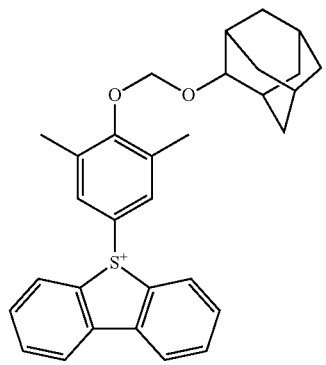
(b-5-5)

-continued

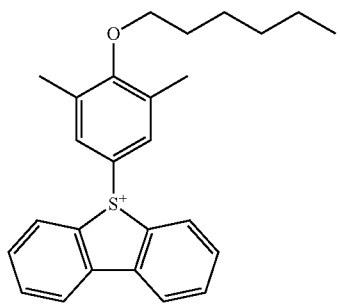
(b-5-6)

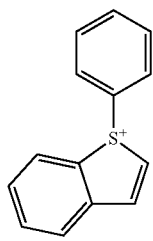
(b-6-1)

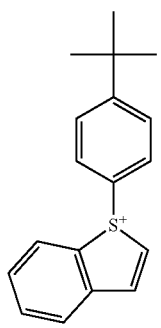
(b-6-2)

Furthermore, a sulfonium salt having a cation represented by general formula (b-7) or (b-8) shown below as the cation moiety may be used.

[Chemical Formula 70]

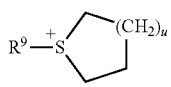
(b-7)

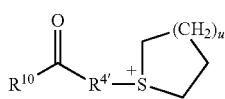
(b-8)

In formulas (b-7) and (b-8) shown below, each of $R^9$ and $R^{10}$ independently represents a phenyl group or naphthyl group which may have a substituent, an alkyl group of 1 to 5 carbon atoms, an alkoxy group or a hydroxyl group. Examples of the substituent are the same as the substituents described above in relation to the substituted aryl group for $R^{1\prime\prime\prime}$ to $R^{3\prime\prime\prime}$ (i.e., an alkyl group, an alkoxy group, an alkoxyalkyloxy group, an alkoxycarbonylalkyloxy group, a halogen atom, a hydroxy group, an oxo group (=O), an aryl group, —C(=O)—O—$R^{6\prime}$, —O—C(=O)—$R^{7\prime}$, —O—$R^{8\prime}$, a group in which $R^{56\prime}$ in the aforementioned general formula —O—$R^{50}$—C(=O)—O—$R^{56}$ has been substituted with $R^{56\prime}$).

$R^{4\prime}$ represents an alkylene group of 1 to 5 carbon atoms.

u is an integer of 1 to 3, and most preferably 1 or 2.

Preferable examples of the cation represented by formula (b-7) or (b-8) are shown below.

In the formula, $R^C$ represents a substituent described above in the explanation of the aforementioned substituted aryl group (an alkyl group, an alkoxy group, an alkoxyalkyloxy group, an alkoxycarbonylalkyloxy group, a halogen atom, a hydroxy group, an oxo group (=O), an aryl group, —C(=O)—O—$R^{6\prime}$, —O—C(=O)—$R^{7\prime}$, and —O—$R^{8\prime}$).

[Chemical Formula 71]

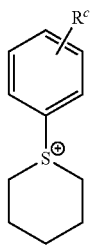
(b-7-1)

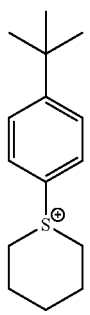
(b-7-2)

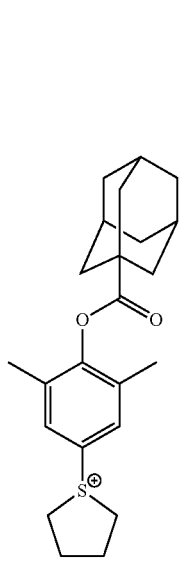
(b-7-3)

-continued

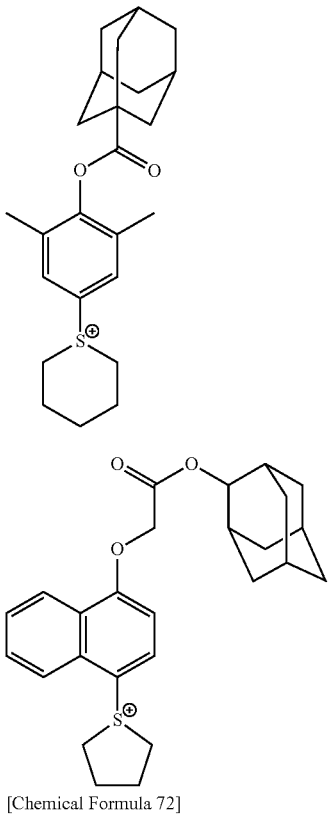

(b-7-4)

(b-7-5)

[Chemical Formula 72]

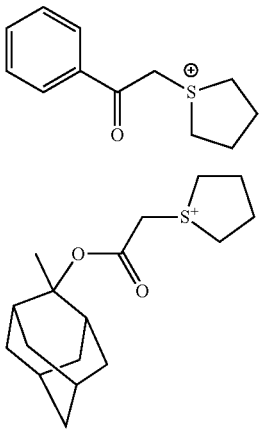

(b-8-1)

(b-8-2)

The anion moiety of the sulfonium salt having a cation moiety represented by any one of formulae (b-5) to (b-8) as a cation moiety thereof is not particularly limited, and the same anion moieties for onium salt-based acid generators which have been proposed may be used.

Examples of such anion moieties include fluorinated alkylsulfonic acid ions such as anion moieties ($R^{4"}SO_3^-$) for onium salt-based acid generators represented by general formula (b-1) or (b-2) shown above; anion moieties represented by general formula (b-3) or (b-4) shown above; and anion moieties represented by any one of the aforementioned formula (b1) to (b9).

In the present description, an oximesulfonate acid generator is a compound having at least one group represented by general formula (B-1) shown below, and has a feature of generating acid by irradiation. Such oximesulfonate acid generators are widely used for a chemically amplified resist composition, and can be appropriately selected.

[Chemical Formula 73]

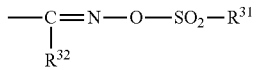

(B-1)

In the formula, each of $R^{31}$ and $R^{32}$ independently represents an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The alkyl group or the aryl group "has a substituent" means that part or all of the hydrogen atoms of the alkyl group or the aryl group is substituted with a substituent.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which part of the hydrogen atoms are substituted with halogen atoms and the "completely halogenated alkyl group" refers to an alkyl group in which all of the hydrogen atoms are substituted with halogen atoms. Examples of halogen atoms include fluorine atoms, chlorine atoms, bromine atoms and iodine atoms, and fluorine atoms are particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, partially or completely halogenated aryl group is particularly desirable. The "partially halogenated aryl group" refers to an aryl group in which some of the hydrogen atoms are substituted with halogen atoms and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, aryl group, or cyano group is preferable. Examples of the alkyl group and the aryl group for $R^{32}$ include the same alkyl groups and aryl groups as those described above for $R^{31}$.

As $R^{32}$, a cyano group, an alkyl group of 1 to 8 carbon atoms having no substituent or a fluorinated alkyl group of 1 to 8 carbon atoms is particularly desirable.

Preferred examples of the oxime sulfonate acid generator include compounds represented by general formula (B-2) or (B-3) shown below.

[Chemical Formula 74]

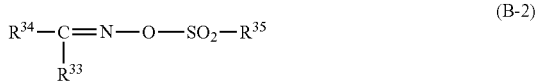
(B-2)

In the formula, $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 75]

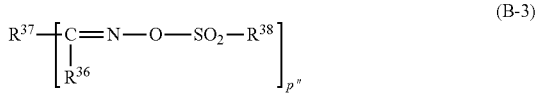
(B-3)

In the formula, $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenanthryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. Further, the halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), as the alkyl group having no substituent and the halogenated alkyl group for $R^{36}$, the same alkyl group having no substituent and the halogenated alkyl group described above for $R^{33}$ can be used.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate acid generators disclosed in Japanese Unexamined Patent Application, First Publication No. Hei 9-208554 (Chemical Formulas 18 and 19 shown in paragraphs [0012] to [0014]) and oxime sulfonate acid generators disclosed in WO 2004/074242A2 (Examples 1 to 40 described at pages 65 to 86) may be preferably used.

Furthermore, as preferable examples, the following can be used.

[Chemical Formula 76]

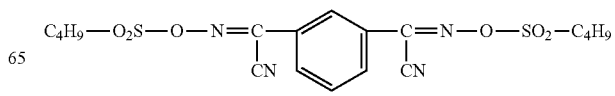

-continued

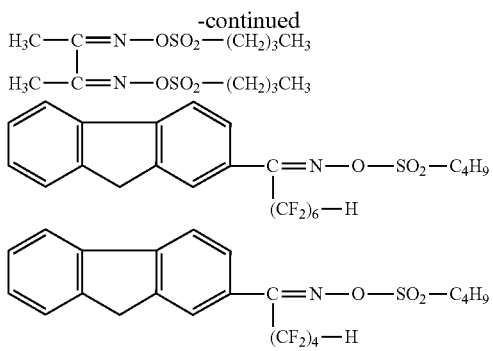

Of the aforementioned diazomethane acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, as examples of poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be given.

As the component (B), one type of acid generator may be used, or two or more types of acid generators may be used in combination.

In the resist composition of the present invention, the amount of the component (B) relative to 100 parts by weight of the component (A) is preferably 0.5 to 50 parts by weight, and more preferably 1 to 40 parts by weight.

When the amount of the component (B) is within the above-mentioned range, formation of a resist pattern can be satisfactorily performed. Further, by virtue of the above-mentioned range, a uniform solution can be obtained and the storage stability becomes satisfactory.

<Other Components>

[Component (D)]

The resist composition of the present invention may contain a basic compound (D) (hereafter referred to as the component (D)) as an optional component. The component (D) functions as an acid diffusion control agent, i.e., a quencher which traps the acid generated from the component (B) upon exposure. In the present invention, a "basic compound" refers to a compound which is basic relative to the component (A) or the component (B).

In the present invention, the component (D) may be a basic compound (D1) (hereafter, referred to as "component (D1)") which has a cation moiety and an anion moiety, or a basic compound (D2) (hereafter, referred to as "component (D2)") which does not fall under the definition of component (D1).

Component (D1)

As the component (D1), at least one member selected from the group consisting of a compound (d1-1) represented by general formula (d1-1) shown below (hereafter, referred to as "component (d1-1)"), a compound (d1-2) represented by general formula (d1-2) shown below (hereafter, referred to as "component (d1-2)") and a compound (d1-3) represented by general formula (d1-3) shown below (hereafter, referred to as "component (d1-3)").

[Chemical Formula 77]

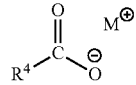 (d1-1)

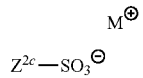 (d1-2)

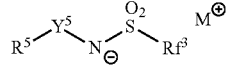 (d1-3)

In the formulae, $R^4$ represents a hydrocarbon group which may have a substituent; $Z^{2c}$ represents a hydrocarbon group of 1 to 30 carbon atoms which may have a substituent (provided that the carbon adjacent to S has no fluorine atom as a substituent); $R^5$ represents an organic group; $Y^5$ represents a linear, branched or cyclic alkylene group or an arylene group; $Rf^3$ represents a hydrocarbon group containing a fluorine atom; and each $M^+$ independently represents a sulfonium or iodonium cation having no aromaticity.

Component (d1-1)

Anion Moiety

In formula (d1-1), $R^4$ represents a hydrocarbon group which may have a substituent.

The hydrocarbon group for $R^4$ which may have a substituent may be an aliphatic hydrocarbon group or an aromatic hydrocarbon group, and the same group as $X^3$ in the formula $X^3$-$Q^1$- described above as the substituent for $R^{4''}$ in general formula "$R^{4''}SO_3^-$" in the explanation of the structural unit (a5) can be mentioned.

Among these, as the hydrocarbon group for $R^4$ which may have a substituent, an aromatic hydrocarbon group which may have a substituent or an aliphatic cyclic group which may have a substituent is preferable, and a phenyl group or a naphthyl group which may have a substituent, or a group in which one or more hydrogen atoms have been removed from a polycycloalkane such as adamantane, norbornane, isobornane, tricyclodecane or tetracyclododecane is more preferable.

As the hydrocarbon group for $R^4$ which may have a substituent, a linear or branched alkyl group or a fluorinated alkyl group is also preferable.

The linear or branched alkyl group for $R^4$ preferably has 1 to 10 carbon atoms, and specific examples thereof include a linear alkyl group such as a methyl group, an ethyl group, a propyl group, a butyl group, a pentyl group, a hexyl group, a heptyl group, an octyl group, a nonyl or a decyl group, and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group or a 4-methylpentyl group.

The fluorinated alkyl group for $R^4$ may be either chain-like or cyclic, but is preferably linear or branched.

The fluorinated alkyl group preferably has 1 to 11 carbon atoms, more preferably 1 to 8, and still more preferably 1 to 4. Specific examples include a group in which part or all of the hydrogen atoms constituting a linear alkyl group (such as a methyl group, an ethyl group, a propyl group, a butyl group, a pentyl group, a hexyl group, a heptyl group, an octyl group, a nonyl group or a decyl group) have been substituted with fluorine atom(s), and a group in which part or all of the hydrogen atoms constituting a branched alkyl group (such as a 1-methylethyl group, a 1-methylpropyl group, a 2-methylpropyl group, a 1-methylbutyl group, a 2-methylbutyl group or a 3-methylbutyl group) have been substituted with fluorine atom(s).

The fluorinated alkyl group for $R^4$ may contain an atom other than fluorine. Examples of the atom other than fluorine include an oxygen atom, a carbon atom, a hydrogen atom, an oxygen atom, a sulfur atom and a nitrogen atom.

Among these, as the fluorinated alkyl group for $R^4$, a group in which part or all of the hydrogen atoms constituting a linear alkyl group have been substituted with fluorine atom(s) is preferable, and a group in which all of the hydrogen atoms constituting a linear alkyl group have been substituted with fluorine atoms (i.e., a perfluoroalkyl group) is more preferable.

Specific examples of preferable anion moieties for the component (d1-1) are shown below.

[Chemical Formula 78]

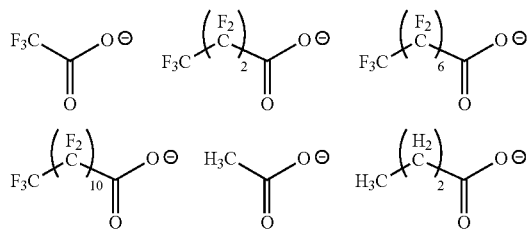
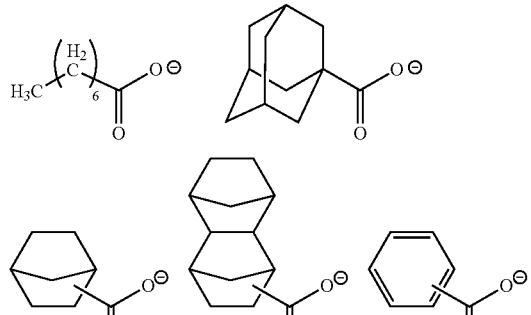
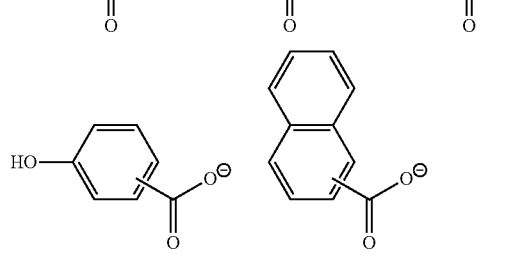

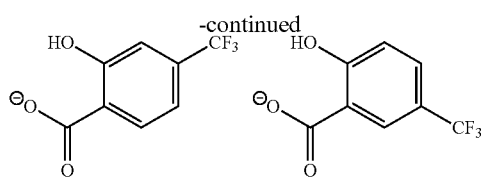

Cation Moiety

In formula (d1-1), $M^+$ represents an organic cation.

The organic cation for $M^+$ is not particularly limited, and examples thereof include the same cation moieties as those of compounds represented by the aforementioned formula (b-1) or (b-2).

As the component (d1-1), one type of compound may be used, or two or more types of compounds may be used in combination.

Component (d1-2)

Anion Moiety

In formula (d1-2), $Z^{2c}$ represents a hydrocarbon group of 1 to 30 carbon atoms which may have a substituent.

The hydrocarbon group of 1 to 30 carbon atoms for $Z^2$ which may have a substituent may be either an aliphatic hydrocarbon group or an aromatic hydrocarbon group, and is the same as defined for $R^4$ in the aforementioned formula (d1-1).

Among these, as the hydrocarbon group for $Z^{2c}$ which may have a substituent, an aliphatic cyclic group which may have a substituent is preferable, and a group in which one or more hydrogen atoms have been removed from adamantane, norbornane, isobornane, tricyclodecane, tetracyclododecane or camphor (which may have a substituent) is more preferable.

The hydrocarbon group for $Z^{2c}$ may have a substituent, and the same substituents as those described above for $X^3$ in the aforementioned formula $X^3$-$Q^1$- can be mentioned. However, in $Z^{2c}$, the carbon adjacent to the S atom within $SO_3^-$ has no fluorine atom as a substituent. By virtue of $SO_3^-$ having no fluorine atom adjacent thereto, the anion of the component (d1-2) becomes an appropriately weak acid anion, thereby improving the quenching ability of the component (D).

Specific examples of preferable anion moieties for the component (d1-2) are shown below.

[Chemical Formula 79]

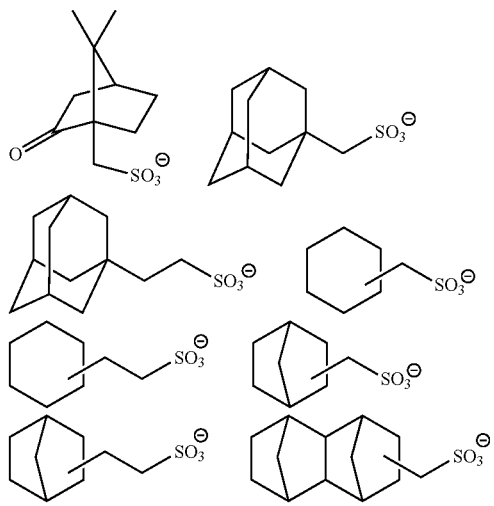

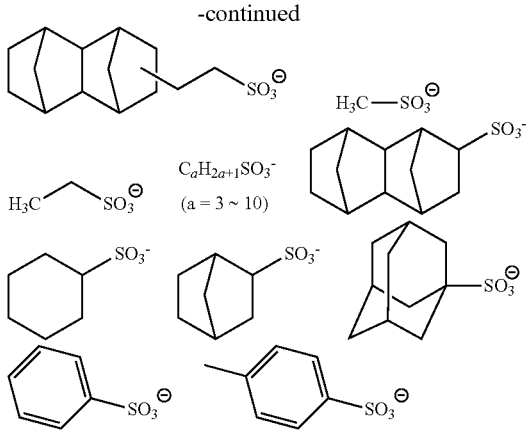

Cation Moiety

In formula (d1-2), M⁺ is the same as defined for M⁺ in the aforementioned formula (d1-1).

As the component (d1-2), one type of compound may be used, or two or more types of compounds may be used in combination.

Component (d1-3)

Anion Moiety

In formula (d1-3), $R^5$ represents an organic group.

The organic group for $R^5$ is not particularly limited, and examples thereof include an alkyl group, an alkoxy group, —O—C(=O)—C($R^{C2}$)=CH₂ ($R^{C2}$ represents a hydrogen atom, an alkyl group of 1 to 5 carbon atoms or a halogenated alkyl group of 1 to 5 carbon atoms) and —O—C(=O)—$R^{C3}$ ($R^{C3}$ represents a hydrocarbon group).

The alkyl group for $R^5$ is preferably a linear or branched alkyl group of 1 to 5 carbon atoms, and specific examples include a methyl group, an ethyl group, a propyl group, an isopropyl group, an n-butyl group, an isobutyl group, a tert-butyl group, a pentyl group, an isopentyl group, and a neopentyl group. Part of the hydrogen atoms within the alkyl group for $R^2$ may be substituted with a hydroxy group, a cyano group or the like.

The alkoxy group for $R^5$ is preferably an alkoxy group of 1 to 5 carbon atoms, and specific examples thereof include a methoxy group, an ethoxy group, an n-propoxy group, an iso-propoxy group, an n-butoxy group and a tert-butoxy group. Among these, a methoxy group and an ethoxy group are particularly desirable.

When $R^5$ is —O—C(=O)—C($R^{C2}$)=CH₂, $R^{C2}$ represents a hydrogen atom, an alkyl group of 1 to 5 carbon atoms or a halogenated alkyl group of 1 to 5 carbon atoms.

The alkyl group of 1 to 5 carbon atoms for $R^{C2}$ is preferably a linear or branched alkyl group of 1 to 5 carbon atoms, and specific examples thereof include a methyl group, an ethyl group, a propyl group, an isopropyl group, an n-butyl group, an isobutyl group, a tert-butyl group, a pentyl group, an isopentyl group and a neopentyl group.

The halogenated alkyl group for $R^{C2}$ is a group in which part or all of the hydrogen atoms of the aforementioned alkyl group of 1 to 5 carbon atoms has been substituted with halogen atoms. Examples of the halogen atom include a fluorine atom, a chlorine atom, a bromine atom and an iodine atom, and a fluorine atom is particularly desirable.

As $R^{C2}$, a hydrogen atom, an alkyl group of 1 to 3 carbon atoms or a fluorinated alkyl group of 1 to 3 carbon atoms is preferable, and a hydrogen atom or a methyl group is particularly desirable in terms of industrial availability.

When $R^5$ is —O—C(=O)—$R^{C3}$, $R^{C3}$ represents a hydrocarbon group.

The hydrocarbon group for $R^{C3}$ may be either an aromatic hydrocarbon group or an aliphatic hydrocarbon group. Specific examples of the hydrocarbon group for $R^{C3}$ include the same hydrocarbon groups as those described for $R^4$ in the aforementioned formula (d1-1).

Among these, as the hydrocarbon group for $R^{C3}$, an alicyclic group (e.g., a group in which one or more hydrogen atoms have been removed from a cycloalkane such as cyclopentane, cyclohexane, adamantane, norbornane, isobornane, tricyclodecane or tetracyclododecane) or an aromatic group (e.g., a phenyl group or a naphthyl group) is preferable. When $R^{C3}$ is an alicyclic group, the resist composition can be satisfactorily dissolved in an organic solvent, thereby improving the lithography properties. Alternatively, when $R^{C3}$ is an aromatic group, the resist composition exhibits an excellent photoabsorption efficiency in a lithography process using EUV or the like as the exposure source, thereby resulting in the improvement of the sensitivity and the lithography properties.

Among these, as $R^5$, —O—C(=O)—C($R^{C2'}$)=CH₂ ($R^{C2'}$ represents a hydrogen atom or a methyl group) or —O—C(=O)—$R^{C3'}$ ($R^{C3'}$ represents an aliphatic cyclic group) is preferable.

In formula (d1-3), $Y^5$ represents a linear, branched or cyclic alkylene group or an arylene group.

Examples of the linear, branched or cyclic alkylene group or the arylene group for $Y^5$ include the "linear or branched aliphatic hydrocarbon group", "cyclic aliphatic hydrocarbon group" and "aromatic hydrocarbon group" described above as the divalent linking group for $R^2$ in the aforementioned formula (a5-0).

Among these, as $Y^5$, an alkylene group is preferable, a linear or branched alkylene group is more preferable, and a methylene group or an ethylene group is still more preferable.

In formula (d1-3), $Rf^3$ represents a hydrocarbon group containing a fluorine atom.

The hydrocarbon group containing a fluorine atom for $Rf^3$ is preferably a fluorinated alkyl group, and more preferably the same fluorinated alkyl groups as those described above for $R^4$.

Specific examples of preferable anion moieties for the component (d1-3) are shown below.

[Chemical Formula 80]

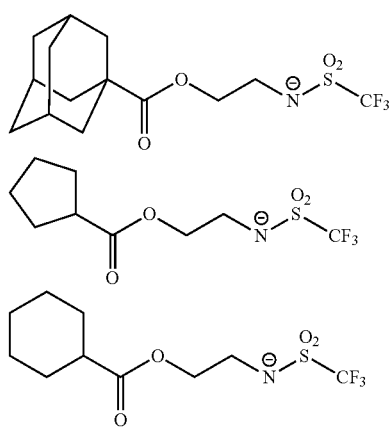

143
-continued
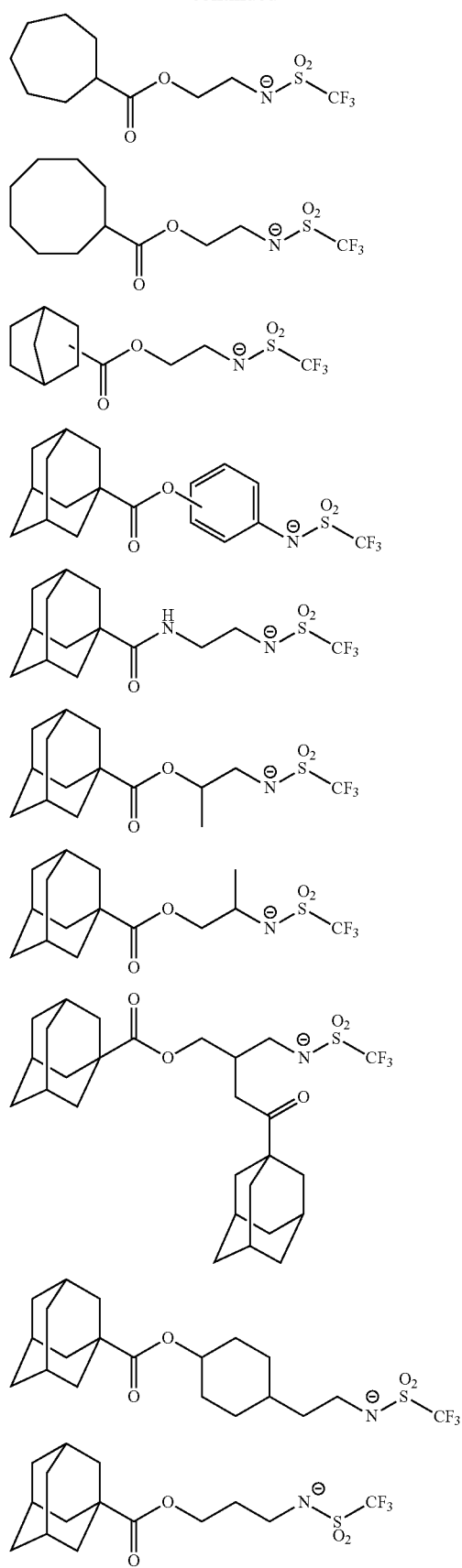
144
-continued
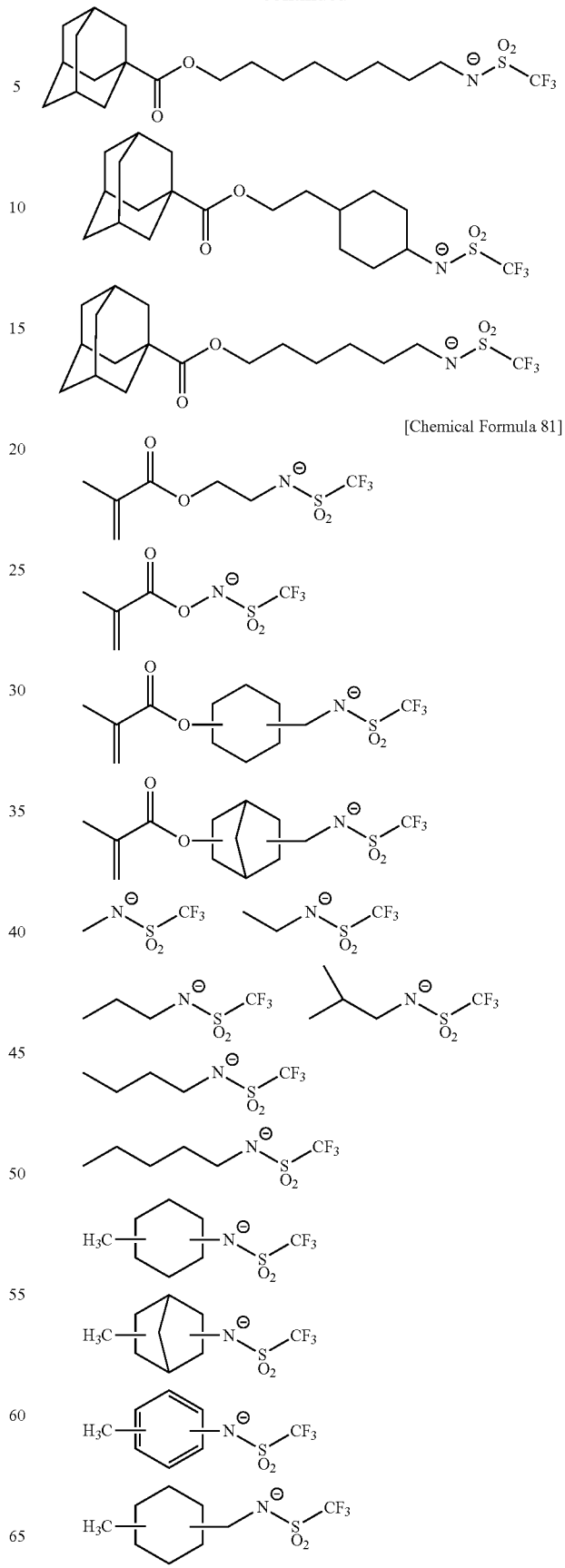
[Chemical Formula 81]

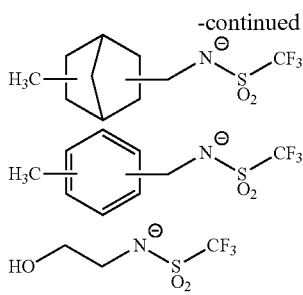

Cation Moiety

In formula (d1-3), $M^+$ is the same as defined for $M^+$ in the aforementioned formula (d1-1).

As the component (d1-3), one type of compound may be used, or two or more types of compounds may be used in combination.

The component (D1) may contain one of the aforementioned components (d1-1) to (d1-3), or at least two of the aforementioned components (d1-1) to (d1-3). In particular, it is preferable to include the component (d1-1) or the component (d1-2).

The amount of the component (D1) relative to 100 parts by weight of the component (A) is preferably within a range from 0.5 to 10 parts by weight, more preferably from 0.5 to 8 parts by weight, still more preferably from 1 to 8 parts by weight, and most preferably from 1 to 5 parts by weight.

When the amount of at least as large as the lower limit of the above-mentioned range, excellent lithography properties and excellent resist pattern shape can be obtained. On the other hand, when the amount of the component (D) is no more than the upper limit of the above-mentioned range, sensitivity can be maintained at a satisfactory level, and through-top becomes excellent.

(Production Method of Components (d1-1) to (d1-3))

The production methods of the components (d1-1) and (d1-2) are not particularly limited, and the components (d1-1) and (d1-2) can be produced by conventional methods.

The production method of the component (d1-3) is not particularly limited. For example, in the case where $R^5$ in formula (d1-3) is a group having an oxygen atom on the terminal thereof which is bonded to $Y^5$, the compound (d1-3) represented by general formula (d1-3) can be produced by reacting a compound (i-1) represented by general formula (i-1) shown below with a compound (i-2) represented by general formula (i-2) shown below to obtain a compound (i-3) represented by general formula (i-3), and reacting the compound (i-3) with a compound $Z^-M^+$ having the desired cation $M^+$, thereby obtaining the compound (d1-3).

[Chemical Formula 82]

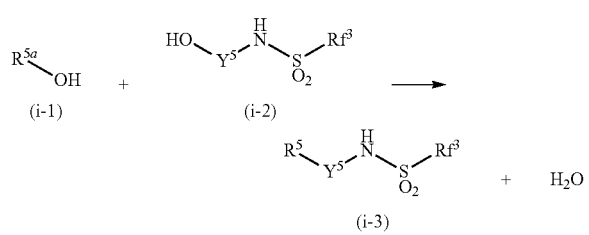

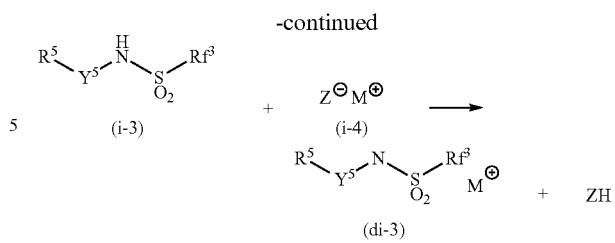

In the formulae, $R^5$, $Y^5$, $Rf^3$ and $M^+$ are respectively the same as defined for $R^5$, $Y^5$, $Rf^3$ and $M^+$ in the aforementioned general formula (d1-3); $R^{5a}$ represents a group in which the terminal oxygen atom has been removed from $R^5$; and $Z^-$ represents a counteranion.

Firstly, the compound (i-1) is reacted with the compound (i-2), to thereby obtain the compound (i-3).

In formula (i-1), $R^{5a}$ represents a group in which the terminal oxygen atom has been removed from $R^5$. In formula (i-2), $Y^5$ and $Rf^3$ are the same as defined above.

As the compound (i-1) and the compound (i-2), commercially available compounds may be used, or the compounds may be synthesized.

The method for reacting the compound (i-1) with the compound (i-2) to obtain the compound (i-3) is not particularly limited, but can be performed, for example, by reacting the compound (i-1) with the compound (i-2) in an organic solvent in the presence of an appropriate acidic catalyst, followed by washing and recovering the reaction mixture.

The acidic catalyst used in the above reaction is not particularly limited, and examples thereof include toluenesulfonic acid and the like. The amount of the acidic catalyst is preferably 0.05 to 5 moles, per 1 mole of the compound (i-2).

As the organic solvent used in the above reaction, any organic solvent which is capable of dissolving the raw materials, i.e., the compound (i-1) and the compound (i-2) can be used, and specific examples thereof include toluene and the like. The amount of the organic solvent is preferably 0.5 to 100 parts by weight, more preferably 0.5 to 20 parts by weight, relative to the amount of the compound (i-1). As the solvent, one type may be used alone, or two or more types may be used in combination.

In general, the amount of the compound (i-2) used in the above reaction is preferably 0.5 to 5 moles per 1 mole of the compound (i-1), and more preferably 0.8 to 4 moles per 1 mole of the compound (i-1).

The reaction time depends on the reactivity of the compounds (i-1) and (i-2), the reaction temperature or the like. However, in general, the reaction time is preferably 1 to 80 hours, and more preferably 3 to 60 hours.

The reaction temperature in the above reaction is preferably 20 to 200° C., and more preferably 20 to 150° C.

Next, the obtained compound (i-3) is reacted with the compound (i-4), thereby obtaining the compound (d1-3).

In formula (i-4), $M^+$ is the same as defined above, and $Z^-$ represents a counteranion.

The method for reacting the compound (i-3) with the compound (i-4) to obtain the compound (d1-3) is not particularly limited, but can be performed, for example, by dissolving the compound (i-3) in an organic solvent and water in the presence of an appropriate alkali metal hydroxide, followed by addition of the compound (i-4) and stirring.

The alkali metal hydroxide used in the above reaction is not particularly limited, and examples thereof include sodium hydroxide, potassium hydroxide and the like. The amount of the alkali metal hydroxide is preferably 0.3 to 3 moles, per 1 mole of the compound (i-3).

Examples of the organic solvent used in the above reaction include dichloromethane, chloroform, ethyl acetate and the like. The amount of the organic solvent is preferably 0.5 to 100 parts by weight, and more preferably 0.5 to 20 parts by weight, relative to the weight of the compound (i-3). As the solvent, one type may be used alone, or two or more types may be used in combination.

In general, the amount of the compound (i-4) used in the above reaction is preferably 0.5 to 5 moles per 1 mole of the compound (i-3), and more preferably 0.8 to 4 moles per 1 mole of the compound (i-3).

The reaction time depends on the reactivity of the compounds (i-3) and (i-4), the reaction temperature or the like. However, in general, the reaction time is preferably 1 to 80 hours, and more preferably 3 to 60 hours.

The reaction temperature in the above reaction is preferably 20 to 200° C., and more preferably 20 to 150° C.

After the reaction, the compound (d1-3) contained in the reaction mixture may be separated and purified. The separation and purification can be conducted by a conventional method. For example, any one of concentration, solvent extraction, distillation, crystallization, recrystallization and chromatography can be used alone, or two or more of these methods may be used in combination.

The structure of the compound (d1-3) obtained in the manner described above can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

Component (D2)

The component (D2) is not particularly limited, as long as it is a compound which is basic relative to the component (B), so as to functions as an acid diffusion control agent, i.e., a quencher which traps the acid generated from the component (B) upon exposure, and does not fall under the definition of the component (D1). As the component (D2), any of the conventionally known compounds may be selected for use. Examples thereof include an aliphatic amine and an aromatic amine. Among these, an aliphatic amine is preferable, and a secondary aliphatic amine or tertiary aliphatic amine is particularly desirable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 20 carbon atoms (i.e., alkylamines or alkylalcoholamines), cyclic amines, and other aliphatic amines.

The alkyl group within the alkylamine may be linear, branched or cyclic.

When the alkyl group is linear or branched, the alkyl group preferably has 2 to 20 carbon atoms, and more preferably 2 to 8 carbon atoms.

When the alkyl group is cyclic (i.e., a cycloalkyl group), the number of carbon atoms is preferably 3 to 30, more preferably 3 to 20, still more preferably 3 to 15, still more preferably 4 to 12, and most preferably 5 to 10. The alkyl group may be monocyclic or polycyclic. Examples thereof include groups in which one or more of the hydrogen atoms have been removed from a monocycloalkane; and groups in which one or more of the hydrogen atoms have been removed from a polycycloalkane such as a bicycloalkane, a tricycloalkane, or a tetracycloalkane. Specific examples of the monocycloalkane include cyclopentane and cyclohexane. Specific examples of the polycycloalkane include adamantane, norbornane, isobornane, tricyclodecane and tetracyclododecane.

As the alkyl group within the hydroxyalkyl group of the alkylalcoholamine, the same alkyl groups as those described above for the alkylamines can be mentioned.

Specific examples of alkylamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine.

Specific examples of alkylalcoholamines include diethanolamine, triethanolamine, diisopropanolamine, triisopropanolamine, di-n-octanolamine, tri-n-octanolamine, stearyldiethanolamine and lauryldiethanolamine.

Among these, trialkylamines of 5 to 10 carbon atoms are preferable, and tri-n-pentylamine and tri-n-octylamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine and triethanolamine tri acetate.

Examples of aromatic amines include aniline, pyridine, 4-dimethylaminopyridine, pyrrole, indole, pyrazole, imidazole and derivatives thereof, as well as diphenylamine, triphenylamine, tribenzylamine, 2,6-diisopropylaniline and N-tert-butoxycarbonylpyrrolidine.

As the component (D2), one type of compound may be used, or two or more types of compounds may be used in combination.

The component (D2) is typically used in an amount within a range from 0.01 to 5 parts by weight, relative to 100 parts by weight of the component (A). When the amount of the component (D) is within the above-mentioned range, the shape of the resist pattern and the post exposure stability of the latent image formed by the pattern-wise exposure of the resist layer are improved.

As the component (D), one type of compound may be used, or two or more types of compounds may be used in combination.

When the resist composition of the present invention contains the component (D), the amount of the component (D) (the total amount of the component (D1) and the component (D2)) relative to 100 parts by weight of the component (A) is preferably within a range from 0.1 to 15 parts by weight, more preferably from 0.3 to 12 parts by weight, and still more preferably from 0.5 to 12 parts by weight.

When the amount of the component (D) is at least as large as the lower limit of the above-mentioned range, various lithography properties such as roughness are improved. Further, a resist pattern having an excellent shape can be obtained. On the other hand, when the amount of the component (D) is no more than the upper limit of the above-mentioned range, sensitivity can be maintained at a satisfactory level, and through-top becomes excellent.

[Component (E)]

Furthermore, in the resist composition of the present invention, for preventing any deterioration in sensitivity, and improving the resist pattern shape and the post exposure stability of the latent image formed by the pattern-wise exposure of the resist layer, at least one compound (E) (hereafter referred to as "component (E)") selected from the group consisting of an organic carboxylic acid, or a phosphorus oxo acid or derivative thereof can be added.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

As the component (E), one type may be used alone, or two or more types may be used in combination.

In the present invention, when the resist composition contains the component (E), the amount of the component (E) is used in an amount within a range from 0.01 to 5 parts by weight, relative to 100 parts by weight of the component (A).

If desired, other miscible additives can also be added to the resist composition of the present invention. Examples of such miscible additives include additive resins for improving the performance of the resist film, surfactants for improving the applicability, dissolution inhibitors, plasticizers, stabilizers, colorants, halation prevention agents, and dyes.

[Component (S)]

The resist composition for immersion exposure according to the present invention can be prepared by dissolving the resist materials for the resist composition in an organic solvent (hereafter, frequently referred to as "component (S)").

The component (S) may be any organic solvent which can dissolve the respective components to give a uniform solution, and one or more kinds of any organic solvent can be appropriately selected from those which have been conventionally known as solvents for a chemically amplified resist.

Examples thereof include lactones such as γ-butyrolactone; ketones such as acetone, methyl ethyl ketone, cyclohexanone (CH), methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene.

These solvents can be used individually, or in combination as a mixed solvent.

Among these, γ-butyrolactone, propylene glycol monomethyl ether acetate (PGMEA), propylene glycol monomethyl ether (PGME), cyclohexanone (CH) and ethyl lactate (EL) are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2. For example, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably 3:7 to 7:3. Alternatively, when PGME and cyclohexanone is mixed as the polar solvent, the PGMEA:(PGME+cyclohexanone) weight ratio is preferably from 1:9 to 9:1, more preferably from 2:8 to 8:2, and still more preferably 3:7 to 7:3.

Further, as the component (S), a mixed solvent of γ-butyrolactone with PGMEA, EL or the aforementioned mixed solvent of PGMEA with a polar solvent, is also preferable. The mixing ratio (former:latter) of such a mixed solvent is preferably from 70:30 to 95:5.

The amount of the organic solvent is not particularly limited, and is appropriately adjusted to a concentration which enables coating of a coating solution to a substrate, depending on the thickness of the coating film. In general, the organic solvent is used in an amount such that the solid content of the resist composition becomes within the range from 1 to 20% by weight, and preferably from 2 to 15% by weight.

The resist composition of the present invention exhibits excellent properties with respect to sensitivity, resolution, lithography properties and etching resistance. The reason why these effects can be achieved has not been elucidated yet, but is presumed as follows.

In the resist composition of the present invention, the polymeric compound (A1) includes a structural unit (a5) represented by general formula (a5-0). The structural unit (a5) has an imino group (—NH—), and adjacent to the imino group, a carbonyl group (—C(=O)—) on one side and a carbonyl group or a thioketone (—C(=S)—) on the other side. By virtue of such a structure, the acidic proton on the nitrogen atom of the imino group functions as a proton source, and in particular, a high sensitivity can be achieved. In addition, by the presence of the nitrogen atom of the imino group, diffusion of acid generated from the component (B) upon exposure can be suppressed, and in particular, resolution and lithography properties can be improved. Furthermore, since the imino group is present in the polymeric compound, the nitrogen atom can be uniformly distributed within the resist film, and the effect of suppressing diffusion of acid can be homogeneously obtained in the entire resist film. Moreover, the presence of an aromatic ring or a polycyclic group within Y in the structural unit (a5), in particular, contributes to improving etching resistance of the resist pattern. Furthermore, by introducing an aromatic ring or a polycyclic group, the heat resistance of the resist film can be improved, thereby improving lithography properties such as pattern roughness. For the reasons as described above, it is presumed that the effects of the present invention can be achieved.

<<Method of Forming a Resist Pattern>>

The method of forming a resist pattern according to the present invention includes: forming a resist film on a substrate using a resist composition of the present invention; conducting exposure of the resist film; and developing the resist film to form a resist pattern.

The method for forming a resist pattern according to the present invention can be performed, for example, as follows.

Firstly, a resist composition of the present invention is applied to a substrate using a spinner or the like, and a bake treatment (post applied bake (PAB)) is conducted at a temperature of 80 to 150° C. for 40 to 120 seconds, preferably 60 to 90 seconds, to form a resist film.

Following selective exposure of the thus formed resist film, either by exposure through a mask having a predetermined pattern formed thereon (mask pattern) using an exposure apparatus such as an ArF exposure apparatus, an electron beam lithography apparatus or an EUV exposure apparatus, or by patterning via direct irradiation with an electron beam without using a mask pattern, baking treatment (post exposure baking (PEB)) is conducted under temperature conditions of 80 to 150° C. for 40 to 120 seconds, and preferably 60 to 90 seconds.

Next, the resist film is subjected to a developing treatment.

The developing treatment is conducted using an alkali developing solution in the case of an alkali developing process, and a developing solution containing an organic solvent (organic developing solution) in the case of a solvent developing process.

After the developing treatment, it is preferable to conduct a rinse treatment. The rinse treatment is preferably conducted using pure water in the case of an alkali developing process, and a rinse solution containing an organic solvent in the case of a solvent developing process.

In the case of a solvent developing process, after the developing treatment or the rinsing, the developing solution or the rinse liquid remaining on the pattern can be removed by a treatment using a supercritical fluid.

After the developing treatment or the rinse treatment, drying is conducted. If desired, bake treatment (post bake) can be conducted following the developing. In this manner, a resist pattern can be obtained.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) and an organic film such as a lower-layer organic film used in a multilayer resist method can be used.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film (triple-layer resist method).

The wavelength to be used for exposure is not particularly limited and the exposure can be conducted using radiation such as ArF excimer laser, KrF excimer laser, $F_2$ excimer laser, extreme ultraviolet rays (EUV), vacuum ultraviolet rays (VUV), electron beam (EB), X-rays, and soft X-rays. The resist composition of the present invention is effective to KrF excimer laser, ArF excimer laser, EB and EUV.

The exposure of the resist film can be either a general exposure (dry exposure) conducted in air or an inert gas such as nitrogen, or immersion exposure (immersion lithography).

In immersion lithography, the region between the resist film and the lens at the lowermost point of the exposure apparatus is pre-filled with a solvent (immersion medium) that has a larger refractive index than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

As an example of the alkali developing solution used in an alkali developing process, a 0.1 to 10% by weight aqueous solution of tetramethylammonium hydroxide (TMAH) can be given.

As the organic solvent contained in the organic developing solution used in a solvent developing process, any of the conventional organic solvents can be used which are capable of dissolving the component (A) (prior to exposure). Specific examples of the organic solvent include polar solvents such as ketone solvents, ester solvents, alcohol solvents, amide solvents and ether solvents, and hydrocarbon solvents.

If desired, the organic developing solution may have a conventional additive blended. Examples of the additive include surfactants. The surfactant is not particularly limited, and for example, an ionic or non-ionic fluorine and/or silicone surfactant can be used.

When a surfactant is added, the amount thereof based on the total amount of the organic developing solution is generally 0.001 to 5% by weight, preferably 0.005 to 2% by weight, and more preferably 0.01 to 0.5% by weight.

The developing treatment can be performed by a conventional developing method. Examples thereof include a method in which the substrate is immersed in the developing solution for a predetermined time (a dip method), a method in which the developing solution is cast up on the surface of the substrate by surface tension and maintained for a predetermined period (a puddle method), a method in which the developing solution is sprayed onto the surface of the substrate (spray method), and a method in which the developing solution is continuously ejected from a developing solution ejecting nozzle while scanning at a constant rate to apply the developing solution to the substrate while rotating the substrate at a constant rate (dynamic dispense method).

As the organic solvent contained in the rinse liquid used in the rinse treatment after the developing treatment in the case of a solvent developing process, any of the aforementioned organic solvents contained in the organic developing solution can be used which hardly dissolves the resist pattern. In general, at least one solvent selected from the group consisting of hydrocarbon solvents, ketone solvents, ester solvents, alcohol solvents, amide solvents and ether solvents is used. Among these, at least one solvent selected from the group consisting of hydrocarbon solvents, ketone solvents, ester solvents, alcohol solvents and amide solvents is preferable, more preferably at least one solvent selected from the group consisting of alcohol solvents and ester solvents, and an alcohol solvent is particularly desirable.

The rinse treatment using a rinse liquid (washing treatment) can be conducted by a conventional rinse method. Examples of the rinse method include a method in which the rinse liquid is continuously applied to the substrate while rotating it at a constant rate (rotational coating method), a method in which the substrate is immersed in the rinse liquid for a predetermined time (dip method), and a method in which the rinse liquid is sprayed onto the surface of the substrate (spray method).

<<Compound>>

The compound of the present invention is represented by general formula (1) shown below (hereafter, referred to as "compound (1)").

[Chemical Formula 83]

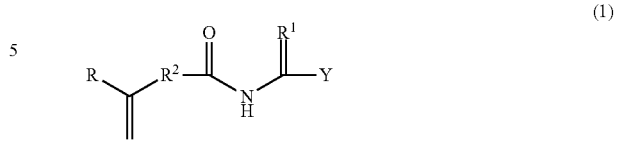

In the formula, R represents a hydrogen atom, an alkyl group of 1 to 5 carbon atoms or a halogenated alkyl group of 1 to 5 carbon atoms; $R^1$ represents a sulfur atom or an oxygen atom; $R^2$ represents a single bond or a divalent linking group; and Y represents an aromatic hydrocarbon group or an aliphatic hydrocarbon group having a polycyclic group, provided that the aromatic hydrocarbon group or the aliphatic hydrocarbon may have a carbon atom or a hydrogen atom thereof substituted with a substituent.

In the formula (1), R, $R^1$, $R^2$ and Y are respectively the same as defined for R, $R^1$, $R^2$ and Y in the aforementioned formula (a5-0).

The compound (1) is useful as a monomer for producing the component (A1).

(Production Method of Compound (1))

The production method of the compound (1) of the present invention is not particularly limited. For example, the compound (1) can be produced by reacting a compound (1-1) represented by formula (1-1) shown below with a compound (1-2) represented by formula (1-2) shown below.

[Chemical Formula 84]

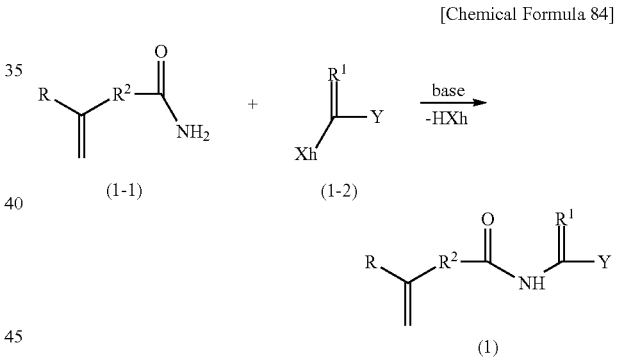

In the formulae, R, $R^1$, $R^2$ and Y are respectively the same as defined for R, $R^1$, $R^2$ and Y in the aforementioned formula (a5-0); and Xh represents a halogen atom.

In the formula (1-2), Xh represents a halogen atom, and examples thereof include a fluorine atom, a chlorine atom, a bromine atom and an iodine atom, and a chlorine atom is preferable.

The compound (1-1) can be reacted with the compound (1-2), for example, as follows. The compound (1-1) is dissolved in an appropriate organic solvent, followed by stirring in the presence of an appropriate base. Then, the compound (1-2) is added thereto and stirred, followed by washing and recovering the reaction mixture.

As a compound (1-1) and a compound (1-2), commercially available compounds can be used. Alternatively, a compound (1-1) and a compound (1-2) can be synthesized.

In the above reaction, as the organic solvent, tetrahydrofuran, tert-butylmethylether, dichloromethane (methylene chloride), acetonitrile, chloroform or the like is preferable, and the amount of the organic solvent, relative to 100 parts by weight of the compound (1-1) is preferably 0.5 to 100 parts by weight, and more preferably 0.5 to 20 parts by weight. As the organic solvent, one type may be used alone, or two or more types may be used in combination.

Examples of the base include sodium hydride, $K_2CO_3$, $Cs_2CO_3$, lithium diisopropylamide (LiDA), triethylamine and 4-dimethylaminopyridine. These bases may be used individually or in a combination of two or more. The base may be used in a catalyst amount. In general, the amount of the base is 0.01 to 10 moles, per 1 mole of the compound (1-1).

The reaction time depends on the reactivity of the compounds (1-1) and (1-2), the reaction temperature or the like. However, in general, the reaction time is preferably 0.1 to 100 hours, and more preferably 0.5 to 50 hours.

The reaction temperature in the above reaction is preferably 0 to 50° C., and more preferably 0 to 30° C.

In general, the amount of the compound (1-2) used in the above reaction is preferably 0.5 to 10 moles per 1 mole of the compound (1-1), and more preferably 0.5 to 5 moles per 1 mole of the compound (1-1).

After the reaction, the compound (1) within the reaction mixture may be separated and purified.

The separation and purification can be conducted by a conventional method. For example, any one of concentration, solvent extraction, distillation, crystallization, recrystallization and chromatography can be used alone, or two or more of these methods may be used in combination.

The structure of the compound (1) obtained in the manner described above can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

<<Polymeric Compound>>

The polymeric compound of the present invention includes a structural unit (a5) represented by general formula (a5-0) shown below.

[Chemical Formula 85]

(a5-0)

In the formula, R represents a hydrogen atom, an alkyl group of 1 to 5 carbon atoms or a halogenated alkyl group of 1 to 5 carbon atoms; $R^1$ represents a sulfur atom or an oxygen atom; $R^2$ represents a single bond or a divalent linking group; and Y represents an aliphatic hydrocarbon group having an aromatic hydrocarbon group or a polycyclic group, provided that the aromatic hydrocarbon group or the polycyclic group may have a carbon atom or a hydrogen atom thereof substituted with a substituent.

In the polymeric compound of the present invention, the amount of the structural unit (a5), based on the combined total of all the structural units that constitute the polymeric compound is preferably 5 to 70 mol %.

It is preferable that the polymeric compound of the present invention further includes a structural unit (a1)) containing an acid decomposable group that exhibits increased polarity by the action of acid.

The explanation of the polymeric compound of the present invention is the same as the explanation of the component (A1) of the resist composition of the present invention described above.

The polymeric compound of the present invention is preferable as a base resin of a resist composition.

EXAMPLES

As follows is a description of examples of the present invention, although the scope of the present invention is by no way limited by these examples.

In the following examples, a compound represented by a chemical formula (1) is designated as "compound (1)", and the same applies for compounds represented by other chemical formulae.

Monomer Synthesis Example: Examples 1 to 9

Example 1

90.0 g of methacrylamide was dissolved in 1,350 g of tetrahydrofuran (THF), and 944 mL of a 1.12 mol/L lithium diisopropylamide (LiDA) solution was dropwise added thereto at 5° C., followed by stirring for 10 minutes. Subsequently, 900 g of THF having 231.1 g of 1-adamantanecarbonyl chloride dissolved therein was added thereto, followed by stirring at 5° C. for 18 hours. After completion of the reaction, THF and t-butylmethylether (TBME) were added thereto, followed by washing with a 1 wt % aqueous hydrochloric acid solution and pure water, and concentration under reduced pressure. n-hexane was added to the obtained solution, and crystallization was conducted at 5° C., followed by filtration. The obtained solid was dried under reduced pressure, thereby obtaining 194.4 g of 1-adamantanecarboxylic acid methacrylamide (compound (51)).

With respect to the obtained compound (51), the results of the proton nuclear magnetic resonance spectrum ($^1$H-NMR) are shown below.

$^1$H-NMR (DMSO-d6, internal standard: tetramethylsilane): δ=9.85 ppm (br s, 1H), 5.57 ppm (s, 1H), 5.51 ppm (s, 1H), 1.98 ppm (m, 3H), 1.86 ppm (m, 9H), 1.61 ppm (m, 6H)

[Chemical Formula 86]

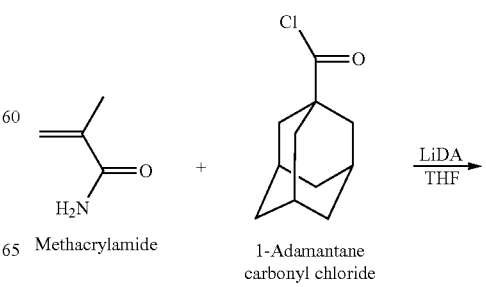

Methacrylamide    1-Adamantane carbonyl chloride

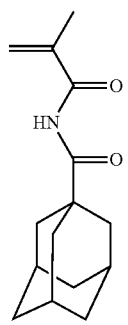

Compound (51)

Example 2

The same procedure as in Example 1 was performed, thereby obtaining a compound (52).

With respect to the obtained compound (52), the results of the proton nuclear magnetic resonance spectrum ($^1$H-NMR) are shown below.

$^1$H-NMR (DMSO-d6, internal standard: tetramethylsilane): δ=9.08 ppm (br s, 1H), 6.21 ppm (s, 1H), 5.62 ppm (s, 1H), 4.95 ppm (s, 2H), 2.10 ppm (m, 3H), 1.95 ppm (s, 3H), 1.71 ppm (m, 6H), 1.56 ppm (m, 6H)

Example 3

The same procedure as in Example 1 was performed, thereby obtaining a compound (53).

With respect to the obtained compound (53), the results of the proton nuclear magnetic resonance spectrum ($^1$H-NMR) are shown below.

$^1$H-NMR (DMSO-d6, internal standard: tetramethylsilane): δ=9.76 ppm (br s, 1H), 5.58 ppm (s, 1H), 5.46 ppm (s, 1H), 2.53 ppm (s, 2H), 1.92 ppm (m, 6H), 1.57 ppm (m, 6H), 1.50 ppm (m, 6H)

Example 4

The same procedure as in Example 1 was performed, thereby obtaining a compound (54).

With respect to the obtained compound (54), the results of the proton nuclear magnetic resonance spectrum ($^1$H-NMR) are shown below.

$^1$H-NMR (DMSO-d6, internal standard: tetramethylsilane): δ=10.08 ppm (br s, 1H), 5.85 ppm (s, 1H), 5.37 ppm (s, 1H), 2.48-1.70 ppm (m, 7H), 1.13 ppm (s, 3H), 1.06 ppm (s, 3H), 0.97 ppm (s, 3H)

Example 5

The same procedure as in Example 1 was performed, thereby obtaining a compound (55).

With respect to the obtained compound (55), the results of the proton nuclear magnetic resonance spectrum ($^1$H-NMR) are shown below.

$^1$H-NMR (DMSO-d6, internal standard: tetramethylsilane): δ=10.10 ppm (br s, 1H), 8.50-7.47 ppm (m, 7H), 5.58 ppm (s, 1H), 5.51 ppm (s, 1H), 1.93 ppm (s, 3H)

Example 6

The same procedure as in Example 1 was performed, thereby obtaining a compound (56).

With respect to the obtained compound (56), the results of the proton nuclear magnetic resonance spectrum ($^1$H-NMR) are shown below.

$^1$H-NMR (DMSO-d6, internal standard: tetramethylsilane): δ=10.01 ppm (br s, 1H), 7.98-7.45 ppm (s, 5H), 5.60 ppm (s, 1H), 5.55 ppm (s, 1H), 1.85 ppm (s, 3H)

Example 7

The same procedure as in Example 1 was performed, thereby obtaining a compound (57).

With respect to the obtained compound (57), the results of the proton nuclear magnetic resonance spectrum ($^1$H-NMR) are shown below.

$^1$H-NMR (DMSO-d6, internal standard: tetramethylsilane): δ=10.12 ppm (br s, 1H), 5.63 ppm (s, 1H), 5.56 ppm (s, 1H), 2.26 ppm (s, 6H), 2.19 ppm (s, 3H), 2.04 ppm (s, 6H), 1.87 ppm (s, 3H)

Example 8

The same procedure as in Example 1 was performed, thereby obtaining a compound (58).

With respect to the obtained compound (58), the results of the proton nuclear magnetic resonance spectrum ($^1$H-NMR) are shown below.

$^1$H-NMR (DMSO-d6, internal standard: tetramethylsilane): δ=11.01 ppm (br s, 1H), 5.82 ppm (s, 1H), 5.66 ppm (s, 1H)

Example 9

The same procedure as in Example 1 was performed, thereby obtaining a compound (59).

With respect to the obtained compound (59), the results of the proton nuclear magnetic resonance spectrum ($^1$H-NMR) are shown below.

$^1$H-NMR (DMSO-d6, internal standard: tetramethylsilane): δ=11.84 ppm (br s, 1H), 6.04 ppm (s, 1H), 5.85 ppm (s, 1H)

The structure of the obtained compounds (52) to (59) are shown below.

[Chemical Formula 87]

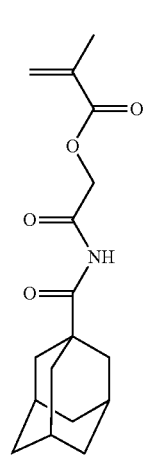

(52)

-continued (53)

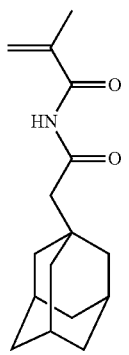

(54)

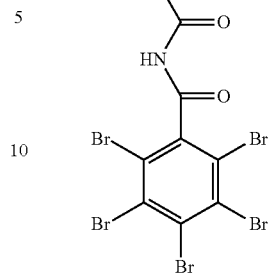

(55)

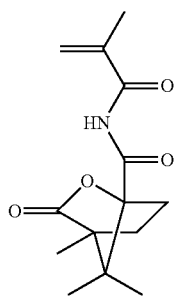

(56)

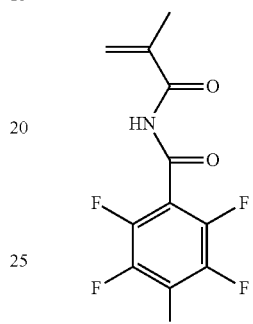

(58)

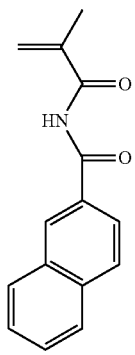

(59)

(57)

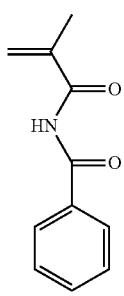

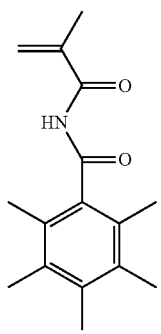

Polymer Synthesis Examples

Examples 10 to 26, Comparative Examples 1 and 2

Example 10

In a separable flask equipped with a thermometer, a reflux tube and a nitrogen feeding pipe, 25.4 g (96.82 mmol) of a compound (11) was dissolved in a mixed solvent containing 18.79 g of methyl ethyl ketone (MEK) and 18.79 g of cyclohexanone (CH), and heated to 80° C. To the resulting solution was added a solution obtained by dissolving 10.00 g (58.77 mmol) of a compound (21), 6.35 g (24.20 mmol) of a compound (11), 10.48 mmol (42.38 mmol) of the compound (51) and 24.44 mmol of dimethyl 2,2'-azobis(isobutyrate) (V-601) as a polymerization initiator in 44.88 g of MEK and 44.88 g of CH in a dropwise manner over 4 hours in a nitrogen atmosphere.

Thereafter, the reaction solution was heated for 1 hour while stirring, and then cooled to room temperature. The obtained reaction polymer solution was dropwise added to an excess amount of n-heptane, and an operation to deposit a polymer was conducted. Thereafter, the precipitated white powder was separated by filtration, followed by washing with methanol and drying, thereby obtaining 31.2 g of a polymeric compound (1) as an objective compound.

With respect to the polymeric compound (1), the weight average molecular weight (Mw) and the dispersity (Mw/Mn) were determined by the polystyrene equivalent value as measured by gel permeation chromatography (GPC). As a result, it was found that the weight average molecular weight was 6,800, and the dispersity was 1.72. Further, as a result of an analysis by carbon 13 nuclear magnetic resonance spectroscopy (600 MHz, $^{13}$C-NMR), it was found that the composition of the copolymer (ratio (molar ratio) of the respective structural units within the structural formula) was l/m/n=41.7/39.9/18.4.

[Chemical Formula 88]

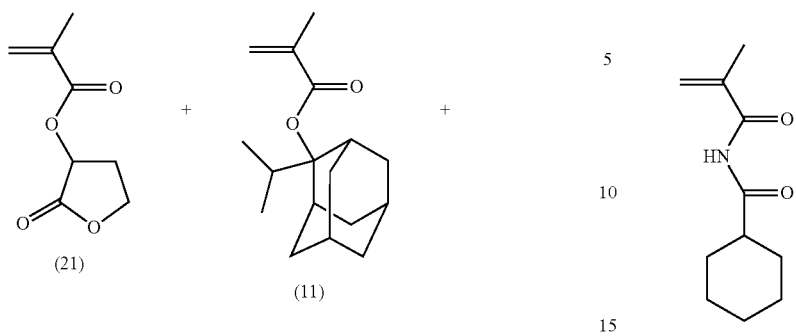

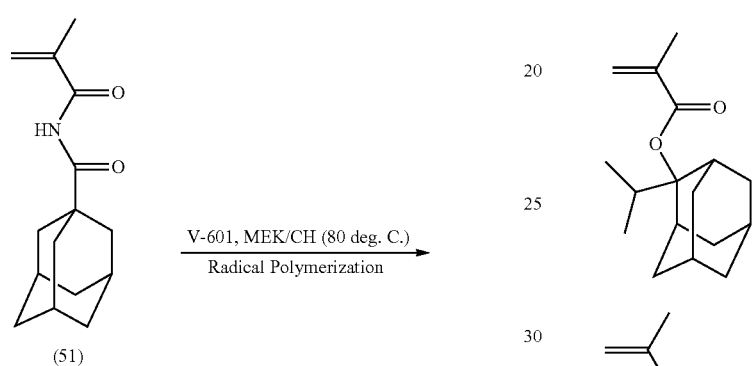

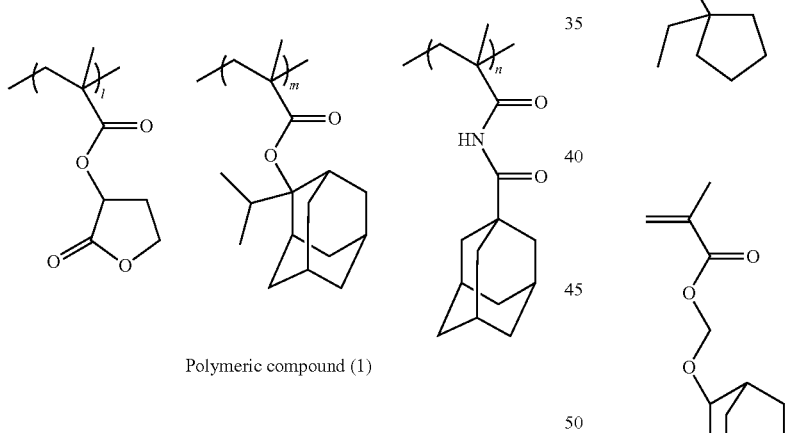

Polymeric compound (1)

Examples 11 to 26, Comparative Examples 1 and 2

Polymeric compounds (2) to (19) were synthesized in the same manner as in Example 10, except that the aforementioned compounds (51) to (59) and the following compounds (10) to (15), (21), (22), (31) and (32) which derived the structural units constituting each polymeric compound were used in predetermined molar ratio.

With respect to each polymeric compound, the structural units for deriving the compound, the copolymer compositional ratio as determined by carbon 13 nuclear magnetic resonance spectrometry (600 MHz $^{13}$C-NMR) and the weight average molecular weight and the dispersity (Mw/Mn) determined by the polystyrene equivalent value as measured by gel permeation chromatography (GPC) are shown in Table 1.

[Chemical Formula 89]

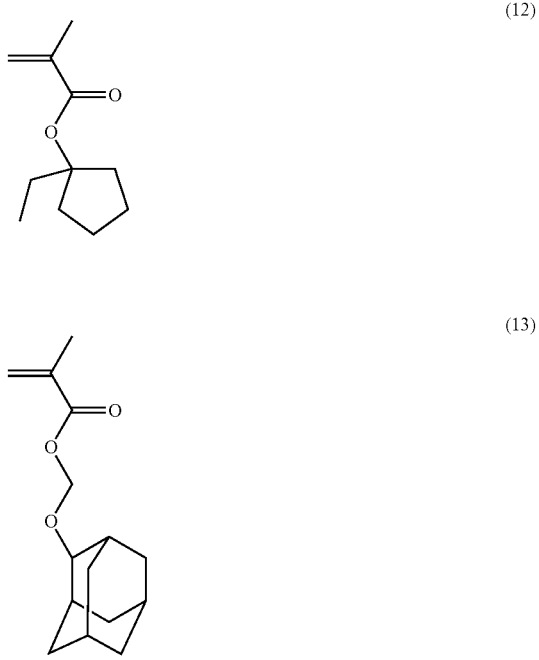

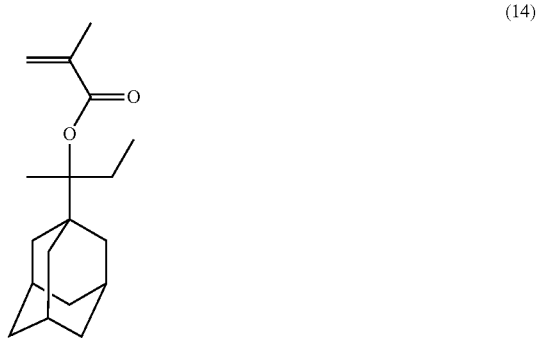

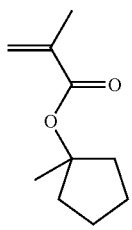
(15)
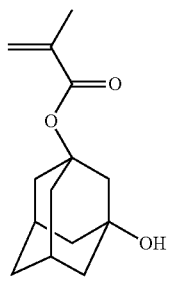
[Chemical Formula 90]
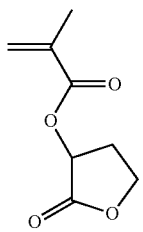
(21)
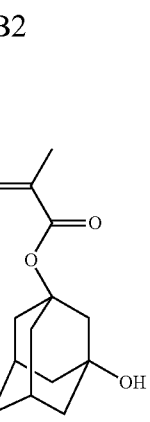
(22)
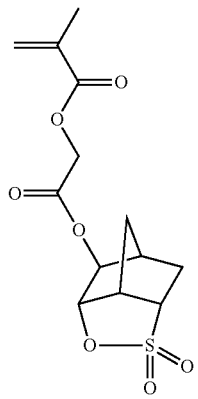
(31)
(32)
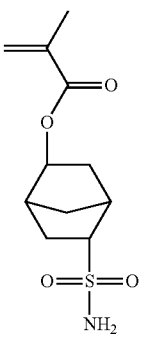
TABLE 1
| | Polymeric compound | Structural units for deriving compound | Copolymer compositional ratio | Mw | Mw/Mn |
|---|---|---|---|---|---|
| Ex. 10 | (1) | (21)/(11)/(51) | 41.7/39.9/18.4 | 6800 | 1.72 |
| Ex. 11 | (2) | (21)/(12)/(51) | 43.7/39.9/16.4 | 7300 | 1.68 |
| Ex. 12 | (3) | (21)/(13)/(51) | 41.6/38.8/19.6 | 5800 | 1.72 |
| Ex. 13 | (4) | (22)/(11)/(51) | 42.9/39.2/17.9 | 6100 | 1.80 |
| Ex. 14 | (5) | (22)/(14)/(51) | 43.0/37.5/19.5 | 7000 | 1.64 |
| Ex. 15 | (6) | (21)/(22)/(11)/(15)/(51) | 34.8/21.2/17.1/13.6/13.3 | 6900 | 1.65 |
| Ex. 16 | (7) | (22)/(11)/(31)/(51) | 28.1/40.7/9.4/21.8 | 6900 | 1.74 |
| Ex. 17 | (8) | (22)/(11)/(32)/(51) | 27.1/42.3/9.0/21.6 | 6600 | 1.75 |
| Ex. 18 | (9) | (21)/(11)/(52) | 41.0/39.0/20.0 | 5500 | 1.66 |
| Ex. 19 | (10) | (21)/(11)/(53) | 44.2/38.3/17.6 | 6800 | 1.64 |
| Ex. 20 | (11) | (21)/(11)/(54) | 42.8/37.9/19.3 | 7700 | 1.65 |
| Ex. 21 | (12) | (21)/(11)/(55) | 41.1/37.6/21.3 | 7900 | 1.72 |
| Comp. Ex. 1 | (13) | (21)/(12)/(31) | 43.4/38.5/18.1 | 7900 | 1.67 |
| Comp. Ex. 2 | (14) | (21)/(12)/(10) | 40.2/40.8/19.0 | 5400 | 1.72 |
| Ex. 22 | (15) | (11)/(54) | 39.4/60.6 | 8100 | 1.70 |
| Ex. 23 | (16) | (21)/(11)/(56) | 43.0/38.4/18.6 | 6900 | 1.65 |
| Ex. 24 | (17) | (21)/(11)/(57) | 43.6/37.5/18.9 | 7000 | 1.64 |
| Ex. 25 | (18) | (21)/(11)/(58) | 44.7/36.8/18.5 | 5600 | 1.74 |
| Ex. 26 | (19) | (21)/(11)/(59) | 42.0/39.3/18.7 | 6200 | 1.72 |

<Production of Resist Composition>

Examples 27 to 47, Comparative Examples 3 to 5

The components shown in Table 2 to 4 were mixed together and dissolved to obtain resist compositions.

TABLE 2

| | Component (A) | Component (B) | Component (D) | Component (E) | Component (S) | |
|---|---|---|---|---|---|---|
| Ex. 27 | (A)-1 [100] | (B)-1 [38.2] | (D)-1 [1.5] | (E)-1 [0.6] | (S)-1 [200] | (S)-2 [5000] |
| Ex. 28 | (A)-2 [100] | (B)-1 [38.2] | (D)-1 [1.5] | (E)-1 [0.6] | (S)-1 [200] | (S)-2 [5000] |
| Ex. 29 | (A)-3 [100] | (B)-1 [38.2] | (D)-1 [1.5] | (E)-1 [0.6] | (S)-1 [200] | (S)-2 [5000] |
| Ex. 30 | (A)-4 [100] | (B)-1 [38.2] | (D)-1 [1.5] | (E)-1 [0.6] | (S)-1 [200] | (S)-2 [5000] |
| Ex. 31 | (A)-5 [100] | (B)-1 [38.2] | (D)-1 [1.5] | (E)-1 [0.6] | (S)-1 [200] | (S)-2 [5000] |
| Ex. 32 | (A)-6 [100] | (B)-1 [38.2] | (D)-1 [1.5] | (E)-1 [0.6] | (S)-1 [200] | (S)-2 [5000] |
| Ex. 33 | (A)-7 [100] | (B)-1 [38.2] | (D)-1 [1.5] | (E)-1 [0.6] | (S)-1 [200] | (S)-2 [5000] |
| Ex. 34 | (A)-8 [100] | (B)-1 [38.2] | (D)-1 [1.5] | (E)-1 [0.6] | (S)-1 [200] | (S)-2 [5000] |
| Ex. 35 | (A)-9 [100] | (B)-1 [38.2] | (D)-1 [1.5] | (E)-1 [0.6] | (S)-1 [200] | (S)-2 [5000] |
| Ex. 36 | (A)-10 [100] | (B)-1 [38.2] | (D)-1 [1.5] | (E)-1 [0.6] | (S)-1 [200] | (S)-2 [5000] |
| Ex. 37 | (A)-11 [100] | (B)-1 [38.2] | (D)-1 [1.5] | (E)-1 [0.6] | (S)-1 [200] | (S)-2 [5000] |
| Ex. 38 | (A)-12 [100] | (B)-1 [38.2] | (D)-1 [1.5] | (E)-1 [0.6] | (S)-1 [200] | (S)-2 [5000] |
| Ex. 39 | (A)-1 [100] | (B)-1 [38.2] | (D)-2 [2.1] | — | (S)-1 [200] | (S)-2 [5000] |
| Comp. Ex. 3 | (A)-13 [100] | (B)-1 [38.2] | (D)-1 [1.5] | (E)-1 [0.6] | (S)-1 [200] | (S)-2 [5000] |
| Comp. Ex. 4 | (A)-14 [100] | (B)-1 [38.2] | (D)-1 [1.5] | (E)-1 [0.6] | (S)-1 [200] | (S)-2 [5000] |

TABLE 3

| | Component (A) | Component (B) | Component (D) | Component (F) | Component (S) |
|---|---|---|---|---|---|
| Ex. 40 | (A)-1 [100] | (B)-1 [12.0] | (D)-3 [3.0] | (F)-1 [3.0] | (S)-3 [3130] |
| Ex. 41 | (A)-4 [100] | (B)-1 [12.0] | (D)-3 [3.0] | (F)-1 [3.0] | (S)-3 [3130] |
| Ex. 42 | (A)-6 [100] | (B)-1 [12.0] | (D)-3 [3.0] | (F)-1 [3.0] | (S)-3 [3130] |
| Comp. Ex. 5 | (A)-13 [100] | (B)-1 [12.0] | (D)-3 [3.0] | (F)-1 [3.0] | (S)-3 [3130] |

TABLE 4

| | Component (A) | Component (B) | Component (D) | Component (E) | Component (S) | |
|---|---|---|---|---|---|---|
| Ex. 43 | (A)-15 [100] | (B)-1 [38.2] | (D)-1 [1.5] | (E)-1 [0.6] | (S)-1 [200] | (S)-2 [5000] |
| Ex. 44 | (A)-16 [100] | (B)-1 [38.2] | (D)-1 [1.5] | (E)-1 [0.6] | (S)-1 [200] | (S)-2 [5000] |
| Ex. 45 | (A)-17 [100] | (B)-1 [38.2] | (D)-1 [1.5] | (E)-1 [0.6] | (S)-1 [200] | (S)-2 [5000] |
| Ex. 46 | (A)-18 [100] | (B)-1 [38.2] | (D)-1 [1.5] | (E)-1 [0.6] | (S)-1 [200] | (S)-2 [5000] |
| Ex. 47 | (A)-19 [100] | (B)-1 [38.2] | (D)-1 [1.5] | (E)-1 [0.6] | (S)-1 [200] | (S)-2 [5000] |

In Tables 2 to 4, the values in brackets [ ] indicate the amount (in terms of parts by weight) of the component added, and the reference characters indicate the following.

(A)-1 to (A)-19: the aforementioned polymeric compounds (1) to (19)

(B)-1: an acid generator consisting of a compound represented by chemical formula (B)-1 shown below (D)-1: tri-n-octylamine.

(D)-2: a compound represented by chemical formula (D)-2 shown below (D)-3: a compound represented by chemical formula (D)-3 shown below (E)-1: salicylic acid (F)-1: a fluorine-containing polymer (homopolymer) represented by formula (F-1) shown below. Mw: 20,600, Mw/Mn: 1.67. In the chemical formula (F)-1, the subscript numerals shown on the bottom right of the parentheses ( ) indicate the percentage (mol %) of the respective structural units.

(S)-1: γ-butyrolactone (S)-2: a mixed solvent of PGMEA/PGME/CH (weight ratio: 2250/1500/1250)

(S)-3: a mixed solvent of PGMEA/PGME/CH (weight ratio: 1410/940/780)

PGMEA represents propyleneglycol monomethyletheracetate, PGME represents propyleneglycol monomethylether, and CH represents cyclohexanone.

[Chemical Formula 91]

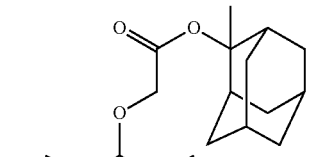

(B)-1

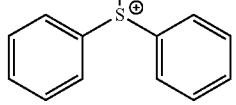

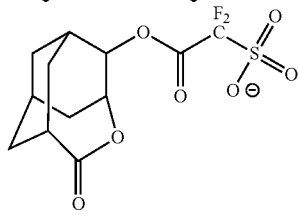

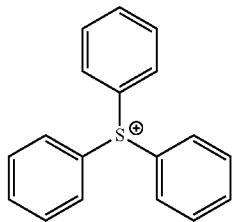

(D)-2

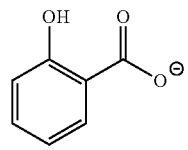

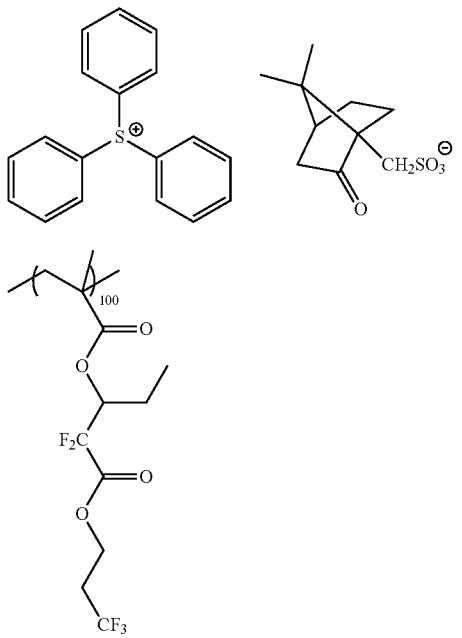

(D)-3

(F)-1

<Formation of Resist Pattern (1)>

Using a spinner, each resist composition shown in Tables 2 and 4 was applied to an 8-inch silicon wafer that had been treated with hexamethyldisilazane (HMDS) at 90° C. for 36 seconds, and the solution was then subjected to a bake treatment (PAB) at a bake temperature of 100° C. for 60 seconds, thereby forming a resist film (film thickness: 60 nm). Subsequently, the resist film was subjected to drawing (exposure) using an electron beam lithography apparatus HL800D (VSB) (manufactured by Hitachi, Ltd.), followed by a bake treatment (PEB: post exposure bake) at a bake temperature of 90° C. for 60 seconds. Then, development was conducted with a 2.38 wt % aqueous TMAH solution (product name: NMD-3; manufactured by Tokyo Ohka Kogyo Co., Ltd.) at 23° C. for 60 seconds.

As a result, in each of the examples, a 1:1 line and space pattern (LS pattern) having a line width of 100 nm and a pitch of 200 nm was formed.

The optimum exposure dose Eop ($\mu C/cm^2$; sensitivity) with which the LS pattern was formed was determined. The results are shown in Table 5.

[Evaluation of Resolution]

A resist pattern was formed in the same manner as in the above <Formation of resist pattern (1)>, and the critical resolution (nm) with the above optimum exposure dose Eop was determined using a scanning electron microscope (product name: S-9380, manufactured by Hitachi High-Technologies Corporation). The results are indicated under "resolution (nm)" in Table 5.

[Evaluation of Exposure Latitude (EL Margin)]

With respect to the above optimum exposure dose Eop, the exposure dose with which an LS pattern having a dimension of the target dimension (line width: 100 nm)±10% (i.e., 90 nm to 110 nm) was determined, and the EL margin (unit: %) was determined by the following formula. The results are indicated under "EL margin (%)" in Table 5.

EL margin(%)=(|E1−E2|/Eop)×100

E1: Exposure dose ($\mu C/cm^2$) with which an LS pattern having a line width of 90 nm was formed E2: Exposure dose ($\mu C/cm^2$) with which an LS pattern having a line width of 110 nm was formed The larger the value of the "EL margin", the smaller the change in the pattern size by the variation of the exposure dose.

[Evaluation of Line Edge Roughness (LER)]

With respect to the LS pattern formed in the above <Formation of resist pattern (1)> having a line width of 100 nm and a pitch of 200 nm, 3σ was determined as a yardstick for indicating LER. The results are indicated under "LER (nm)" in Table 5.

"3σ" indicates a value of 3 times the standard deviation (a) (i.e., 3(s)) (unit: nm) determined by measuring the line width at 400 points in the lengthwise direction of the line using a scanning electron microscope (product name: S-9380, manufactured by Hitachi High-Technologies Corporation; acceleration voltage: 800V).

The smaller this 3s value is, the lower the level of roughness of the line side walls, indicating that a LS pattern with a uniform width was obtained.

[Evaluation of Etching Resistance]

With respect to the resist film formed in the above <Formation of resist pattern (1)> prior to drawing (exposure), dry etching ($O_2$ plasma etching) was conducted under the following conditions using plasma obtained from an oxygen gas, and the etching speed was measured. From the difference in the film thickness of the resist film before and after the etching, the etching rate (the thickness of the film etched per unit time) was determined. The etching resistance was evaluated with the following criteria. The results are shown in Table 5.

($O_2$ Plasma Etching Conditions)

Apparatus: High vacuum RIE apparatus (product name: TCA-2400; manufactured by Tokyo Ohka Kogyo Co., Ltd.).

Gas: a mixed gas containing 60 volume % of an oxygen gas and 40 volume % of a nitrogen gas.

Gas flow rate: 30 sccm ("sccm" refers to a value as measured under 1 atm (atmospheric pressure: 1,013 hPa) at 23° C.)

Temperature inside the chamber: 60° C.

Pressure inside the chamber: 300 mmTorr

Output power applied for generating plasma (RF): 200 W

Treatment time: 60 seconds (Criteria)

A: Etching rate was 600 nm/min or less

B: Etching rate was over 600 nm/min

TABLE 5

| | Eop ($\mu C/cm^2$) | Resolution (nm) | EL margin (%) | LER (nm) | Etching resistance |
|---|---|---|---|---|---|
| Ex. 27 | 45 | 60 | 14.6 | 7.9 | A |
| Ex. 28 | 51 | 60 | 13.5 | 7.5 | A |
| Ex. 29 | 46 | 50 | 16.2 | 7.6 | A |
| Ex. 30 | 44 | 50 | 15.5 | 7.1 | A |
| Ex. 31 | 41 | 50 | 14.8 | 7.4 | A |
| Ex. 32 | 49 | 50 | 18.4 | 7.2 | A |
| Ex. 33 | 42 | 50 | 17.2 | 8.1 | A |
| Ex. 34 | 36 | 50 | 16.7 | 7.6 | A |
| Ex. 35 | 40 | 60 | 14.6 | 8.1 | A |
| Ex. 36 | 43 | 60 | 15.1 | 7.7 | A |
| Ex. 37 | 46 | 60 | 17.0 | 7.4 | A |
| Ex. 38 | 42 | 60 | 16.6 | 7.7 | A |
| Ex. 39 | 46 | 50 | 15.9 | 7.7 | A |
| Comp. Ex. 3 | 59 | 80 | 9.2 | 8.7 | A |
| Comp. Ex. 4 | 50 | 70 | 10.7 | 8.3 | B |
| Ex. 43 | 35 | 60 | 16.2 | 7.8 | A |
| Ex. 44 | 41 | 60 | 16.9 | 8.0 | A |

TABLE 5-continued

|  | Eop (μC/cm²) | Resolution (nm) | EL margin (%) | LER (nm) | Etching resistance |
|---|---|---|---|---|---|
| Ex. 45 | 45 | 60 | 15.5 | 8.2 | A |
| Ex. 46 | 39 | 60 | 17.2 | 7.7 | A |
| Ex. 47 | 34 | 60 | 17.0 | 7.9 | A |

From the results shown in Table 5, the resist compositions of the Examples according to the present invention exhibited excellent properties with respect to sensitivity, resolution, lithography properties and etching resistance, as compared to the resist compositions of the Comparative Examples.

<Formation of Resist Pattern (2)>

An organic anti-reflection film composition (product name: ARC29A, manufactured by Brewer Science Ltd.) was applied to an 12-inch silicon wafer using a spinner, and the composition was then baked at 205° C. for 60 seconds, thereby forming an organic anti-reflection film having a film thickness of 89 nm.

Then, the resist composition was applied to the organic anti-reflection film using a spinner, and was then prebaked (PAB) on a hotplate at 110° C. for 60 seconds and dried, thereby forming a resist film having a film thickness of 90 nm.

Subsequently, the resist film was selectively irradiated with an ArF excimer laser (193 nm) through a mask, using an ArF exposure apparatus NSR-5609B (manufactured by Nikon Corporation; NA (numerical aperture)=1.08; Crosspole).

Next, a post exposure bake (PEB) treatment was conducted at a bake temperature of 90° C. for 60 seconds, followed by alkali development for 10 seconds at 23° C. in a 2.38% by weight aqueous tetramethylammonium hydroxide (TMAH) solution. Then, the resist was washed for 15 seconds with pure water, followed by drying by shaking.

As a result, in each of the examples, a 1:1 line and space pattern (LS pattern) having a line width of 49 nm and a pitch of 98 nm was formed.

The optimum exposure dose Eop (mJ/cm²; sensitivity) with which the LS pattern was formed was determined. The results are shown in Table 6.

[Evaluation of Resolution]

A resist pattern was formed in the same manner as in the above <Formation of resist pattern (2)>, and the critical resolution (nm) with the above optimum exposure dose Eop was determined using a scanning electron microscope (product name: S-9380, manufactured by Hitachi High-Technologies Corporation). The results are indicated under "resolution (nm)" in Table 6.

[Evaluation of Exposure Latitude (EL Margin)]

With respect to the above optimum exposure dose Eop, the exposure dose with which an LS pattern having a dimension of the target dimension (line width: 49 nm)±5% (i.e., 46.55 nm to 51.45 nm) was determined, and the EL margin (unit: %) was determined by the following formula. The results are shown in Table 6.

EL margin(%)=(|E1−E2|/Eop)×100

E1: Exposure dose (mJ/cm²) with which an LS pattern having a line width of 46.55 nm was formed E2: Exposure dose (mJ/cm²) with which an L/S pattern having a line width of 51.45 nm was formed

[Evaluation of Line Width Roughness (LWR)]

With respect to each of the LS patterns formed with the above optimum exposure dose Eop and having a space width of 49 nm and a pitch of 98 nm, the space width at 400 points in the lengthwise direction of the space were measured using a measuring scanning electron microscope (SEM) (product name: S-9380, manufactured by Hitachi High-Technologies Corporation; acceleration voltage: 300V). From the results, the value of 3 times the standard deviation s (i.e., 3s) was determined, and the average of the 3s values at 400 points was calculated as a yardstick of LWR. The results are shown in Table 6.

The smaller this 3s value is, the lower the level of roughness of the line width, indicating that a LS pattern with a uniform width was obtained.

TABLE 6

|  | Eop (mJ/cm²) | Resolution (nm) | EL margin (%) | LWR (nm) |
|---|---|---|---|---|
| Ex. 40 | 28 | 45 | 5.4 | 5.6 |
| Ex. 41 | 26 | 42 | 5.9 | 5.1 |
| Ex. 42 | 29 | 41 | 5.7 | 5.1 |
| Comp. Ex. 5 | 31 | 48 | 4.8 | 6.2 |

From the results shown in Table 6, the resist compositions of the Examples according to the present invention exhibited excellent properties with respect to sensitivity, resolution and lithography properties, as compared to the resist compositions of the Comparative Examples.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

The invention claimed is:

1. A resist composition comprising a base component (A) which exhibits changed solubility in a developing solution under action of acid and an acid-generator component (B) which generates acid upon exposure, the base component (A) comprising a polymeric compound (A1) comprising a structural unit (a1) containing an acid decomposable group that exhibits increased polarity by the action of acid and a structural unit (a5) represented by general formula (a5-0) shown below:

(a5-0)

wherein R represents a hydrogen atom, an alkyl group of 1 to 5 carbon atoms or a halogenated alkyl group of 1 to 5 carbon atoms; $R^1$ represents a sulfur atom or an oxygen atom; $R^2$ represents a single bond or a divalent linking group; and Y represents an aromatic hydrocarbon group or an aliphatic hydrocarbon group having a polycyclic group, provided that the aromatic hydrocarbon group or the aliphatic hydrocarbon may have a carbon atom or a hydrogen atom thereof substituted with a substituent.

2. The resist composition according to claim 1, wherein the amount of the structural unit (a5) based on the combined total of all structural units constituting the component (A1) is 5 to 70 mol %.

3. A method of forming a resist pattern, comprising: using a resist composition according to claim 1 to form a resist film on a substrate, subjecting the resist film to exposure, and subjecting the resist film to developing to form a resist pattern.

4. A polymeric compound having a structural unit (a1) containing an acid decomposable group that exhibits increased polarity by the action of acid and a structural unit (a5) represented by general formula (a5-0) shown below:

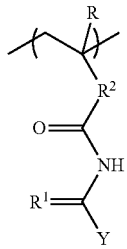

(a5-0)

wherein R represents a hydrogen atom, an alkyl group of 1 to 5 carbon atoms or a halogenated alkyl group of 1 to 5 carbon atoms; $R^1$ represents a sulfur atom or an oxygen atom; $R^2$ represents a single bond or a divalent linking group; and Y represents an aromatic hydrocarbon group or an aliphatic hydrocarbon group having a polycyclic group, provided that the aromatic hydrocarbon group or the aliphatic hydrocarbon may have a carbon atom or a hydrogen atom thereof substituted with a substituent.

5. The polymeric compound according to claim 4, wherein the amount of the structural unit (a5) based on the combined total of all structural units constituting the polymeric compound is 5 to 70 mol %.

* * * * *